United States Patent
Stray et al.

(10) Patent No.: US 12,398,389 B2
(45) Date of Patent: Aug. 26, 2025

(54) METHODS FOR ISOLATING NUCLEIC ACIDS WITH SIZE SELECTION

(71) Applicant: Natera, Inc., San Carlos, CA (US)

(72) Inventors: James Stray, San Mateo, CA (US); Jason Tong, San Carlos, CA (US)

(73) Assignee: Natera, Inc., San Carlos, CA (US)

( * ) Notice: Subject to any disclaimer, the term of this patent is extended or adjusted under 35 U.S.C. 154(b) by 951 days.

(21) Appl. No.: 16/969,892

(22) PCT Filed: Feb. 15, 2019

(86) PCT No.: PCT/US2019/018274
§ 371 (c)(1),
(2) Date: Aug. 13, 2020

(87) PCT Pub. No.: WO2019/161244
PCT Pub. Date: Aug. 22, 2019

(65) Prior Publication Data
US 2021/0009990 A1    Jan. 14, 2021

Related U.S. Application Data

(63) Continuation-in-part of application No. PCT/US2018/018425, filed on Feb. 15, 2018.
(Continued)

(51) Int. Cl.
*C12N 15/10*    (2006.01)
*C12Q 1/6853*   (2018.01)

(52) U.S. Cl.
CPC ....... *C12N 15/1013* (2013.01); *C12Q 1/6853* (2013.01)

(58) Field of Classification Search
CPC ............ C12N 15/1013; C12N 15/1017; C12N 15/1006; C12Q 1/6853; C12Q 2527/125
See application file for complete search history.

(56) References Cited

U.S. PATENT DOCUMENTS 3,520,488 A    7/1970    Vouthier
5,314,809 A    5/1994    Erlich et al.
(Continued)

FOREIGN PATENT DOCUMENTS

CN    1650032 A    8/2005
CN    101675169 A   3/2010
(Continued)

OTHER PUBLICATIONS

Burkova, E. E. et al., "Extremely Stable Soluble High Molecular Mass Multi-Protein Complex with DNase Activity in Human Placental Tissue", PLOS One, vol. 9, No. 11: e011234, Nov. 26, 2014, 26 pages.
(Continued)

*Primary Examiner* — Joseph G. Dauner

(57) ABSTRACT

Disclosed here is a method for isolating nucleic acids from a biological sample, comprising: (a) contacting a first composition comprising nucleic acids obtained from a biological sample with a first matrix under a low-stringency binding condition having less than 1% aliphatic alcohols that binds less than 5% of nucleic acids of shorter than about 118 bp and more than 30% of nucleic acids longer than about 194 bp to a first matrix; and (b) contacting a second composition comprising remainder of the first composition with a second matrix under a high-stringency binding condition having less than 1% aliphatic alcohol that binds more than 70% of nucleic acids longer than about 72 bp and 30% of nucleic acids longer than about 50 bp to the second matrix. Further disclosed is a kit for isolating nucleic acids from a biological sample, comprising (a) a first binding buffer for establishing a low-stringency binding condition having less than 1% aliphatic alcohols that binds less than 5% of nucleic acids shorter than about 118 bp and more than 30% of nucleic acids longer than about 194 bp to a matrix, and (b) a second binding buffer for establishing a high-stringency binding
(Continued)

condition having less than 1% aliphatic alcohol that binds more than 70% of nucleic acids longer than about 72 bp and 30% of nucleic acids longer than about 50 bp to the matrix.

14 Claims, 36 Drawing Sheets

Related U.S. Application Data

(60) Provisional application No. 62/631,336, filed on Feb. 15, 2018.

(56) References Cited

U.S. PATENT DOCUMENTS

| | | | |
|---|---|---|---|
| 5,635,366 A | 6/1997 | Cooke et al. | |
| 5,714,320 A | 2/1998 | Kool | |
| 5,716,776 A | 2/1998 | Bogart | |
| 5,753,467 A | 5/1998 | Jensen et al. | |
| 5,824,467 A | 10/1998 | Mascarenhas | |
| 5,860,917 A | 1/1999 | Comanor et al. | |
| 5,972,602 A | 10/1999 | Hyland et al. | |
| 5,994,148 A | 11/1999 | Stewart et al. | |
| 6,001,611 A | 12/1999 | Will | |
| 6,025,128 A | 2/2000 | Veltri et al. | |
| 6,066,454 A | 5/2000 | Lipshutz et al. | |
| 6,100,029 A | 8/2000 | Lapidus et al. | |
| 6,108,635 A | 8/2000 | Herren et al. | |
| 6,143,496 A | 11/2000 | Brown et al. | |
| 6,180,349 B1 | 1/2001 | Ginzinger et al. | |
| 6,214,558 B1 | 4/2001 | Shuber et al. | |
| 6,258,540 B1 | 7/2001 | Lo et al. | |
| 6,300,077 B1 | 10/2001 | Shuber et al. | |
| 6,440,706 B1 | 8/2002 | Vogelstein et al. | |
| 6,479,235 B1 | 11/2002 | Schumm et al. | |
| 6,489,135 B1 | 12/2002 | Parrott | |
| 6,720,140 B1 | 4/2004 | Hartley et al. | |
| 6,794,140 B1 | 9/2004 | Goldsborough | |
| 6,807,491 B2 | 10/2004 | Pavlovic et al. | |
| 6,852,487 B1 | 2/2005 | Barany et al. | |
| 6,958,211 B2 | 10/2005 | Vingerhoets et al. | |
| 6,964,847 B1 | 11/2005 | Englert | |
| 7,035,739 B2 | 4/2006 | Schadt et al. | |
| 7,058,517 B1 | 6/2006 | Denton et al. | |
| 7,058,616 B1 | 6/2006 | Larder et al. | |
| 7,218,764 B2 | 5/2007 | Vaisberg et al. | |
| 7,297,485 B2 | 11/2007 | Bornarth et al. | |
| 7,332,277 B2 | 2/2008 | Dhallan | |
| 7,414,118 B1 | 8/2008 | Mullah et al. | |
| 7,442,506 B2 | 10/2008 | Dhallan | |
| 7,459,273 B2 | 12/2008 | Jones et al. | |
| 7,645,576 B2 | 1/2010 | Lo et al. | |
| 7,700,325 B2 | 4/2010 | Cantor et al. | |
| 7,718,367 B2 | 5/2010 | Lo et al. | |
| 7,718,370 B2 | 5/2010 | Dhallan | |
| 7,727,720 B2 | 6/2010 | Dhallan | |
| 7,785,798 B2 | 8/2010 | Cantor et al. | |
| 7,790,393 B2 | 9/2010 | Lyamichev et al. | |
| 7,805,282 B2 | 9/2010 | Casey | |
| 7,838,647 B2 | 11/2010 | Hahn et al. | |
| 7,888,017 B2 | 2/2011 | Quake et al. | |
| 8,008,018 B2 | 8/2011 | Quake et al. | |
| 8,024,128 B2 | 9/2011 | Rabinowitz et al. | |
| 8,137,912 B2 | 3/2012 | Kapur et al. | |
| 8,168,389 B2 | 5/2012 | Shoemaker et al. | |
| 8,173,370 B2 | 5/2012 | Oeth et al. | |
| 8,195,415 B2 | 6/2012 | Fan et al. | |
| 8,296,076 B2 | 10/2012 | Fan et al. | |
| 8,304,187 B2 | 11/2012 | Fernando | |
| 8,318,430 B2 | 11/2012 | Chuu et al. | |
| 8,467,976 B2 | 6/2013 | Lo et al. | |
| 8,515,679 B2 | 8/2013 | Rabinowitz et al. | |
| 8,532,930 B2 | 9/2013 | Rabinowitz et al. | |
| 8,682,592 B2 | 3/2014 | Rabinowitz et al. | |
| 8,825,412 B2 | 9/2014 | Rabinowitz et al. | |
| 9,085,798 B2 | 7/2015 | Chee | |
| 9,364,829 B2 | 6/2016 | Heid et al. | |
| 9,476,095 B2 | 10/2016 | Vogelstein et al. | |
| 9,487,829 B2 | 11/2016 | Vogelstein et al. | |
| 9,598,731 B2 | 3/2017 | Talasaz | |
| 9,677,118 B2 | 6/2017 | Zimmermann et al. | |
| 9,784,742 B2 | 10/2017 | Benz et al. | |
| 10,011,870 B2 | 7/2018 | Zimmermann et al. | |
| 10,081,839 B2 | 9/2018 | Rabinowitz et al. | |
| 10,083,273 B2 | 9/2018 | Rabinowitz et al. | |
| 10,229,244 B2 | 3/2019 | Ghosh | |
| 11,319,596 B2 | 5/2022 | Babiarz et al. | |
| 11,371,100 B2 | 6/2022 | Babiarz et al. | |
| 2001/0051341 A1 | 12/2001 | Lo et al. | |
| 2001/0053519 A1 | 12/2001 | Fodor et al. | |
| 2002/0006622 A1 | 1/2002 | Bradley et al. | |
| 2002/0107640 A1 | 8/2002 | Ideker et al. | |
| 2003/0009295 A1 | 1/2003 | Markowitz et al. | |
| 2003/0065535 A1 | 4/2003 | Karlov et al. | |
| 2003/0077586 A1 | 4/2003 | Pavlovic et al. | |
| 2003/0101000 A1 | 5/2003 | Bader et al. | |
| 2003/0119004 A1 | 6/2003 | Wenz et al. | |
| 2003/0228613 A1 | 12/2003 | Bornarth et al. | |
| 2003/0235848 A1 | 12/2003 | Neville et al. | |
| 2004/0033596 A1 | 2/2004 | Threadgill et al. | |
| 2004/0136967 A1 | 7/2004 | Weiss et al. | |
| 2004/0137470 A1 | 7/2004 | Dhallan | |
| 2004/0146866 A1 | 7/2004 | Fu | |
| 2004/0157243 A1 | 8/2004 | Huang et al. | |
| 2004/0197797 A1 | 10/2004 | Inoko et al. | |
| 2004/0209299 A1 | 10/2004 | Pinter et al. | |
| 2004/0229231 A1 | 11/2004 | Frudakis et al. | |
| 2004/0236518 A1 | 11/2004 | Pavlovic et al. | |
| 2004/0259100 A1 | 12/2004 | Gunderson et al. | |
| 2005/0009069 A1 | 1/2005 | Liu et al. | |
| 2005/0049793 A1 | 3/2005 | Paterlini-Brechot | |
| 2005/0079535 A1 | 4/2005 | Kirchgesser et al. | |
| 2005/0123914 A1 | 6/2005 | Katz et al. | |
| 2005/0130173 A1 | 6/2005 | Leamon et al. | |
| 2005/0142577 A1 | 6/2005 | Jones et al. | |
| 2005/0144664 A1 | 6/2005 | Smith et al. | |
| 2005/0164241 A1 | 7/2005 | Hahn et al. | |
| 2005/0216207 A1 | 9/2005 | Kermani | |
| 2005/0221341 A1 | 10/2005 | Shimkets et al. | |
| 2005/0227263 A1 | 10/2005 | Green et al. | |
| 2005/0250111 A1 | 11/2005 | Xie et al. | |
| 2005/0255508 A1 | 11/2005 | Casey | |
| 2005/0272073 A1 | 12/2005 | Vaisberg et al. | |
| 2006/0019278 A1 | 1/2006 | Lo et al. | |
| 2006/0040300 A1 | 2/2006 | Dapprich et al. | |
| 2006/0051799 A1 | 3/2006 | Iwaki et al. | |
| 2006/0052945 A1 | 3/2006 | Rabinowitz et al. | |
| 2006/0057618 A1 | 3/2006 | Piper et al. | |
| 2006/0068394 A1 | 3/2006 | Langmore et al. | |
| 2006/0088574 A1 | 4/2006 | Manning et al. | |
| 2006/0088912 A1 | 4/2006 | Yan et al. | |
| 2006/0099614 A1 | 5/2006 | Gill et al. | |
| 2006/0121452 A1 | 6/2006 | Dhallan | |
| 2006/0134662 A1 | 6/2006 | Pratt et al. | |
| 2006/0141499 A1 | 6/2006 | Sher et al. | |
| 2006/0210997 A1 | 9/2006 | Myerson et al. | |
| 2006/0216738 A1 | 9/2006 | Wada et al. | |
| 2006/0229823 A1 | 10/2006 | Liu et al. | |
| 2006/0281105 A1 | 12/2006 | Li et al. | |
| 2007/0020640 A1 | 1/2007 | McCloskey et al. | |
| 2007/0027636 A1 | 2/2007 | Rabinowitz | |
| 2007/0042384 A1 | 2/2007 | Li et al. | |
| 2007/0059707 A1 | 3/2007 | Cantor et al. | |
| 2007/0122805 A1 | 5/2007 | Cantor et al. | |
| 2007/0128624 A1 | 6/2007 | Gormley et al. | |
| 2007/0178478 A1 | 8/2007 | Dhallan et al. | |
| 2007/0178501 A1 | 8/2007 | Rabinowitz et al. | |
| 2007/0184467 A1 | 8/2007 | Rabinowitz et al. | |
| 2007/0202525 A1 | 8/2007 | Quake et al. | |
| 2007/0202536 A1 | 8/2007 | Yamanishi et al. | |
| 2007/0207466 A1 | 9/2007 | Cantor et al. | |
| 2007/0212689 A1 | 9/2007 | Bianchi et al. | |
| 2007/0243549 A1 | 10/2007 | Bischoff | |
| 2007/0259351 A1 | 11/2007 | Chinitz et al. | |

(56) References Cited

U.S. PATENT DOCUMENTS

| | | |
|---|---|---|
| 2008/0020390 A1 | 1/2008 | Mitchell et al. |
| 2008/0026390 A1 | 1/2008 | Stoughton et al. |
| 2008/0038733 A1 | 2/2008 | Bischoff et al. |
| 2008/0070792 A1 | 3/2008 | Stoughton et al. |
| 2008/0071076 A1 | 3/2008 | Hahn et al. |
| 2008/0085836 A1 | 4/2008 | Kearns et al. |
| 2008/0090239 A1 | 4/2008 | Shoemaker et al. |
| 2008/0102455 A1 | 5/2008 | Poetter |
| 2008/0138809 A1 | 6/2008 | Kapur et al. |
| 2008/0182244 A1 | 7/2008 | Tafas et al. |
| 2008/0193927 A1 | 8/2008 | Mann et al. |
| 2008/0220422 A1 | 9/2008 | Shoemaker et al. |
| 2008/0234142 A1 | 9/2008 | Lietz |
| 2008/0243398 A1 | 10/2008 | Rabinowitz et al. |
| 2009/0023190 A1 | 1/2009 | Lao et al. |
| 2009/0029377 A1 | 1/2009 | Lo et al. |
| 2009/0087847 A1 | 4/2009 | Lo et al. |
| 2009/0098534 A1 | 4/2009 | Weier et al. |
| 2009/0099041 A1 | 4/2009 | Church et al. |
| 2009/0143570 A1* | 6/2009 | Jiang .................. C07K 1/34 530/413 |
| 2009/0176662 A1 | 7/2009 | Rigatti et al. |
| 2009/0221620 A1 | 9/2009 | Luke et al. |
| 2010/0035232 A1 | 2/2010 | Ecker et al. |
| 2010/0112575 A1 | 5/2010 | Fan et al. |
| 2010/0112590 A1 | 5/2010 | Lo et al. |
| 2010/0120038 A1 | 5/2010 | Mir et al. |
| 2010/0124751 A1 | 5/2010 | Quake et al. |
| 2010/0129874 A1 | 5/2010 | Mitra et al. |
| 2010/0138165 A1 | 6/2010 | Fan et al. |
| 2010/0171954 A1 | 7/2010 | Quake et al. |
| 2010/0184069 A1 | 7/2010 | Fernando et al. |
| 2010/0184152 A1 | 7/2010 | Sandler et al. |
| 2010/0196892 A1 | 8/2010 | Quake et al. |
| 2010/0203538 A1 | 8/2010 | Dube et al. |
| 2010/0216153 A1 | 8/2010 | Lapidus et al. |
| 2010/0248231 A1 | 9/2010 | Wei et al. |
| 2010/0255492 A1 | 10/2010 | Quake et al. |
| 2010/0256013 A1 | 10/2010 | Quake et al. |
| 2010/0273678 A1 | 10/2010 | Alexandre et al. |
| 2010/0285537 A1 | 11/2010 | Zimmermann |
| 2010/0291572 A1 | 11/2010 | Stoughton et al. |
| 2010/0323352 A1 | 12/2010 | Lo et al. |
| 2011/0033862 A1 | 2/2011 | Rabinowitz et al. |
| 2011/0039724 A1 | 2/2011 | Lo et al. |
| 2011/0071031 A1 | 3/2011 | Khripin et al. |
| 2011/0086769 A1 | 4/2011 | Oliphant et al. |
| 2011/0092763 A1 | 4/2011 | Rabinowitz et al. |
| 2011/0105353 A1 | 5/2011 | Lo et al. |
| 2011/0151442 A1 | 6/2011 | Fan et al. |
| 2011/0159499 A1 | 6/2011 | Hindson et al. |
| 2011/0160078 A1 | 6/2011 | Fodor et al. |
| 2011/0178719 A1 | 7/2011 | Rabinowitz et al. |
| 2011/0201507 A1 | 8/2011 | Rava et al. |
| 2011/0224087 A1 | 9/2011 | Quake et al. |
| 2011/0246083 A1 | 10/2011 | Fan et al. |
| 2011/0251149 A1 | 10/2011 | Perrine et al. |
| 2011/0288780 A1 | 11/2011 | Rabinowitz et al. |
| 2011/0300608 A1 | 12/2011 | Ryan et al. |
| 2011/0301854 A1 | 12/2011 | Curry et al. |
| 2011/0318734 A1 | 12/2011 | Lo et al. |
| 2012/0003635 A1 | 1/2012 | Lo et al. |
| 2012/0010085 A1 | 1/2012 | Rava et al. |
| 2012/0028814 A1 | 2/2012 | Toloue et al. |
| 2012/0034603 A1 | 2/2012 | Oliphant et al. |
| 2012/0122701 A1 | 5/2012 | Ryan et al. |
| 2012/0165203 A1 | 6/2012 | Quake et al. |
| 2012/0185176 A1 | 7/2012 | Rabinowitz et al. |
| 2012/0190020 A1 | 7/2012 | Oliphant et al. |
| 2012/0190021 A1 | 7/2012 | Oliphant et al. |
| 2012/0191358 A1 | 7/2012 | Oliphant et al. |
| 2012/0196754 A1 | 8/2012 | Quake et al. |
| 2012/0214678 A1 | 8/2012 | Rava et al. |
| 2012/0264121 A1 | 10/2012 | Rava et al. |
| 2012/0270212 A1 | 10/2012 | Rabinowitz et al. |
| 2012/0295819 A1 | 11/2012 | Leamon et al. |
| 2013/0017549 A1 | 1/2013 | Hong |
| 2013/0024127 A1 | 1/2013 | Stuelpnagel et al. |
| 2013/0034546 A1 | 2/2013 | Rava et al. |
| 2013/0060483 A1 | 3/2013 | Struble et al. |
| 2013/0069869 A1 | 3/2013 | Akao et al. |
| 2013/0090250 A1 | 4/2013 | Sparks et al. |
| 2013/0116130 A1 | 5/2013 | Fu et al. |
| 2013/0123120 A1 | 5/2013 | Zimmermann et al. |
| 2013/0130923 A1 | 5/2013 | Ehrich et al. |
| 2013/0157870 A1 | 6/2013 | Pushkarev et al. |
| 2013/0178373 A1 | 7/2013 | Rabinowitz et al. |
| 2013/0190653 A1 | 7/2013 | Alvarez Ramos |
| 2013/0196862 A1 | 8/2013 | Rabinowitz et al. |
| 2013/0210644 A1 | 8/2013 | Stoughton et al. |
| 2013/0225422 A1 | 8/2013 | Rabinowitz et al. |
| 2013/0237431 A1 | 9/2013 | Lo et al. |
| 2013/0252824 A1 | 9/2013 | Rabinowitz et al. |
| 2013/0253369 A1 | 9/2013 | Rabinowitz et al. |
| 2013/0261004 A1 | 10/2013 | Ryan et al. |
| 2013/0274116 A1 | 10/2013 | Rabinowitz et al. |
| 2013/0288252 A1 | 10/2013 | Sparks et al. |
| 2013/0303461 A1 | 11/2013 | Iafrate et al. |
| 2013/0310260 A1 | 11/2013 | Kim et al. |
| 2013/0323731 A1 | 12/2013 | Lo et al. |
| 2014/0032128 A1 | 1/2014 | Rabinowitz et al. |
| 2014/0038830 A1 | 2/2014 | Srinivasan et al. |
| 2014/0051585 A1 | 2/2014 | Prosen et al. |
| 2014/0065621 A1 | 3/2014 | Mhatre et al. |
| 2014/0087385 A1 | 3/2014 | Rabinowitz et al. |
| 2014/0094373 A1 | 4/2014 | Zimmermann et al. |
| 2014/0100126 A1 | 4/2014 | Rabinowitz |
| 2014/0100134 A1 | 4/2014 | Rabinowitz et al. |
| 2014/0141981 A1 | 5/2014 | Zimmermann et al. |
| 2014/0154682 A1 | 6/2014 | Rabinowitz et al. |
| 2014/0162269 A1 | 6/2014 | Rabinowitz et al. |
| 2014/0186827 A1 | 7/2014 | Pieprzyk et al. |
| 2014/0193816 A1 | 7/2014 | Rabinowitz et al. |
| 2014/0206552 A1 | 7/2014 | Rabinowitz et al. |
| 2014/0227691 A1 | 8/2014 | May et al. |
| 2014/0227705 A1 | 8/2014 | Vogelstein et al. |
| 2014/0242588 A1 | 8/2014 | Van Den Boom et al. |
| 2014/0256558 A1 | 9/2014 | Varley et al. |
| 2014/0256569 A1 | 9/2014 | Rabinowitz et al. |
| 2014/0272956 A1 | 9/2014 | Huang et al. |
| 2014/0274740 A1 | 9/2014 | Srinivasan et al. |
| 2014/0287934 A1 | 9/2014 | Szelinger et al. |
| 2014/0329245 A1 | 11/2014 | Spier et al. |
| 2014/0336060 A1 | 11/2014 | Rabinowitz et al. |
| 2015/0051087 A1 | 2/2015 | Rabinowitz et al. |
| 2015/0064695 A1 | 3/2015 | Katz et al. |
| 2015/0099673 A1 | 4/2015 | Fodor et al. |
| 2015/0147815 A1 | 5/2015 | Babiarz et al. |
| 2015/0167069 A1 | 6/2015 | Schutz et al. |
| 2015/0197786 A1 | 7/2015 | Osborne et al. |
| 2015/0218631 A1 | 8/2015 | Chuu et al. |
| 2015/0232938 A1 | 8/2015 | Mhatre et al. |
| 2015/0265995 A1 | 9/2015 | Head et al. |
| 2016/0186253 A1 | 6/2016 | Talasaz et al. |
| 2016/0201124 A1 | 7/2016 | Donahue et al. |
| 2016/0257993 A1 | 9/2016 | Fu et al. |
| 2016/0289740 A1 | 10/2016 | Fu et al. |
| 2016/0289753 A1 | 10/2016 | Osborne et al. |
| 2016/0312276 A1 | 10/2016 | Fu et al. |
| 2016/0319345 A1 | 11/2016 | Gnerre et al. |
| 2017/0121716 A1 | 5/2017 | Rodi |
| 2017/0137882 A1 | 5/2017 | Goossens et al. |
| 2017/0298427 A1 | 10/2017 | Buis et al. |
| 2018/0148777 A1 | 5/2018 | Kirkizlar et al. |
| 2018/0155775 A1 | 6/2018 | Zimmermann et al. |
| 2018/0155776 A1 | 6/2018 | Zimmermann et al. |
| 2018/0155779 A1 | 6/2018 | Zimmermann et al. |
| 2018/0155785 A1 | 6/2018 | Rabinowitz et al. |
| 2018/0155786 A1 | 6/2018 | Rabinowitz et al. |
| 2018/0155792 A1 | 6/2018 | Rabinowitz et al. |
| 2018/0171409 A1 | 6/2018 | Rabinowitz et al. |
| 2018/0171420 A1 | 6/2018 | Babiarz et al. |
| 2018/0173845 A1 | 6/2018 | Sigurjonsson et al. |
| 2018/0173846 A1 | 6/2018 | Sigurjonsson et al. |

(56) References Cited

U.S. PATENT DOCUMENTS

| | | |
|---|---|---|
| 2018/0201995 A1 | 7/2018 | Rabinowitz et al. |
| 2018/0237841 A1 | 8/2018 | Stray et al. |
| 2018/0298439 A1 | 10/2018 | Ryan et al. |
| 2018/0300448 A1 | 10/2018 | Rabinowitz et al. |
| 2018/0320171 A1 | 11/2018 | Withey |
| 2019/0010543 A1 | 1/2019 | Babiarz et al. |
| 2019/0106737 A1 | 4/2019 | Underhill |
| 2019/0106751 A1 | 4/2019 | Zimmermann et al. |
| 2019/0256894 A1 | 8/2019 | Zimmermann et al. |
| 2019/0256908 A1 | 8/2019 | Rabinowitz et al. |
| 2019/0256912 A1 | 8/2019 | Rabinowitz et al. |
| 2019/0256919 A1 | 8/2019 | Babiarz et al. |
| 2019/0256931 A1 | 8/2019 | Babiarz et al. |
| 2020/0126634 A1 | 4/2020 | Sigurjonsson et al. |
| 2021/0032692 A1 | 2/2021 | Mitchell et al. |
| 2022/0098667 A1 | 3/2022 | Rabinowitz et al. |
| 2022/0139495 A1 | 5/2022 | Rabinowitz et al. |
| 2022/0154249 A1 | 5/2022 | Zimmermann et al. |
| 2022/0154290 A1 | 5/2022 | Babiarz et al. |
| 2022/0195526 A1 | 6/2022 | Rabinowitz et al. |
| 2022/0213561 A1 | 7/2022 | Babiarz et al. |
| 2022/0251654 A1 | 8/2022 | Hafez et al. |
| 2022/0282335 A1 | 9/2022 | Babiarz et al. |
| 2022/0307086 A1 | 9/2022 | Babiarz et al. |
| 2022/0403461 A1 | 12/2022 | Kirkizlar et al. |
| 2023/0060579 A1 | 3/2023 | Bethke et al. |
| 2023/0193387 A1 | 6/2023 | Rabinowitz |
| 2023/0212693 A1 | 7/2023 | Rabinowitz et al. |

FOREIGN PATENT DOCUMENTS

| | | |
|---|---|---|
| EP | 0270017 A2 | 6/1988 |
| EP | 1524321 A1 | 4/2005 |
| EP | 1524321 B1 | 7/2009 |
| EP | 2163622 A1 | 3/2010 |
| EP | 2128169 A1 | 12/2010 |
| EP | 2653562 A1 | 10/2013 |
| EP | 2902500 A1 | 8/2015 |
| EP | 2315849 B1 | 11/2017 |
| GB | 2488358 A | 8/2012 |
| RU | 2290078 C1 | 12/2006 |
| WO | WO-2001090419 A2 | 11/2001 |
| WO | WO-2002004672 A2 | 1/2002 |
| WO | WO-2002055985 A2 | 7/2002 |
| WO | WO-2003031646 A1 | 4/2003 |
| WO | WO-2003062441 A1 | 7/2003 |
| WO | WO-2001090419 A9 | 11/2003 |
| WO | WO-2004087863 A2 | 10/2004 |
| WO | WO-2005021793 A1 | 3/2005 |
| WO | WO-2005035725 A2 | 4/2005 |
| WO | WO-2005100401 A2 | 10/2005 |
| WO | WO-2005123779 A2 | 12/2005 |
| WO | WO-2007057647 A1 | 5/2007 |
| WO | WO-2007062164 A2 | 5/2007 |
| WO | WO-2007070482 A2 | 6/2007 |
| WO | WO-2007117256 A1 | 10/2007 |
| WO | WO-2007132167 A2 | 11/2007 |
| WO | WO-2007147074 A2 | 12/2007 |
| WO | WO-2007147076 A2 | 12/2007 |
| WO | WO-2008024473 A2 | 2/2008 |
| WO | WO-2008048931 A1 | 4/2008 |
| WO | WO-2008051928 A2 | 5/2008 |
| WO | WO-2008059578 A1 | 5/2008 |
| WO | WO-2008081451 A2 | 7/2008 |
| WO | WO-2008115497 A2 | 9/2008 |
| WO | WO-2008135837 A2 | 11/2008 |
| WO | WO-2008157264 A2 | 12/2008 |
| WO | WO-2009009769 A2 | 1/2009 |
| WO | WO-2009013492 A1 | 1/2009 |
| WO | WO-2009013496 A1 | 1/2009 |
| WO | WO-2009019215 A1 | 2/2009 |
| WO | WO-2009019455 A2 | 2/2009 |
| WO | WO-2009030100 A1 | 3/2009 |
| WO | WO-2009032779 A2 | 3/2009 |
| WO | WO-2009032781 A2 | 3/2009 |
| WO | WO-2009033178 A1 | 3/2009 |
| WO | WO-2009036525 A2 | 3/2009 |
| WO | WO-2009091934 A1 | 7/2009 |
| WO | WO-2009092035 A2 | 7/2009 |
| WO | WO-2009105531 A1 | 8/2009 |
| WO | WO-2009146335 A1 | 12/2009 |
| WO | WO-2010017214 A1 | 2/2010 |
| WO | 2010/033652 A1 | 3/2010 |
| WO | WO-2010075459 A1 | 7/2010 |
| WO | WO-2011041485 A1 | 4/2011 |
| WO | WO-2011057094 A1 | 5/2011 |
| WO | WO-2011087760 A2 | 7/2011 |
| WO | WO-2011090556 A1 | 7/2011 |
| WO | 2011/118603 | 9/2011 |
| WO | WO-2011146632 A1 | 11/2011 |
| WO | WO-2012071621 A1 | 6/2012 |
| WO | WO-2012083250 A2 | 6/2012 |
| WO | WO-2012088456 A2 | 6/2012 |
| WO | WO-2012108920 A1 | 8/2012 |
| WO | WO-2012142531 A2 | 10/2012 |
| WO | 2007/149791 A2 | 12/2012 |
| WO | WO-2013030577 A1 | 3/2013 |
| WO | 2013/045432 A1 | 4/2013 |
| WO | WO-2013052557 A2 | 4/2013 |
| WO | WO-2013078470 A2 | 5/2013 |
| WO | WO-2013086464 A1 | 6/2013 |
| WO | WO-2013130848 A1 | 9/2013 |
| WO | 2013/181651 A1 | 12/2013 |
| WO | WO-2014004726 A1 | 1/2014 |
| WO | WO-2014014497 A1 | 1/2014 |
| WO | WO-2014018080 A1 | 1/2014 |
| WO | 2014/035986 A1 | 3/2014 |
| WO | 2014/122288 A1 | 8/2014 |
| WO | WO-2014149134 A2 | 9/2014 |
| WO | WO-2014151117 A1 | 9/2014 |
| WO | 2015035177 A1 | 3/2015 |
| WO | 2015/070086 A1 | 5/2015 |
| WO | WO-2015100427 A1 | 7/2015 |
| WO | 2015138997 A1 | 9/2015 |
| WO | WO-2015164432 A1 | 10/2015 |
| WO | 2016/009059 A1 | 1/2016 |
| WO | 2016/065295 A1 | 4/2016 |
| WO | WO-2016138080 A1 | 9/2016 |
| WO | 2016/193490 A1 | 12/2016 |
| WO | 2017-045654 A1 | 3/2017 |
| WO | WO-2017058784 A1 | 4/2017 |
| WO | WO-2018083467 A1 | 5/2018 |
| WO | WO-2018106798 A1 | 6/2018 |
| WO | 2018/156418 A1 | 8/2018 |
| WO | 2019/161244 A1 | 8/2019 |
| WO | 2020104670 A1 | 5/2020 |
| WO | WO-2020131699 A2 | 6/2020 |

OTHER PUBLICATIONS

Ahmadian, A. et al., "Analysis of the p53 Tumor Suppressor Gene by Pyrosequencing", BioTechniques, vol. 28, Jan. 2000, 140-147.

Benesova, et al., "Mutation-based detection and monitoring of cell-free tumor DNA in peripheral blood of cancer patients", Analytical Biochemistry, vol. 433, 2013, 227-234.

Birkenkamp-Demtroder, et al., "Longitudinal assessment of multiplex patient-specific ctDNA biomarkers in bladder cancer for diagnosis, surveillance and recurrence", Annals of Oncology, Oxford University Press NLD, vol. 29, No. Supplement 8, 2018, viii26.

Bolotin, D. A. et al., "MiXCR: software for comprehensive adaptive immunity profiling", Nature, vol. 12, No. 5, May 2015, 380-381.

Brochet, X. et al., "IMGT/V-QUEST: the highly customized and integrated system for IG and TR standardized V-J and V-D-J sequence analysis", Nucleic Acids Research, vol. 36, May 23, 2008, W503-W508.

Bunnapradist, S. et al., "Using both the fraction and Quantity of Donor-Derived Cell-free DNA to Detect Kidney Allograft Rejection", JASN, vol. 32, 2021, 2439-2441.

Burnham, P. et al., "Single-stranded DNA library preparation uncovers the origin and diversity of ultrashort cell-free DNA in plasma", Scientific Reports, vol. 6, No. 27859, Jun. 14, 2016, 9 pages.

(56) References Cited

OTHER PUBLICATIONS

Cawkwell, L. et al., "Rapid detection of allele loss in colorectal tumours using microsatellites and fluorescent DNA technology", Br. J. Cancer, vol. 67, 1993, 1262-1267.
Chang, et al., "Identification of individual DNA molecule of *Mycobacterium tuberculosis* by nested PCR-RLFP and capillary electrophoresis", National Library of Medicine, 2008, 182-8.
Chen, et al., "Non-invasive prenatal diagnosis using fetal DNA in maternal plasma: a preliminary study for identification of paternally-inherited alleles using single nucleotide polymorphisms", BMJ Open, 5(7), 2015, 1-8.
Chothia, C. et al., "Canonical structures for the hypervariable regions of immunoglobulins", Journal of Molecular Biology, vol. 196, No. 4, Aug. 20, 1987, 901-917.
Chun, et al., "Dual priming oligonucleotide system for the multiplex detection of respiratory viruses and SNP genotyping of CYP2C19 gene", Nucleic Acids Research, vol. 35, No. 6, 2007, 1-6.
Costa, J.-M. et al., "Fetal RHD genotyping in maternal serum during the first trimester of pregnancy", British Journal of Haematology, vol. 119, 2002, 255-260.
Croft, Jr., Daniel et al., "Performance of Whole-Genome Amplified DNA Isolated from Serum and Plasma on High-Density Single Nucleotide Polymorphism Arrays", Journal of Molecular Diagnostics, 10(3), 2008, 249-257.
Daniels, G. et al., "Fetal blood group genotyping from DNA from maternal plasma: an important advance in the management and prevention of haemolytic disease of the fetus and newborn", Vox Sanguinis, vol. 87, 2004, 223-232.
Deusen, et al., "Comprehensive Detection of Driver Mutations in Acute Myeloid Leukemia Including Internal Tandem Duplications with Anchored Multiplex PCR and Next-Generation Sequencing", Blood, vol. 128, No. 22, 2016, 5251.
Diaz, et al., "Liquid Biopsies: Genotyping Circulating Tumor DNA", Journal of Clinical Oncology, vol. 32, No. 6, 2014, 579-586.
Diehl, et al., "Detection and quantification of mutations in the plasma of patients with colorectal tumors", Proceedings of the National Academy of Sciences, vol. 102, 2005, 16368-16373.
Ehlayel, A. et al., "Emerging monitoring technologies in kidney transplantation", Pediatric Nephrology, vol. 36, 2021, 3077-3087.
Findlay, I. et al., "Allelic drop-out and preferential amplification in single cells and human blastomeres: implications for preimplantation diagnosis of sex and cystic fibrosis", Molecular Human Reproduction, vol. 1, 1995, 1609-1618.
Fire, et al., "Rolling replication of short DNA circles", PNAS, 1995, 4641-4645.
Ge, et al., "Haplotype block: a new type of forensic DNA markers", Int J Legal Med, 2010, 353-361.
Glaab, W. E. et al., "A novel assay for allelic discrimination that combines the fluorogenic 5' nuclease polymerase chain reaction (TaqMan) and mismatch amplification mutation assay", Mutation Research, vol. 430, 1999, 12 pgs.
Goessl, C. et al., "DNA Alterations in Body Fluids as Molecular Tumor Markers for Urological Malignancies", European Urology, vol. 41, 2002, 668-676.
Grenda, R., "Torque teno (TTV) viral load as a biomarker of immunosuppressive strength after kidney transplantation in children", Pediatric Nephrology, vol. 36, May 27, 2020, 3 pages.
Gusella, J. et al., "Precise localization of human B-globin gene complex on chromosome 11*", Proc. Natl. Acad. Sci USA, vol. 76, No. 10, Oct. 1979, 5239-5243.
Hainer & Fazzio, "High-Resolution Chromatin Profiling Using CUT&RUN", Current Protocols in Molecular Biology, 2019, 1-22.
Hiendleder, et al., "Functional genomics: tools for improving farm animal health and welfare", Rev. Sci. Tech. Off. Int. Epiz., 24 (1), 2005, 354-377.
Illumina, "HumanOmni1-Quad BeadChip", Illumina DNA Analysis, Pub. No. 370-21009-007, 2009, 1 page.
Illumina, "HumanOmni2.5-8 BeadChips: Next-Generation GWAS Content for Genotyping and CNV Analysis", Data Sheet: DNA Analysis, Pub. No. 370-2011-008, 2011, 1 page.
Illumina, "Illumina Adapter Sequences", Published by Illumina, 2018, 1-45.
Jordens, et al., "Amplification with molecular beacon primers and reverse line blotting for the detection and typing of human papillomaviruses", Journal of Virological Methods, vol. 89, 2000, 29-37.
Jung, Klaus et al., "Increased cell-free DNA in plasma of patients with metastatic spread in prostate cancer", Cancer Letters, 2004, 173-180.
Kaboev, et al., "PCR hot start using primers with the structure of molecular beacons (hairpin-like structure)", Nucleic Acids Research, vol. 28, 2000, 1-2.
Kane, et al., "Application of less primer method to PCR", DNA Polymorphism, 2004, vol. 13, pp. 34-37.
Keshavjee, S. H. et al., "The role of dextran 40 and potassium in extended hypothermic lung preservation for transplantation", The Journal of Thoracic and Cardiovascular Surgery, vol. 103, No. 2, 1992.
Kirsch-Gerweck, et al., "HaploBlocks: Efficient Detection of Positive Selection in Large Population Genomic Datasets", Mol. Biol. Evol., 2023, 12 pages.
Kittler, R. et al., "A Whole Genome Amplification Method to Generate Long Fragments from Low Quantities of Genomic DNA", Analytical Biochemistry, vol. 300, 2002, 237-244.
Koeppe, et al., "HIV-1-Specific CD4+ T-Cell Responses Are Not Associated With Significant Viral Epitope Variation in Persons With Persistent Plasma Viremia", J Acquir Immune Defic Syndr, 2006, 41:140-148.
Ku, et al., "Exome versus transcriptome sequencing in identifying coding region variants", Expert Review of Molecular Diagnostics, vol. 12, 2012, 241-251.
Kulifaj, D. et al., "Development of a standardized real time PCR for Torque teno viruses (TTV) viral load detection and quantification: A new tool for immune monitoring", Journal of Clinical Virology, vol. 105, 2018, 118-127.
Lajoie, B. R. et al., "The Hitchhiker's Guide to Hi-C Analysis: Practical guidelines", Methods: Author manuscript, vol. 72, Jan. 2015, 65-75.
Landegren, U. et al., "Reading Bits of Genetic Information: Methods for Single-Nucleotide Polymorphism Analysis", Genome Research, vol. 8, No. 8, 769-776, 1997.
Lizardi, et al., "Mutation detection and single-molecule counting using isothermal rolling-circle amplification", Nature Genetics, 1998, 225-232.
Lo, Y.M. D. et al., "Prenatal Diagnosis of Fetal RhD Status by Molecular Analysis of Maternal Plasma", The New England Journal of Medicine, vol. 339, No. 24, 1998, 1734-1738.
Mamun, et al., "The *Escherichia coli* UVM response is accompanied by an SOS-independent error-prone DNA replication activity demonstrable in vitro", Molecular Microbiology, 2000, 368-380.
Margulies, et al., "Genome Sequencing in Open Microfabricated High Density Picoliter Reactors", Nature, 437(7057), 2005, 376-380.
Marusyk, et al., "Causes and consequences", Biochimica et Biophysica Acta, vol. 1805, 2010, 105-117.
Metzker, Michael, Declaration of Michael L. Metzker, Ph.D. from IPR2018-01317, 2004, 118 pages.
Mueller, P. R. et al., "In Vivo Footprinting of a Muscle Specific Enhancer by Ligation Mediated PCR", Science, vol. 249, Nov. 10, 1989, 780-786.
Namlos, H.M. et al., "Use of liquid biopsies to monitor disease progression in a sarcoma patient: a case report", BMC Cancer, vol. 17, No. 1, 2017, 2-3.
Nelson, C. M. et al., "Whole genome transcription profiling of Anaplasma phagocytohilum in human and tick host cells by tiling array analysis", BMC Genomics, vol. 9, No. 364, Jul. 31, 2008, 16 pgs.
Ohya, K. et al., "Detection of the CTG Repeat Expansion in Congenital Myotonic Dystrophy", Jpn J. Human Genet, vol. 42, 1997, 169-180.
Raemdonck, Dirk Van et al., "Ex-vivo lung perfusion", Transplant International, vol. 28, Issue 6, Special Issue: Focus Issue: Machine Perfusion, 2014, 643-656.

(56) References Cited

OTHER PUBLICATIONS

Rechitsky, S. et al., "Allele Dropout in Polar Bodies and Blastomeres", Journal of Assisted Reproduction and Genetics, vol. 15, No. 5, 1998, 253-257.
Schutz, E. et al., "Graft-derived cell-free DNA, a noninvasive early rejection and graft damage marker in liver transplantation: A prospective, observational, multicenter cohort study", PLOS Medicine, vol. 14, No. 4, Apr. 25, 2017, 19 pgs.
Selzner, Markus et al., "Normothermic Ex Vivo Liver Perfusion Using Steen Solution as Perfusate for Human Liver Transplantation: First North American Results", Liver Transplantation, vol. 22, Issue 11, 2016.
Sethi, Himanshu et al., "Analytical validation of the Signatera (TM) RUO assay, a highly sensitive patient-specific multiplex PCR NGS-based noninvasive cancer recurrence detection and therapy monitoring assay", Cancer Research, vol. 78, No. 13, 2018, 4542.
Stone, J. P. et al., "Altered Immunogenicity of Donor Lungs via Removal of Passenger Leukocytes Using Ex Vivo Lung Perfusion", American Journal of Transplantation, vol. 16, 2016, 33-43.
Tie, et al., "Circulating tumor DNA as an early marker of therapeutic response in patients with metastatic colorectal cancer", Annals of Oncology, vol. 26, No. 8, 2015, 1715-1722.
Toth, T. et al., "Prenatal Detection of Trisomy 13 From Amniotic Fluid by Quantitative Fluorescent Polymerase Chain Reaction", Prenatal Diagnosis, vol. 18, 1998, 669-674.
Tungwiwat, et al., "Non-invasive fetal sex determination using a conventional nested PCR analysis of fetal DNA in maternal plasma", Clinica Chimica Acta, vol. 334, No. 1-2, 2003, 173-177.
Valenza, F. et al., "The Consumption of Glucose During Ex Vivo Lung Perfusion Correlates with Lung Edema", Transplantation Proceedings, vol. 43, 2011, 993-996.
Ventura-Aguiar, P. et al., "Donor-derived Cell-free DNA Shows High Sensitivity for the Diagnosis of Pancreas Graft Rejection in Simultaneous Pancreas-Kidney Transplantation", Transplantation, vol. 00, No. 00, 2022, 8 pages.
Volckmar, et al., "A field guide for cancer diagnostics using cell-free DNA: From principles to practice and clinical applications", Genes Chromosomes Cancer, 2018, 123-139.
Wagner, F. F. et al., "RHD gene deletion occurred in the Rhesus box", Blood, vol. 95, No. 12, 2000, 3662-3668.
Wang, et al., "DNA Degradation Test Predicts Success in Whole-Genome Amplification from Diverse Clinical Samples", Journal of Molecular Diagnostics, vol. 9, 2007, 441-451.
Wangkumhang, P. et al., "WASP: a Web-based Allele-Specific PCR assay designing tool for detecting SNPs and mutations", BMC Genomics, vol. 8, No. 275, Aug. 14, 2007, 9 pgs.
Whitlam, J. B. et al., "Diagnostic application of kidney allograft-derived absolute cell-free DNA levels during transplant dysfunction", Am J Transplant, vol. 19, 2019, 1037-1049.
Wong, I. H. et al., "Quantitative Analysis of Tumor-derived Methylated p16INK4a Sequences in Plasma, Serum, and Blood Cells of Hepatocellular Carcinoma Patients", Clinical Cancer Research, vol. 9, Mar. 2003, 1047-1052.
Ye, et al., "Primer-BLAST: a tool to design target-specific primers for polymerase chain reaction", BMC Bioinformatics, 13:134, 2012, 11 pages.
Abbosh C., et al., "Phylogenetic ctDNA Analysis Depicts Early-stage Lung Cancer Evolution," Nature, May 25, 2017, vol. 545, No. 7655, pp. 446-451 (21 Pages), Apr. 26, 2017, XP055409582, ISSN: 0028-0836, DOI: 10.1038/nature22364, the Whole Document.
Abidi S.S.R., et al., "Leveraging XML-based Electronic Medical Records to Extract Experiential Clinical Knowledge: An Automated Approach to Generate Cases for Medical Case-based Reasoning Systems," International Journal of Medical Informatics, 2002, vol. 68, No. 1-3, pp. 187-203.
Agarwal A., et al., "Commercial Landscape of Noninvasive Prenatal Testing in the United States," Prenatal Diagnosis, 2013, vol. 33, pp. 521-531.

Alaeddini R., et al., "Forensic Implications of Genetic Analyses from Degraded DNA—A Review," Forensic Science International: Genetics, 2010, vol. 4, pp. 148-157.
Alkan C., et al., "Personalized Copy Number and Segmental Duplication Maps Using Next-Generation Sequencing," Nature Genetics, Oct. 2009, vol. 41, No. 10, pp. 1061-1068.
Allaire F.R., "Mate Selection by Selection Index Theory," Theoretical Applied Genetics, 1980, vol. 57, No. 6, pp. 267-272.
Allawi H.T., et al., "Thermodynamics of Internal C-T Mismatches in DNA," Nucleic Acids Research, 1998, vol. 26, No. 11, pp. 2694-2701.
Anker P., et al., "The Second International Symposium on Circulating Nucleic Acids in Plasma and Serum (CNAPS-2) held in Conjunction with the 6th Annual Scientific Symposium of the Hong Kong Cancer Institute", Clinical Chemistry, Hong Kong, Feb. 20-21, 2001, vol. 47, No. 2, pp. 361-370.
Aoki Y., "Statistical and Probabilistic Bases of Forensic DNA Testing," The Journal of the Iwate Medical Association, 2002, vol. 54, pp. 81-94 (18 Pages).
Ashoor G., et al., "Chromosome-selective Sequencing of Maternal Plasma Cell-free DNA for First-trimester Detection of Trisomy 21 and Trisomy 18," American Journal of Obstetrics & Gynecology, Apr. 2012, vol. 206, pp. 322.e1-322.e5.
Ashoor G., et al., "Fetal Fraction in Maternal Plasma Cell-Free DNA at 11-13 Weeks' Gestation: Effect of Maternal and Fetal Factors," Fetal Diagnosis and Therapy, 2012, pp. 1-7, Published Online May 4, 2012.
Ashoor G., et al., "Fetal Fraction in Maternal Plasma Cell-free DNA at 11-13 Weeks' Gestation: Relation to Maternal and Fetal Characteristics," Ultrasound in Obstetrics and Gynecology, 2013, vol. 41, pp. 26-32.
Bada M.A., et al., "Computational Modeling of Structural Experimental Data", Methods in Enzymology, 2000, vol. 317, pp. 470-491, (23 Pages).
Beaumont M.A., et al., "The Bayesian Revolution in Genetics," Nature Reviews, Genetics, Apr. 2004, vol. 5, pp. 251-261.
Beck J., et al., "Profile of the Circulating DNA in Apparently Healthy Individuals," Clinical Chemistry, 2009, vol. 55, No. 4, pp. 730-738.
Beer A.E., et al., "The Biological Basis of Passage of Fetal Cellular Material Into the Maternal Circulation," Annals New York Academy of Sciences, 1994, vol. 731, pp. 21-35.
Beerenwinkel N., et al., "Geno2pheno: Estimating Phenotypic Drug Resistance from HIV-1 Genotypes," Nucleic Acids Research, 2003, vol. 31, No. 13, pp. 3850-3855.
Beerenwinkel N., et al., "Methods for Optimizing Antiviral Combination Therapies," Bioinformatics, 2003, vol. 19, Supplement. 1, pp. i16-i25.
Benn P., et al., "Non-Invasive Prenatal Diagnosis for Down Syndrome: The Paradigm Will Shift, but Slowly," Ultrasound in Obstetrics & Gynecology, 2012, vol. 39, pp. 127-130.
Benn P., et al., "Non-Invasive Prenatal Testing for Aneuploidy: Current Status and Future Prospects," Ultrasound in Obstetrics & Gynecology, 2013, vol. 42, pp. 15-33.
Bentley D.R., et al., "Accurate Whole Human Genome Sequencing Using Reversible Terminator Chemistry," Nature, Nov. 6, 2008, vol. 456, No. 7218, pp. 53-59 (20 Pages).
Bermudez M., et al., "Single-Cell Sequencing and Mini-Sequencing for Preimplantation Genetic Diagnosis," Prenatal Diagnosis, 2003, vol. 23, pp. 669-677.
Bevinetto G., "5 Foods All Pregnant Women Need," American Baby, 8 Pages, [Retrieved on Apr. 15, 2008], Retrieved from URL: http://www.parents.com/pregnancy/mybody/nutrition/5greatpregnancyfoods/.
Bianchi D.W., "Circulating Fetal DNA: Its Origin and Diagnostic Potential—A Review," Placenta, May 2004, vol. 25, vol. 18, Supplemental A, S93-S101.
Bianchi D.W., et al., "Genome-Wide Fetal Aneuploidy Detection by Maternal Plasma DNA Sequencing," Obstetrics & Gynecology, May 2012, vol. 119, No. 5. pp. 890-901.
Bianchi D.W., et al., "Insights into Fetal and Neonatal Development Through Analysis of Cell-Free RNA in Body Fluids," Early Human Development, Nov. 2010, vol. 86, No. 11, pp. 747-752, 11 Pages.

(56) References Cited

OTHER PUBLICATIONS

Bianchi D.W., "Review: Fetal Cells in the Maternal Circulation: Feasibility for Prenatal Diagnosis," British Journal of Haematology, 1999, vol. 105, pp. 574-583.
Birch L., et al., "Accurate and Robust Quantification of Circulating Fetal and Total DNA in Maternal Plasma from 5 to 41 Weeks of Gestation," Clinical Chemistry, 2005, vol. 51, No. 2, pp. 312-320.
Bisignano A., et al., "PGD and Aneuploidy Screening for 24 Chromosomes: Advantages and Disadvantages of Competing Platforms," Reproductive BioMedicine Online, 2011, vol. 23, pp. 677-685.
Bodenreider O., "The Unified Medical Language System (UMLS): Integrating Biomedical Terminology," Nucleic Acids Research, 2004, vol. 32, (Database issue), pp. D267-D270.
Breithaupt H., "The Future of Medicine," European Molecular Biology Organisation, 2001, vol. 2, No. 6, pp. 465-467.
Brownie J., et al., "The Elimination of Primer-Dimer Accumulation in PCR," Nucleic Acids Research, 1997, vol. 25, No. 16, pp. 3235-3241.
Burkey B.F., et al., "Hepatic Apolipoprotein J is Secreted as a Lipoprotein," Journal of Lipid Research, 1992, vol. 33, pp. 1517-1526.
Butler J.M., et al., "The Development of Reduced Size STR Amplicons as Tools for Analysis of Degraded DNA," Journal of Forensic Sciences, Sep. 2003, vol. 48, No. 5, pp. 1054-1064.
Cairns P., et al., "Homozygous Deletions of 9p21 in Primary Human Bladder Tumors Detected by Comparative Multiplex Polymerase Chain Reaction," Cancer Research, Mar. 15, 1994, vol. 54, pp. 1422-1424 (4 Pages).
Caliendo A.M., "Multiplex PCR and Emerging Technologies for the Detection of Respiratory Pathogens," Clinical Infectious Diseases, 2011, vol. 52, Supp. 4, pp. S326-S330.
Cansar: "Hs-578-T-Breast-Copy Number Variation-Chromosome 8-Cell Line Synopsis," ICR Cancer Research, UK, 50 Pages, [Retrieved on Mar. 26, 2018], Retrieved from URL: https://cansar.icr.ac.uk/cansar/cell-lines/Hs-578-Vcopy_number_variation/chromosome_8/.
Carnevale A., et al., "Attitudes of Mexican Geneticists Towards Prenatal Diagnosis and Selective Abortion," American Journal of Medical Genetics, 1998, vol. 75, pp. 426-431.
Carvalho B., et al., "Exploration, Normalization, and Genotype Calls of High-density Oligonucleotide SNP Array Data," Biostatistics, 2007, vol. 8, No. 2, pp. 485-499.
Casbon J.A., et al., "A Method for Counting PCR Template Molecules with Application to Next-generation Sequencing," Nucleic Acids Research, Apr. 13, 2011, vol. 39, No. 12, pp. 1-8.
Chakraborty R., et al., "Paternity Exclusion by DNA Markers: Effects of Paternal Mutations," Journal of Forensic Sciences, Jul. 1996, vol. 41, No. 4, pp. 671-677.
Chan K.C.A., et al., "Size Distributions of Maternal and Fetal DNA in Maternal Plasma," Clinical Chemistry, 2004, vol. 50, No. 1, pp. 88-92.
Chang H-W., et al., "Assessment of Plasma DNA Levels, Allelic Imbalance, and CA 125 as Diagnostic Tests for Cancer," Journal of the National Cancer Institute, Nov. 20, 2002, vol. 94, No. 22, pp. 1697-1703.
Chen E.Z., et al., "Noninvasive Prenatal Diagnosis of Fetal Trisomy 18 and Trisomy 13 by Maternal Plasma DNA Sequencing," PLoS ONE, Jul. 6, 2011, vol. 6, Issue 7, e21791, pp. 1-7.
Chen X.Q., et al., "Microsatellite Alterations in Plasma DNA of Small Cell Lung Cancer Patients," Nature Medicine, Sep. 1996, vol. 2, No. 9, pp. 1033-1035.
Chetty S., et al., "Uptake of Noninvasive Prenatal Testing (NIPT) in Women Following Positive Aneuploidy Screening," Prenatal Diagnosis, 2013, vol. 33, pp. 542-546.
Chiu R.W.K., et al., "Effects of Blood-Processing Protocols on Fetal and Total DNA Quantification in Maternal Plasma," Clinical Chemistry, Sep. 2001, vol. 47, No. 9, pp. 1607-1613, PubMed PMID: 11514393.
Chiu R.W.K., et al., "Maternal Plasma DNA Analysis With Massively Parallel Sequencing by Litigation for Noninvasive Prenatal Diagnosis of Trisomy 21," Clinical Chemistry, 2010, vol. 56, No. 3, pp. 459-463.
Chiu R.W.K., et al., "Non-Invasive Prenatal Assessment of Trisomy 21 by Multiplexed Maternal Plasma DNA Sequencing: Large Scale Validity Study," BMJ, 2011, vol. 342, c7401, 9 Pages.
Chiu R.W.K., et al., "Non-Invasive Prenatal Diagnosis by Single Molecule Counting Technologies," Trends in Genetics, 2009, vol. 25, No. 7, pp. 324-331.
Chiu R.W.K., et al., "Noninvasive Prenatal Diagnosis of Fetal Chromosomal Aneuploidy by Massively Parallel Genomic Sequencing of DNA in Maternal Plasma (With Supporting Information)," Proceedings of the National Academy of Sciences, Dec. 23, 2008, vol. 105, No. 51, 23 Pages.
Choi M., et al., "Genetic Diagnosis by Whole Exome Capture and Massively Parallel DNA Sequencing," Proceedings of the National Academy of Sciences, Nov. 10, 2009, vol. 106, No. 45, pp. 19096-19101.
Chu T., et al., "A Novel Approach Toward the Challenge of Accurately Quantifying Fetal DNA in Maternal Plasma," Prenatal Diagnosis, Nov. 11, 2010, vol. 30, pp. 1226-1229.
Chu T., et al., "Statistical Considerations for Digital Approaches to Non-Invasive Fetal Genotyping," Bioinformatics, Advance Access publication Sep. 23, 2010, vol. 26, No. 22, pp. 2863-2866.
Chu T., et al., "Statistical Model for Whole Genome Sequencing and its Application to Minimally Invasive Diagnosis of Fetal Genetic Disease," Bioinformatics, Advance Access Publication Mar. 23, 2009, vol. 25, No. 10, pp. 1244-1250.
Cole N.W., et al., "Hyperglycemia-Induced Membrane Lipid Peroxidation and Elevated Homocysteine Levels Are Poorly Attenuated by Exogenous Folate in Embryonic Chick Brains," Comparative Biochemistry and Physiology, Part B, 2008, vol. 150, pp. 338-343.
Colella S., et al., "QuantiSNP: an Objectives Bayes Hidden-Markov Model to Detect and Accurately Map Copy Number Variation Using SNP Genotyping Data," Nucleic Acids Research, 2007, vol. 35, No. 6, pp. 2013-2025.
Cossu G., et al., "Rh D/d Genotyping by Quantitative Polymerase Chain Reaction and Capillary Zone Electrophoresis," Electrophoresis, 1996, vol. 17, pp. 1911-1915.
Coyle J.F., et al., "Standards for Detailed Clinical Models as the Basis for Medical Data Exchange and Decision Support," International Journal of Medical Informatics, 2003, vol. 69, No. (2-3), pp. 157-174.
Craig D.W., et al., "Identification of Genetic Variants using Bar-Coded Multiplexed Sequencing," Nature Methods, Oct. 2008, vol. 5, No. 10, pp. 887-893.
Cross J., et al., "Resolution of Trisomic Mosaicism in Prenatal Diagnosis: Estimated Performance of a 50k SNP Microarray," Prenatal Diagnosis, 2007, vol. 27, pp. 1197-1204.
D'Aquila R.T., et al., "Maximizing Sensitivity and Specificity of PCR by Pre-amplification Heating," Nucleic Acids Research, 1991, vol. 19, No. 13, p. 3749.
Daruwala R-S., et al., "A Versatile Statistical Analysis Algorithm to Detect Genome Copy Number Variation," Proceedings of the National Academy of Sciences, Nov. 16, 2004, vol. 101, No. 46, p. 16292-16297.
De Bruin E.C., et al., "Spatial and Temporal Diversity in Genomic Instability Processes Defines Lung Cancer Evolution," Science, Oct. 10, 2014, vol. 346, No. 6206, pp. 251-256 (12 Pages).
De Vries B.B.A., et al., "Diagnostic Genome Profiling in Mental Retardation," American Journal of Human Genetics, 2005, vol. 77, pp. 606-616, Published Online Aug. 30, 2005.
Deangelis M.M., et al., "Solid-phase Reversible Immobilization for the Isolation of PCR Products," Nucleic Acids Research, 1995, vol. 23, No. 22, pp. 4742-4743.
Declaration under 37 C.F.R. & 1.132 by Dr. Zimmerman B., for U.S. Appl. No. 14/044,434, filed Oct. 30, 2014, 4 Pages.
Deutsch S., et al., "Detection of Aneuploidies by Paralogous Sequence Quantification," Journal of Medical Genetics, 2004, vol. 41, pp. 908-915.

(56) References Cited

OTHER PUBLICATIONS

Devaney S.A., et al., "Noninvasive Fetal Sex Determination Using Cell-free Fetal DNA: A Systematic Review and Meta-analysis," JAMA, Aug. 10, 2011, vol. 306, No. 6, pp. 627-636.

Dhallan R., et al., "A Non-Invasive Test for Prenatal Diagnosis Based on Fetal DNA Present in Maternal Blood: A Preliminary Study," Lancet, Feb. 10, 2007, vol. 369, No. 9560, pp. 474-481.

Dhallan R., et al., "Methods to Increase the Percentage of Free Fetal DNA Recovered From the Maternal Circulation," JAMA, Mar. 3, 2004, vol. 291, No. 9, pp. 1114-1119.

Dieffenbach C.W., et al., "General Concepts for PCR Primer Design," Genome Research, PCR methods and Applications, 1993, vol. 3, pp. S30-S37 (9 Pages).

Ding C., et al., "Direct Molecular Haplotyping of Long-range Genomic DNA With M1-PCR," Proceedings of the National Academy of Sciences, Jun. 24, 2003, vol. 100, No. 13, pp. 7449-7453.

Dodge Y., "The Concise Encyclopedia of Statistics," Bayes' Theorem, 2008, pp. 30-31 (4 Pages).

Dohm J.C., et al., "Substantial Biases in Ultra-Short Read Data Sets From High-Throughput DNA Sequencing," Nucleic Acids Research, 2008, vol. 36, No. 16, e105, 10 Pages.

Dolganov G.M., et al., "A Novel Method of Gene Transcript Profiling in Airway Biopsy Homogenates Reveals Increased Expression of a Na+—K+—Cl-Cotransporter (NKCC1) in Asthmatic Subjects," Genome Research, 2001, vol. 11, pp. 1473-1483 (12 Pages).

Dong-Ling T., et al., "Multiplex Fluorescent PCR for Noninvasive Prenatal Detection of Fetal-derived Paternally Inherited Diseases Using Circulatory Fetal DNA in Maternal Plasma," European Journal of Obstetrics & Gynecology and Reproductive Biology, 2009, vol. 144, No. 9, pp. 35-39.

Donohoe G.G., et al., "Rapid Single-tube Screening of the C282y Hemochromatosis Mutation by Real-time Multiplex Allele-specific PCR Without Fluorescent Probes," Clinical Chemistry, 2000, vol. 46, No. 10, pp. 1540-1547 (13 Pages).

Donoso P., et al., "Current Value of Preimplantation Genetic Aneuploidy Screening in IVF," Human Reproduction Update, 2007, vol. 13, No. 1, pp. 15-25.

Echeverri D., et al., "Caffeine's Vascular Mechanisms of Action," International Journal of Vascular Medicine, Aug. 25, 2010, vol. 2010, Article ID. 834060, 11 Pages.

Ehrich M., et al., "Noninvasive Detection of Fetal Trisomy 21 by Sequencing of DNA in Maternal Blood: A Study in a Clinical Setting," American Journal of Obstetrics & Gynecology, Mar. 2011, vol. 204, pp. 205.e1-205.e11.

Eichler H., et al., "Mild Course of Fetal Rh D Haemolytic Disease Due to Maternal Alloimmunisation to Paternal HLA Class I and II Antigens," Vox Sang, 1995, vol. 68, pp. 243-247.

Ellison A.M., "Bayesian Inference in Ecology," Ecology Letters, Jun. 2004, vol. 7, No. 6, pp. 509-520, 13 Pages.

Ellonen P., et al., "Development of SNP Microarray for Supplementary Paternity Testing," International Congress Series, 2004, vol. 1261, pp. 12-14.

European Communication pursuant to Article 94(3) EPC and Examination Report for European Application No. EP08742125.1, mailed Feb. 12, 2010, 5 Pages.

European Search Report for European Application No. 014198110, mailed Apr. 28, 2015, 3 Pages.

Extended European Search Report for European Application No. 06838311.6, mailed Dec. 30, 2008, 8 Pages.

Fan C.H., et al., "Non-Invasive Prenatal Measurement of the Fetal Genome," Nature, 2012, 26 Pages, DOI: 10.1038/nature11251.

Fan H.C., et al., "Sensitivity of Noninvasive Prenatal Detection of Fetal Aneuploidy from Maternal Plasma Using Shotgun Sequencing is Limited only by Counting Statistics," PLoS One, Mar. 2010, vol. 5, Issue 5 (e10439), pp. 1-6 (7 Pages), Published May 3, 2010.

Fan H.C., et al., "Microfluidic Digital PCR Enables Rapid Prenatal Diagnosis of Fetal Aneuploidy," American Journal of Obstetrics & Gynecology, May 2009, vol. 200, pp. 543e1-543e7.

Fan H.C., et al., "Whole-genome Molecular Haplotyping of Single Cells," Nature Biotechnology, Jan. 1, 2011, vol. 29, No. 1, pp. 51-57 (9 Pages).

Fan H.C., "Noninvasive Diagnosis of Fetal Aneuploidy by Shotgun Sequencing DNA from Maternal Blood," Proceedings of the National Academy of Sciences, USA, Oct. 21, 2008, vol. 105, No. 42, pp. 16266-16271, DOI: 10.1073/pnas.0808319105 Published Online (Oct. 6, 2008).

Fan J-B., et al., "Highly Parallel Genomic Assays," Nature Reviews, Aug. 2006, vol. 7, pp. 632-644.

Fazio G., et al., "Identification of RAPD Markers Linked to Fusarium Crown and Root Rot Resistance (Frl) in Tomato," Euphytica, 1999, vol. 105, pp. 205-210.

Fiorentino F., et al., "Development and Clinical Application of a Strategy for Preimplantation Genetic Diagnosis of Single Gene Disorders Combined with HLA Matching," Molecular Human Reproduction, Advance Access Publication Mar. 25, 2004, vol. 10, No. 6, pp. 445-460.

Fiorentino F., et al., "Short Tandem Repeats Haplotyping of the HLA Region in Preimplantation HLA Matching," European Journal of Human Genetics, 2005, vol. 13, pp. 953-958 (7 Pages).

Fiorentino F., et al., "Strategies and Clinical Outcome of 250 Cycles of Preimplantation Genetic Diagnosis for Single Gene Disorders," Human Reproduction, 2006, vol. 21, No. 3, pp. 670-684.

"Fixed Medium," Academic Press Dictionary of Science and Technology, Sep. 1992, 1 Page, Accessed on Nov. 18, 2009, Retrieved from URL: www.credoreference.com/entry/apdst/fixedmedium.

Ford E., et al., "A Method for Generating Highly Multiplexed ChIP-seq Libraries," BMC Research Notes, May 22, 2014, vol. 7, No. 312, pp. 1-5 (5 Pages).

Forejt J., et al., "Segmental Trisomy of Mouse Chromosome 17: Introducing an Alternative Model of Down's Syndrome," Comparative and Functional Genomics, 2003, vol. 4, No. 6, pp. 647-652.

Forshew T., et al., "Noninvasive Identification and Monitoring of Cancer Mutations by Targeted Deep Sequencing of Plasma DNA," Science Translational Medicine, May 30, 2012, vol. 4, Issue No. 136 (136ra68) 1-12 (13 Pages).

Fredriksson S., et al., "Multiplex Amplification of All Coding Sequences Within 10 Cancer Genes by Gene-collector," Nucleic Acids Research, 2007, vol. 35, No. 7, Article e47, pp. 1-6.

Freeman J.L., et al., "Copy Number Variation: New Insights in Genome Diversity," Genome Research, 2006, vol. 16, pp. 949-961.

Frost M.S., et al., "Differential Effects of Chronic Pulsatile Versus Chronic Constant Maternal Hyperglycemia on Fetal Pancreatic Beta-Cells," Journal of Pregnancy, 2012, vol. 2012, Article ID 812094, 8 Pages (6 Pages).

Fu G.K., et al., "Counting Individual DNA Molecules by the Stochastic Attachment of Diverse Labels," Proceedings of the National Academy of Sciences, May 31, 2011, vol. 108, No. 22, pp. 9026-9031.

Fu G.K., et al., "Digital Encoding of Cellular mRNAs Enabling Precise and Absolute Gene Expression Measurement by Single-Molecule Counting," Analytical Chemistry, Mar. 3, 2014, vol. 86, pp. 2867-2870.

Ganshirt-Ahlert D., et al., "Fetal DNA in Uterine Vein Blood," Obstetrics & Gynecology, Oct. 1992, vol. 80, No. 4, pp. 601-603.

Ganshirt-Ahlert D., et al., "Ratio of Fetal to Maternal DNA is Less Than 1 in 5000 at Different Gestational Ages in Maternal Blood," Clinical Genetics, Jul. 1990, vol. 38, No. 1, pp. 38-43.

Ganshirt-Ahlert D., et al., "Three Cases of 45,X/46, XYnf Mosaicism," Human Genetics, Jun. 1987, vol. 76, No. 2, pp. 153-156.

Garcia-Murillas I., et al., "Mutation Tracking in Circulating Tumor DNA Predicts Relapse in Early Breast Cancer," Science Translational Medicine, Aug. 2015, vol. 7(302), pp. 1-11.

Gardina P.J., et al., "Ploidy Status and Copy Number Aberrations in Primary Glioblastomas Defined by Integrated Analysis of Allelic Ratios, Signal Ratios and Loss of Heterozygosity Using 500k SNP Mapping Arrays," BMC Genomics, 2008, vol. 9, No. 489, 16 Pages, doi:10.1186/1471-2164-9-489.

Geiss G.K., et al., "Direct Multiplexed Measurement of Gene Expression With Color-coded Probe Pairs," Nature Biotechnology, Feb. 17, 2008, vol. 26, No. 3, pp. 317-325 (10 Pages).

(56) References Cited

OTHER PUBLICATIONS

"Genetics Home Reference, Your Guide to Understanding Genetic Conditions," Genomic Research, 25 Febryary 2014, pp. 1-2 (2 Pages), [Retrieved on Feb. 28, 2014], Retrieved from URL: http://ghr.nlm.nih.gov/handbook/genomicresearch/snp.
Ghanta S., et al., "Non-invasive Prenatal Detection of Trisomy 21using Tandem Single Nucleotide Polymorphisms," PLoS One, Oct. 8, 2010, vol. 5, No. 10:e. 13184, 10 Pages, doi: 10.1371/journal.pone.0013184.
Gjertson D.W., et al., "Assessing Probability of Paternity and the Product Rule in DNA Systems," Genetica, 1995, vol. 96, pp. 89-98.
Greenwalt T.J., et al., "The Quantification of Fetomaternal Hemorrhage by an Enzyme-linked Antibody Test With Glutaraldehyde Fixation," Vox Sang, 1992, vol. 63, pp. 268-271.
Guerra J.C.O., "Terminal Contributions for Duplex Oligonucleotide Thermodynamic Properties in the Context of Nearest Neighbor Models," Biopolymers, 2011, vol. 95, No. 3, pp. 194-201, Published Online Nov. 4, 2010.
Guetta E., et al., "Analysis of Fetal Blood Cells in the Maternal Circulation: Challenges, Ongoing Efforts, and Potential Solutions," Stem Cells and Development, 2004, vol. 13, pp. 93-99.
Guichoux E., et al., "Current Trends in Microsatellite Genotyping," Molecular Ecology Resources, 2011, vol. 11, pp. 591-611.
Gunderson K.J., et al., "A Genome-wide Scalable SNP Genotyping Assay Using Microarray Technology," Nature Genetics, May 2005, vol. 37, No. 5, pp. 549-554.
Hall M.P., "Panorama(TM) Non-Invasive Prenatal Screening for Microdeletion Syndromes," Panaroma Prenatal Screen, Apr. 1, 2014, 5 Pages, XP055157224, [Retrieved on Dec. 8, 2014], Retrieved from URL: http://www.panoramatest.com/sites/default/files/files/PanoramaMicrodeletionsWhitePaper-2.pdf.
Handyside A.H., et al., "Isothermal Whole Genome Amplification From Single and Small Numbers of Cells: a New Era for Preimplantation Genetic Diagnosis of Inherited Disease," 2004, vol. 10, No. 10, pp. 767-772.
Hanjani M.J., et al., "Tracking the Evolution of Non-Small-Cell Lung Cancer," The New England Journal of Medicine, Jun. 1, 2017, vol. 376, No. 22, pp. 2109-2121.
Hara E., et al., "Subtractive cDNA Cloning Using Oligo(dT)30-latex and PCR: Isolation of cDNA Clones Specific to Undifferentiated Human Embryonal Carcinoma Cells," Nucleic Acids Research, 1991, vol. 19, No. 25, pp. 7097-7104.
Hardenbol P., et al., "Highly Multiplexed Molecular Inversion Probe Genotyping: Over 10,000 Targeted SNPs Genotyped in a Singled Tube Assay," Genome Research, 2005, vol. 15, pp. 269-275.
Hardenbol P., et al., "Multiplexed Genotyping with Sequence-Tagged Molecular Inversion Probes," Nature Biotechnology, Jun. 2003, vol. 21, No. 6, pp. 673-678 (7 Pages).
Harismendy O., et al., "Method for Improving Sequence Coverage Uniformity of Targeted Genomic Intervals Amplified by LR-PCR Using Illumina GA Sequencing-by-synthesis Technology," Bio Techniques, 2009, vol. 46, No. 3, pp. 229-231.
Harper J.C., et al., "Recent Advances and Future Developments in PGD," Prenatal Diagnosis, 1999, vol. 19, pp. 1193-1199.
Harton G.L., et al., "Preimplantation Genetic Testing for Marfan Syndrome," Molecular Human Reproduction, 1996, vol. 2 No. 9, pp. 713-715.
Hawkins T.L., et al., "Whole Genome Amplification—Applications and Advances," Current Opinion in Biotechnology, 2002, vol. 13, pp. 65-67.
Hayden M.J., et al., "Multiplex-Ready PCR: A New Method for Multiplexed SSR and SNP Genotyping," BMC Genomics, Feb. 18, 2008, vol. 9, No. 80, pp. 1-12 (12 Pages).
Hellani A., et al., "Clinical Application of Multiple Displacement Amplification in Preimplantation Genetic Diagnosis," Reproductive BioMedicine Online, 2005, vol. 10, No. 3, pp. 376-380 (6 Pages).

Hellani A., et al., "Multiple Displacement Amplification on Single Cell and Possible PGD Applications," Molecular Human Reproduction, Advance Access Publication Oct. 1, 2004, vol. 10, No. 11, pp. 847-852.
Hojsgaard S., et al., "BIFROST—block Recursive Models Induced From Relevant Knowledge, Observations, and Statistical Techniques," Computational Statistics & Data Analysis, 1995, vol. 19, No. 2, pp. 155-175.
Hollas B., et al., "A Stochastic Approach to Count RNA Molecules using DNA Sequencing Methods," Lecture Notes in Computer Science, 2003, vol. 2812, pp. 55-62.
Holleley C.E., et al., "Multiplex Manager 1.0: a Cross-platform Computer Program That Plans and Optimizes Multiplex PCR," Bio Techniques, Jun. 2009, vol. 46, pp. 511-517 (5 Pages).
Hollox E.J., et al., "Extensive Normal Copy Number Variation of a B-Defensin Antimicrobial-Gene Cluster," American Journal of Human Genetics, 2003, vol. 73, pp. 591-600.
Homer N., et al., "Resolving Individuals Contributing Trace Amounts of DNA to Highly Complex Mixtures Using High-density SNP Genotyping Microarrays," PLoS Genetics, Aug. 2008, vol. 4, No. 8, 9 Pages.
Hoogendoorn B., et al., "Genotyping Single Nucleotide Polymorphisms by Primer Extension and High Performance Liquid Chromatography," Hum Genet, 1999, vol. 104, pp. 89-93 (5 Pages).
Hornak M., et al., "Aneuploidy Detection in Pigs Using Comparative Genomic Hybridization: From the Oocytes to Blastocysts," PLoS ONE, Jan. 23, 2012, vol. 7, Issue. 1 (e30335), 6 Pages.
Hospital F., et al., "A General Algorithm to Compute Multilocus Genotype Frequencies Under Various Mating Systems," Jan. 1, 1996, vol. 12, No. 6, pp. 455-462.
Howie B., et al., "Fast and Accurate Genotype Imputation in Genome-Wide Association Studies through Pre-Phasing," Nature Genetics, Aug. 2012, vol. 44, No. 8, pp. 955-959, Jul. 22, 2012.
Hu D.G., et al., "Aneuploidy Detection in Single Cells Using DNA Array-Based Comparative Genomic Hybridization," Molecular Human Reproduction, 2004, vol. 10, No. 4, pp. 283-289.
Hug H., et al., "Measurement of the No. of Molecules of a Single mRNA Species in a Complex mRNA Preparation," Journal of Theoretical Biology, 2003, vol. 221, pp. 615-624.
Hultin E., et al., "Competitive Enzymatic Reaction to Control Allele-Specific Extensions," Nucleic Acids Research, Mar. 14, 2005, vol. 33, No. 5(e48), pp. 1-10.
Ido Y., et al., "Hyperglycemia-induced Apoptosis in Human Umbilical Vein Endothelial Cells: Inhibition by the AMP-activated Protein Kinase Activation," Diabetes, Jan. 2002, vol. 51, pp. 159-167.
Illumina: "Paired-End Sample Preparation Guide," Illumina Catalog # PE-930-1001, Part# 1005063 Rev. E, Feb. 2011, pp. 1-40.
Illumina, Petition for Inter Parties Review of U.S. Pat. No. 8,682,592, Jun. 13, 2019, 91 Pages.
Illumina, Plaintiff/Counterclaim Defendant Illumina, Inc.'s Amended Patent L.R. 3-3 Preliminary Invalidity Contentions for U.S. Pat. No. 8,682,592, Oct. 30, 2018, 22 Pages.
International Preliminary Report on Patentability for International Application No. PCT/US2006/045281, dated May 27, 2008, 7 Pages.
International Preliminary Report on Patentability for International Application No. PCT/US2018/18425, mailed Sep. 6, 2019, 8 Pages.
International Preliminary Report on Patentability for International Application No. PCT/US2019/018274, mailed Aug. 27, 2020, 9 Pages.
International Search Report and Written Opinion for International Application No. PCT/US2006/045281, mailed Sep. 28, 2007, 9 Pages.
International Search Report and Written Opinion for International Application No. PCT/US2008/003547, mailed Apr. 15, 2009, 14 Pages.
International Search Report and Written Opinion for International Application No. PCT/US2009/034506, mailed Jul. 8, 2009, 9 Pages.
International Search Report and Written Opinion for International Application No. PCT/US2009/045335, mailed Jul. 27, 2009, 8 Pages.

(56) References Cited

OTHER PUBLICATIONS

International Search Report and Written Opinion for International Application No. PCT/US2009/052730, mailed Sep. 28, 2009, 8 Pages.
International Search Report and Written Opinion for International Application No. PCT/US2010/050824, mailed Nov. 15, 2010, 8 Pages.
International Search Report and Written Opinion for International Application No. PCT/US2011/037018, mailed Sep. 27, 2011, 12 Pages.
International Search Report and Written Opinion for International Application No. PCT/US2011/061506, mailed Mar. 16, 2012, 11 Pages.
International Search Report and Written Opinion for International Application No. PCT/US2011/066938, mailed Jun. 20, 2012, 15 Pages.
International Search Report and Written Opinion for International Application No. PCT/US2012/066339, mailed Mar. 5, 2013, 22 Pages.
International Search Report and Written Opinion for International Application No. PCT/US2013/028378, mailed May 28, 2013, 11 Pages.
International Search Report and Written Opinion for International Application No. PCT/US2013/057924, mailed Feb. 18, 2014, 8 Pages.
International Search Report and Written Opinion for International Application No. PCT/US2014/051926, mailed Dec. 9, 2014, 9 Pages.
International Search Report and Written Opinion for International Application No. PCT/US2018/18425, mailed May 3, 2018, 10 Pages.
International Search Report and Written Opinion for International Application No. PCT/US2019/018274, mailed Mar. 27, 2019, 13 Pages.
"Ion Ampli Seq Comprehensive Cancer Panel," Product Brochure, Life Technologies Corporation, 2012, 2 Pages, Retrieved from URL: https://tools.lifetechnologies.com/content/sfs/brochures/Ion_CompCancerPanel_Flyer.pdf.
Ishii K., et al., "Optimization of Annealing Temperature to Reduce Bias Caused by a Primer Mismatch in Multitemplate PCR," Applied and Environmental Microbiology, Aug. 2001, vol. 67 (8), pp. 3753-3755.
Jabara C.B., et al., "Accurate Sampling and Deep Sequencing of the HIV-1 Protease Gene Using a Primer ID," The Proceedings of the National Academy of Sciences, Dec. 13, 2011, vol. 108, No. 50, pp. 20166-20171.
Jahr S., et al., "DNA Fragments in the Blood Plasma of Cancer Patients: Quantitations and Evidence for Their Origin from Apoptotic and Necrotic Cells," Cancer Research, Feb. 15, 2001, pp. 1659-1665 (8 Pages).
Jamal-Hanjani M., et al., "Detection of Ubiquitous and Heterogeneous Mutations in Cell-free DNA from Patients with Early-stage Non-small-cell Lung Cancer", Annals of Oncology, May 2016, vol. 27, No. 5, pp. 862-867 (6 Pages), Published online Jan. 28, 2016.
Jamal-Hanjani M., et al., "Tracking Genomic Cancer Evolution for Precision Medicine: The Lung TRACERx Study," PLOS Biology, Jul. 2014, vol. 12, No. 7, pp. 1-7.
Jarvie T., "Next Generation Sequencing Technologies," Drug Discovery Today: Technologies, 2005, vol. 2, No. 3, pp. 255-260.
Jenkins S., et al., "High-throughput SNP Genotyping," Comparative and Functional Genomics, Dec. 5, 2001, vol. 3, pp. 57-66 (11 Pages).
Johnson D.S., et al., "Comprehensive Analysis of Karyotypic Mosaicism between Trophectoderm and Inner Cell Mass," Molecular Human Reproduction, Advanced Access Publication on Jul. 19, 2010, vol. 16, No. 12, pp. 944-949.
Johnson D.S., et al., "Preclinical Validation of a Microarray Method for Full Molecular Karyotyping of Blastomeres in a 24-h Protocol," Human Reproduction, 2010, vol. 25, No. 4, pp. 1066-1075.

Kaplinski L., et al., "MultiPLX: Automatic Grouping and Evaluation of PCR Primers," Bioinformatics, 2005, vol. 21, No. 8, pp. 1701-1702.
Kazakov V.I., et al., "Extracellular DNA in the Blood of Pregnant Women," Tsitologia, 1995, vol. 37, No. 3, pp. 1-8.
Kijak G.H., et al., "Discrepant Results in the Interpretation of HIV-1 Drug-Resistance Genotypic Data Among Widely Used Algorithms," HIV Medicine, 2003, vol. 4, pp. 72-78.
Kim H., et al., "Whole-Genome and Multisector Exome Sequencing of Primary and Post-Treatment Glioblastoma Reveals Patterns of Tumor Evolution," Genome Research, Feb. 3, 2015, vol. 25, No. 3, pp. 316-327 (13 Pages).
Kinde I., et al., "Detection and Quantification of Rare Mutations with Massively Parallel Sequencing," Proceedings of the National Academy of Sciences of the United States of America, Jun. 7, 2011, vol. 108, No. 23, pp. 9530-9535.
Kinnings S.L., et al., "Factors Affecting Levels of Circulating Cell-Free Fetal DNA in Maternal Plasma and Their Implications for Noninvasive Prenatal Testing," Prenatal Diagnosis, 2015, vol. 35, pp. 816-822.
Kirkizlar E., et al., "Detection of Clonal and Subclonal Copy-Number Variants in Cell-Free DNA from Patients with Breast Cancer Using a Massively Multiplexed PCR Methodology," Translational Oncology, Oct. 2015, vol. 8, No. 5, pp. 407-416, DOI: 10.1016/j.tranon.2015.08.004.
Kivioja T., et al., "Counting Absolute Numbers of Molecules using Unique Molecular Identifiers," Nature Methods, Jan. 2012, vol. 9, No. 1, pp. 72-76.
Konfortov B.A., et al., "An Efficient Method for Multi-Locus Molecular Haplotyping," Nucleic Acids Research, 2007, vol. 35, No. 1(e6), 8 Pgs.
Krjutskov K., et al., "Development of a Single Tube 640-plex Genotyping Method for Detection of Nucleic Acid Variations on Microarrays," Nucleic Acids Research, May 23, 2008, vol. 36, No. 12, pp. e75-e75 (7 Pages), XP055207208, ISSN: 0305-1048, DOI: 10.1093/nar/gkn357.
Kuliev A., et al., "Thirteen Years' Experience on Preimplantation Diagnosis: Report of the Fifth International Symposium on Preimplantation Genetics," Reproductive BioMedicine Online, Dec. 22, 2003, vol. 8, No. 2, pp. 229-235 (8 Pages).
Kwok P.Y., "High-throughput Genotyping Assay Approaches," Pharmacogenomics, 2000, vol. 1, No. 1, pp. 1-5.
Lambert-Messerlian G., et al., "Adjustment of Serum Markers in First Trimester Screening," Journal of Medical Screening, 2009, vol. 16, No. 2, pp. 102-103.
Lander E.S., et al., "Initial Sequencing and Analysis of the Human Genome," Nature, Feb. 15, 2001, vol. 409, pp. 860-921.
Lathi R.B., et al., "Informatics Enhanced SNP Microarray Analysis of 30 Miscarriage Samples Compared to Routine Cytogenetics," PLoS ONE, Mar. 5, 2012, vol. 7, Issue No. 3, Article No. e31282, 5 Pages.
Leary R.J., et al., "Detection of Chromosomal Alterations in the Circulation of Cancer Patients with Whole-Genome Sequencing," Science Translational Medicine, Nov. 28, 2012, vol. 4, No. 162(162ra154), 14 Pages, DOI: 10.1126/scitranslmed.3004742.
Leary R.J., et al., "Development of Personalized Tumor Biomarkers Using Massively Parallel Sequencing," Science Translational Medicine, Feb. 24, 2010, vol. 2, Issue. 20 (20ra14), pp. 1-8.
Levsky J.M., et al., "Fluorescence in Situ Hybridization: Past, Present and Future," Journal of Cell Science, 2003, vol. 116, No. 14, pp. 2833-2838.
Li C., et al., "Highly Multiplexed Amplicon Preparation for Targeted Re-Sequencing of Sample Limited Specimens Using the Ion AmpliSeq™ Technology and Semiconductor Sequencing," Proceedings of the Annual Meeting of the American Society of Human Genetics, 2012, 1 Pages, [Retrieved on Oct. 30, 2012], Retrieved from URL: http://www.ashg.org/2012meeting/abstracts/fulltext/f120121811.html.
Li Y., et al., "Size Separation of Circulatory DNA in Maternal Plasma Permits Ready Detection of Fetal DNA Polymorphisms," Clinical Chemistry, 2004, vol. 50, No. 6, pp. 1002-1011.

(56) References Cited

OTHER PUBLICATIONS

Li Y., et al., "Non-invasive Prenatal Diagnosis Using Cell-free Fetal DNA in Maternal Plasma From PGD Pregnancies," Reproductive Bio Medicine Online, 2009, vol. 19, No. 5, pp. 714-720 (8 Pages).
Liao G.J.W., et al., "Targeted Massively Parallel Sequencing of Maternal Plasma DNA Permits Efficient and Unbiased Detection of Fetal Alleles," Clinical Chemistry, 2011, vol. 92, No. 1, pp. 92-101.
Liao J., et al., "An Alternative Linker-Mediated Polymerase Chain Reaction Method using a Dideoxynucleotide to Reduce Amplification Background," Analytical Biochemistry, 1997, vol. 253, pp. 137-139.
Liew M., et al., "Genotyping of Single-Nucleotide Polymorphisms by High-Resolution Melting of Small Amplicons," Clinical Chemistry, 2004, vol. 50, No. 7, pp. 1156-1164.
Lindroos K., et al., "Genotyping SNPs by Minisequencing Primer Extension Using Oligonucleotide Microarrays," Methods in Molecular Biology, Single Nucleotide Polymorphisms: Methods and Protocols, P-K Kwok (ed.), Humana Press, Inc., Totowa, NJ, 2003, vol. 212, pp. 149-165.
Lo Y., "Noninvasive Prenatal Detection of Fetal Chromosomal Aneuploidies by Maternal Plasma Nucleic Acid Analysis: A Review of the Current State of the Art," BJOG An International Journal of Obstetrics and Gynaecology, 2009, vol. 116, pp. 152-157.
Lo Y-M.D., et al., "Detection of Fetal RhD Sequence from Peripheral Blood of Sensitized RhD-Negative Pregnant Women," British Journal of Haematology, 1994, vol. 87, pp. 658-660.
Lo Y-M.D., et al., "Detection of Single-Copy Fetal DNA Sequence from Maternal Blood," The Lancet, Jun. 16, 1990, vol. 335, pp. 1463-1464.
Lo Y.M.D., et al., "Digital PCR for the Molecular Detection of Fetal Chromosomal Aneuploidy," Proceedings of the National Academy of Sciences, Aug. 7, 2007, vol. 104, No. 32, pp. 13116-13121.
Lo Y.M.D., et al., "Fetal Nucleic Acids in Maternal Blood: The Promises," Clinical Chemistry and Laboratory Medicine, 2012, vol. 50, No. 6, pp. 995-998 (5 Pages).
Lo Y.M.D., et al., "Free Fetal DNA in Maternal Circulation," JAMA (Letters to the Editor), Dec. 15, 2004, vol. 292, No. 23, pp. 2835-2836 (3 Pages).
Lo Y.M.D., et al., "Maternal Plasma DNA Sequencing Reveals the Genome-Wide Genetic and Mutational Profile of the Fetus," Science Translational Medicine, Dec. 8, 2010, vol. 2, No. 61, 13 Pages.
Lo Y.M.D., et al., "Non-Invasive Prenatal Diagnosis by Massively Parallel Sequencing of Maternal Plasma DNA," Open Biology, 2012, vol. 2, Article 120086, pp. 1-5.
Lo Y.M.D., et al., "Plasma Placental RNA Allelic Ration Permits Noninvasive Prenatal Chromosomal Aneuploidy Detection," Nature Medicine, Feb. 2007, vol. 13, No. 2, pp. 218-224 (6 Pages).
Lo Y-M.D., et al., "Prenatal Determination of Fetal RhD Status by Analysis of Peripheral Blood of Rhesus Negative Mothers," The Lancet, May 1, 1993, vol. 341, pp. 1147-1148.
Lo Y-M.D., et al., "Prenatal Determination of Fetal Rhesus D Status by DNA Amplification of Peripheral Blood of Rhesus-Negative Mothers," Annals New York Academy of Sciences, 1994, vol. 731, pp. 229-236.
Lo Y-M.D., et al., "Prenatal Sex Determination by DNA Amplification From Maternal Peripheral Blood," The Lancet, Dec. 9, 1989, vol. 2, No. 8676, pp. 1363-1365.
Lo Y.M.D., et al., "Presence of Fetal DNA in Maternal Plasma and Serum", The Lancet, Aug. 16, 1997, vol. 350, pp. 485-487.
Lo Y.M.D., et al., "Quantitative Analysis of Fetal DNA in Maternal Plasma and Serum: Implications for Noninvasive Prenatal Diagnosis," American Journal of Human Genetics, 1998, vol. 62, pp. 768-775.
Lo Y.M.D., et al., "Rapid Clearance of Fetal DNA from Maternal Plasma," American Journal of Human Genetics, 1999, vol. 64, pp. 218-224.
Lo Y-M.D., et al., "Strategies for the Detection of Autosomal Fetal DNA Sequence from Maternal Peripheral Blood," Annals New York Academy of Sciences, 1994, vol. 731, pp. 204-213.
Lo Y.M.D., et al., "Two-Way Cell Traffic Between Mother and Fetus: Biologic and Clinical Implications," Blood, Dec. 1, 1996, vol. 88, No. 11, pp. 4390-4395 (7 Pages).
Lo Y.M.D., "Fetal Nucleic Acids in Maternal Plasma: Toward the Development of Noninvasive Prenatal Diagnosis of Fetal Chromosomal Aneuploidies," Annals of the New York Academy of Sciences, 2008, vol. 1137, pp. 140-143.
Lu I-J., et al., "Establishment of a System Based on Universal Multiplex-PCR for Screening Genetically Modified Crops," Analytical and Bioanalytical Chemistry, Oct. 24, 2009, vol. 396, pp. 2055-2064.
Lui Y.Y.N., et al., "Predominant Hematopoietic Origin of Cell-Free DNA in Plasma and Serum after Sex-Mismatched Bone Marrow Transplantation," Clinical Chemistry, 2002, vol. 48, vol. 3, pp. 421-427.
Lun F.M.F., et al., "Noninvasive Prenatal Diagnosis of Monogenic Diseases by Digital Size Selection and Relative Mutation Dosage on DNA in Maternal Plasma," PNAS, Dec. 16, 2008, vol. 105, No. 50, pp. 19920-19925.
Ma X., et al., "Rise and Fall of Subclones from Diagnosis to Relapse in Pediatric B-Acute Lymphoblastic Leukaemia," Nature Communications, Mar. 19, 2015, vol. 6, No. 6604, pp. 1-12.
Mamon H., et al., "Letters to the Editor: Preferential Amplification of Apoptotic DNA from Plasma: Potential for Enhancing Detection of Minor DNA Alterations in Circulating DNA," Clinical Chemistry, 2008, vol. 54, No. 9, pp. 1582-1584.
Maniatis T., et al., "Molecular Cloning: A Laboratory Manual," Cold Spring Harbor Laboratory, New York, Thirteenth Printing, Purification of Nucleic Acids, 1986, pp. 458-459 (4 Pages).
Mansfield E.S., "Diagnosis of Down Syndrome and Other Aneuploidies Using Quantitative Polymerase Chain Reaction and Small Tandem Repeat Polymorphisms," Human Molecular Genetics, 1993, vol. 2, No. 1, pp. 43-50.
Margulies M., et al., "Genome Sequencing in Microfabricated High-Density Picolitre Reactors plus Supplemental Methods" Nature, Sep. 15, 2005, vol. 437, pp. 376-380 (40 Pages).
Markoulatos P., et al., "Multiplex Polymerase Chain Reaction: a Practical Approach," Journal of Clinical Laboratory Analysis, New York, NY, US, Jan. 1, 2002, vol. 16, No. 1, pp. 47-51, XP009003351, ISSN: 0887-8013, DOI: 10.1002/JCLA.2058, the whole Document.
May R.M., "How Many Species Are There on Earth?," Science, Sep. 16, 1988, vol. 241, No. 4872, pp. 1441-1449 (10 Pages).
McBride D.J., et al., "Use of Cancer-Specific Genomic Rearrangements to Quantify Disease Burden in Plasma from Patients with Solid Tumors," Genes, Chromosomes & Cancer, Aug. 19, 2010, vol. 49, pp. 1062-1069.
McCloskey M.L., et al., "Encoding PCR Products with Batch-Stamps and Barcodes," Biochemical Genetics, Oct. 23, 2007, vol. 45, pp. 761-767.
McCray A.T., et al., "Aggregating UMLS Semantic Types for Reducing Conceptual Complexity," MEDINFO 2001: Proceedings of the 10th World Congress on Medical Informatics (Studies in Health Technology and Informatics, IOS Press Amsterdam, V. Patel et al. (eds.), 2001, vol. 84, pp. 216-220.
Mennuti M.T., et al., "Is It Time to Sound an Alarm About False-Positive Cell-Free DNA Testing for Fetal Aneuploidy,?" American Journal of Obstetrics, 2013, 5 Pages.
Merriam-Webster: "Medical Definition of Stimulant," Mar. 14, 2016, 7 Pages, Retrieved from URL: http://www.merriam-webster.com/medical/stimulant.
Merriam-Webster: "Universal Definition," Merriam-Webster.com (Online), 3 Pages, [Retrieved on Jul. 23, 2014], Retrieved from URL: http://www.merriam-webster.com/dictionary/universal.
Mersy E., et al., "Noninvasive Detection of Fetal Trisomy 21: Systematic Review and Report of Quality and Outcomes of Diagnostic Accuracy Studies Performed Between 1997 and 2012," Human Reproduction Update, 2013, vol. 19, No. 4, pp. 318-329.
Miller R.R., et al., "Homocysteine-Induced Changes in Brain Membrane Composition Correlate with Increased Brain Caspase-3 Activities and Reduced Chick Embryo Viability," Comparative Biochemistry and Physiology Part B, 2003, vol. 136, pp. 521-532.
Miller R.R.Jr., et al., "Hyperglycemia-induced Changes in Hepatic Membrane Fatty Acid Composition Correlate With Increased Caspase-3

(56) References Cited

OTHER PUBLICATIONS

Activities and Reduced Chick Embryo Viability," Comparative Biochemistry and Physiology, Part B, 2005, vol. 141, pp. 323-330.
Miner B.E., et al., "Molecular Barcodes Detect Redundancy and Contamination in Hairpin- Bisulfite PCR," Nucleic Acids Research, Sep. 30, 2004, vol. 32(17), pp. 1-4.
Minkoff E., et al., "Stem Cells, Cell Division, and Cancer," Biology Today, Third Edition, Chapter 12, 2004, 10 Pages, Jan. 2000.
Morand C., et al., "Hesperidin Contributes to the Vascular Protective Effects of Orange Juice: A Randomized Crossover Study in Healthy Volunteers (1-3)," The American Journal of Clinical Nutrition, Jan. 2011, vol. 93, No. 1, pp. 73-80, Epublished on Nov. 10, 2010.
Munne S., et al., "Chromosome Abnormalities in Human Embryos," European Society of Human Reproduction and Embryology, Human Reproduction Update, 1998, vol. 4, No. 6, pp. 842-855.
Munne S., et al., "Chromosome Abnormalities in Human Embryos," Textbook of Assisted Reproductive Techniques, May 27, 2004, pp. 355-377 (24 Pages).
Murtaza M., et al., "Non-Invasive Analysis of Acquired Resistance to Cancer Therapy by Sequencing of Plasma DNA," Nature, May 2, 2013, vol. 497, 6 Pages, DOI:10.1038/nature12065).
Muse S.V., "Examining Rates and Patterns of Nucleotide Substitution in Plants," Plant Molecular Biology, 2000, vol. 42, pp. 25-43.
Myers C.L., et al., "Accurate Detection of Aneuploidies in Array CGH and Gene Expression Microarray Data," Bioinformatics, 2004, vol. 20, No. 18, pp. 3533-3543.
Nannya Y., et al., "A Robust Algorithm for Copy Number Detection Using High-density Oligonucleotide Single Nucleotide Polymorphism Genotyping Arrays," Cancer Research, Jul. 15, 2005, vol. 65, No. 14, pp. 6071-6079.
Narayan A., et al., "Ultrasensitive Measurement of Hotspot Mutations in Tumor DNA in Blood using Error-Suppressed Multiplexed Deep Sequencing," Cancer Research, Jul. 15, 2012, vol. 72, No. 14, pp. 3492-3498 (8 Pages).
Natera Inc .: "Declaration of Sandra L. Haberny, In Support of Defendant Natera, Inc.,'s Motion to Dismiss Pursuant to Federal Rule of cIVIL pROCEDURE 12(B)(6)," May 16, 2019, 3 Pages.
Natera, Inc: "Defendant Natera, Inc.'s Corporate Disclosure Statement," May 31, 2019, 2 Pages.
Natera, Inc: "Defendant Natera, Inc.'s Invalidity Contentions Under Patent L.R. 3-3; Document Production Accompanying Invalidity Contentions Under Patent L.R. 3-4," Aug. 20, 2018, 17 Pages.
Natera, Inc: "Defendant Natera, Inc's Motion to Dismiss Pursuant to Federal Rule of Civil Procedure 12(b)(6)," May 16, 2019, 2 Pages.
Natera, Inc: "Defendant Natera, Inc's Opening Brief in Support of Motion to Dismiss Pursuant to Federal Rule of Civil Procedure 12(b)(6)," May 16, 2019, 26 Pages.
Natera, Inc: "Exhibit 8 EHRICH Invalidity Chart," Aug. 20, 2018, 16 Pages.
Natera, Inc: "Exhibits A & B." May 31, 2019, 38 Pages.
Natera, Inc.: "Petitioner Reply Per Board Order of Nov. 2, 2018 (Paper No. 10)," Nov. 9, 2018, 8 Pages.
NCBI: "Blast of AAAAAAAAATTTAAAAAAAAATTT, Basic Local Alignment Search Tool," 9 Pages, [Retrieved on May 4, 2015], Retrieved from URL: http://blast.ncbi.nlm.nih.gov/Blast.cgi.
NCBI: "DbSNP, Short Genetic Variations," Reference SNP Cluster Report: rs2056688, 3 Pages, [Retrieved on May 4, 2015], Retrieved from URL: http://www.ncbi.nlm.nih.gov/projects/SNP/snp_ref.cgi?rs=2056688.
New Health Guide: "How Many Carbs in a Potato?," Nov. 1, 2014, 3 Pages, Retrieved from the Internet: http://www.newhealthguide.org/How-Many-Carbs-In-A-Potato.html.
Nicolaides K.H., et al., "Noninvasive Prenatal Testing for Fetal Trisomies in a Routinely Screened First-Trimester Population," American Journal of Obstetrics and Gynecology, (Article in Press), 2012, vol. 207, pp. 1.e1-1.e6.
Nicolaides K.H., et al., "Prenatal Detection of Fetal Triploidy from Cell-Free DNA Testing in Maternal Blood," Fetal Diagnosis and Therapy, Oct. 10, 2013, pp. 1-6.
Nicolaides K.H., et al., "Validation of Targeted Sequencing of Single-Nucleotide Polymorphisms for Non-Invasive Prenatal Detection of Aneuploidy of Chromosomes 13, 18, 21, X, and Y," Prenatal Diagnosis, Jun. 2013, vol. 33, No. 6, pp. 575-579.
Nygren A.O., et al., "Quantification of Fetal DNA by Use of Methylation-Based DNA Discrimination," Clinical Chemistry, 2010, vol. 56, No. 10, pp. 1627-1635.
Ogino S., et al., "Bayesian Analysis and Risk Assessment in Genetic Counseling and Testing," Journal of Molecular Diagnostics, Feb. 2004, vol. 6, No. 1, 9 Pages.
Ohsawa M., et al., "Prenatal Diagnosis of Two Pedigrees of Fukuyama Type Congenital Muscular Dystrophy by Polymorphism Analysis," The Health and Welfare Ministry, 1994, 5 Pages.
O'Malley R.C., et al., "An Adapter Ligation-Mediated PCR Method for High-Throughput Mapping of T-DNA Inserts in the *Arabidopsis* Genome," Nature Protocols, 2007, vol. 2, No. 11, pp. 2910-2917, 9 Pages.
Orozco A.F., et al., "Placental Release of Distinct DNA-Associated Micro-Particles into Maternal Circulation: Reflective of Gestation Time and Preeclampsia," Placenta, 2009, vol. 30, pp. 891-897.
Ozawa M., et al., "Two Families With Fukuyama Congenital Muscular Dystrophy That Underwent in Utero Diagnosis Based on Polymorphism Analysis," Clinical Muscular Dystrophy: Research in Immunology and Genetic Counseling—FY 1994 Research Report (including text in Japanese), 1994, vol. 8, 8 Pages.
Paez J.G., et al., "Genome Coverage and Sequence Fidelity of Φ29 Polymerase-based Multiple Strand Displacement Whole Genome Amplification," Nucleic Acids Research, 2004, vol. 32, No. 9(e71), pp. 1-11.
Page S.L., et al., "Chromosome Choreography: The Meiotic Ballet," Science, Aug. 8, 2003, vol. 301, No. 5634, pp. 785-789, 6 Pages.
Palomaki G., et al., "DNA Sequencing of Maternal Plasma Reliably Identifies Trisomy 18 and Trisomy 13 as Well as Down Syndrome: an International Collaborative Study," Genetics in Medicine, Mar. 2012, vol. 14, No. 3, 10 Pages.
Palomaki G.E., et al., "DNA Sequencing of Maternal Plasma to Detect Down Syndrome: An International Clinical Validation Study," Genetics in Medicine, Nov. 2001, vol. 13, No. 11, pp. 913-920.
Papageorgiou E.A., et al., Fetal-Specific DNA Methylation Ratio Permits Noninvasive Prenatal Diagnosis of Trisomy 21, Nature Medicine, Advanced Online Publication, Mar. 6, 2011, vol. 17, pp. 510-513 (5 Pages).
Pathak A.K., et al., "Circulating Cell-Free DNA in Plasma/Serum of Lung Cancer Patients as a Potential Screening and Prognostic Tool," Clinical Chemistry, 2006, vol. 52, No. 10, pp. 1833-1842.
Pearson K., "On the Criterion That a Given System of Deviations From the Probable in the Case of a Correlated System of Variables is Such That It Can Be Reasonably Supposed to Have Arisen From Random Sampling," Philosophical Magazine Series 5, 1900, vol. 50, Issue. 302, pp. 157-175.
Pena S.D.J., et al., "Paternity Testing in the DNA Era," Trends In Genetics, Jun. 1994, vol. 10, No. 6, pp. 204-209.
Pergament E., et al., "Single-Nucleotide Polymorphism-Based Noninvasive Prenatal Screening in a High-Risk and Low-Risk Cohort," Obstetrics & Gynecology, Aug. 2014, vol. 124, No. 2, Part 1, pp. 210-218 (26 Pages), Appendix.
Perkel J.M., "Overcoming the Challenges of Multiplex PCR," Biocompare Editorial Article, Oct. 23, 2012, pp. 1-5.
Perry G.H., et al., "The Fine-Scale and Complex Architecture of Human Copy-Number Variation," The American Journal of Human Genetics, Mar. 2008, vol. 82, pp. 685-695.
Pertl B., et al., "Detection of Male and Female Fetal DNA in Maternal Plasma by Multiplex Fluorescent Polymerase Chain Reaction Amplification of Short Tandem Repeats," Human Genetic, Jan. 2000, vol. 106, pp. 45-49.
Peters D., et al., "Noninvasive Prenatal Diagnosis of a Fetal Microdeletion Syndrome," New England Journal of Medicine, 2011, vol. 365, No. 11, pp. 1847-1848.

(56) References Cited

OTHER PUBLICATIONS

Pfaffl M.W., et al., "Relative Expression Software Tool (REST) for Group-Wise Comparison and Statistical Analysis of Relative Expression Results in real-Time PCR," Nucleic Acids Research, 2002, vol. 30, No. 9, 10 Pages.

Phillips C., et al., "Resolving Relationship Tests That Show Ambiguous Str Results Using Autosomal SNPs as Supplementary Markers," Forensic Science International: Genetics, 2008, vol. 2, pp. 198-204.

Podder M., et al., "Robust SNP Genotyping by Multiplex PCR and Arrayed Primer," BMC Medical Genomics, 2008, vol. 1, No. 5, pp. 1-15.

Popova T., et al., "Genome Alteration Print (GAP): A Tool to Visualize and Mine Complex Cancer Genomic Profiles Obtained by SNP Arrays," Genome Biology, Nov. 11, 2009, vol. 10, Issue. 11, Article. R128, pp. 1-14.

Porreca G.J., et al., "Multiplex Amplification of Large Sets of Human Exons," Nature Methods, Advance Online Publication, Nov. 2007, vol. 4, No. 11, pp. 931-936, DOI: 10.1038/nmeth1110, (Epub Oct. 14, 2007).

Price T.S., et al., "SW-array: a Dynamic Programming Solution for the Identification of Copy-number Changes in Genomic DNA Using Array Comparative Genome Hybridization Data," Nucleic Acids Research, Jun. 16, 2005, vol. 33, No. 11, pp. 3455-3464.

Primdahl H., et al., "Allelic Imbalances in Human Bladder Cancer Genome-Wide Detection With High-Density Single-Nucleotide Polymorphism Arrays," Journal of the National Cancer Institute, Feb. 6, 2002, vol. 94, No. 3, pp. 216-223.

PRNewswire: "Research Suggests Daily Consumption of Orange Juice can Reduce Blood Pressure and may Provide Beneficial Effects to Blood Vessel Function: New Study Identified Health Benefits in Orange Juice," Dec. 8, 2010, 3 Pages.

Quinn G.P., et al., "Experimental Design and Data Analysis for Biologists," Graphical Exploration of Data, 2002, pp. 64-67.

Rabinowitz M., et al., "Accurate Prediction of HIV-1 Drug Response from the Reverse Transcriptase and Protease Amino Acid Sequences Using Sparse Models Created by Convex Optimization," Bioinformatics, 2006, vol. 22, No. 5, pp. 541-549.

Rabinowitz M., et al., "Non-Invasive Prenatal Aneuploidy Testing of Chromosomes 13, 18, 21, X, and Y Using Targeted Sequencing of Polymorphic Loci," The American Society of Human Genetics, Meeting poster, 2012, 1 Page.

Rabinowitz M., et al., "Origins and Rates of Aneuploidy in Human Blastomeres," Fertility and Sterility, Elsevier Science Inc, New York, NY, USA, Feb. 2012, vol. 97, No. 2, pp. 395-401, DOI: 10.1016/J.FERTNSTERT.2011.11.034, ISSN: 0015-0282, XP028453561, [Retrieved on Nov. 30, 2011], Nov. 24, 2011.

Rachlin J., et al., "Computational Tradeoffs in Multiplex PCR Assay Design for SNP Genotyping," BMC Genomics, Jul. 25, 2005, vol. 6, No. 102, 11 Pages.

Ragoussis J., "Genotyping Technologies for Genetic Research," Annual Review of Genomics and Human Genetics, Sep. 1, 2009, vol. 10, No. 1, pp. 117-133 (19 Pages).

Rahmann S., et al., "Mean and Variance of the Gibbs Free Energy of Oligonucleotides in the Nearest Neighbor Model Under Varying Conditions," Bioinformatics, 2004, vol. 20, No., 17, pp. 2928-2933.

"Random Variable," From The Penguin Dictionary of Mathematics, 2008, 1 Page, Retrieved from URL: http://credoreference.com/entry/penguinmath/randomvariable.

Rava R.P., et al., "Circulating Fetal Cell-Free DNA Fractions Differ in Autosomal Aneuploidies and Monosomy X," Clinical Chemistry, (Papers in Press), 2014, vol. 60, No. 1, 8 Pages, Published as Sep. 17, 2013.

Rechitsky S., et al., "Preimplantation Genetic Diagnosis with HLA Matching," Reproductive BioMedicine Online, 2004, vol. 9, No. 2, pp. 210-221 (13 Pages).

Renwick P., et al., "Proof of Principle and First Cases Using Preimplantation Genetic Haplotyping—A Paradigm Shift for Embryo Diagnosis," Reproductive BioMedicine Online, 2006, vol. 13, No. 1, pp. 110-119 (11 Pages).

Ricciotti H., "Eating by Trimester," Online, Aug. 8, 2014, 4 Pages, Retrieved from URL: http://www.youandyourfamily.com/article.php?story=Eating+by+Trimester.

Riley D.E., et al., "DNA Testing: An Introduction for Non-Scientists an Illustrated Explanation," Scientific Testimony: An Online Journal, Apr. 6, 2005, 22 Pages, Retrieved from URL: http://www.scientific.org/tutorials/articles/riley/riley.html.

Rogaeva E., et al., "The Solved and Unsolved Mysteries of the Genetics of Early-Onset Alzheimer's Disease," NeuroMolecular Medicine, 2002, vol. 2, pp. 1-10.

Roper S.M., et al., "Forensic Aspects of DNA-Based Human Identity Testing," Journal of Forensic Nursing, 2008, vol. 4, No. 4, pp. 150-156.

Rouk K.H., "Optimization and Troubleshooting in PCR," PCR Methods and Application, 1995, vol. 4, pp. S185-S194, 11 Pages.

Rozen S., et al., "Primer3 on the WWW for General Users and for Biologis Programmers," Methods in Molecular Biology, Bioinformatics Methods and Protocols, 1999, vol. 132, pp. 365-386.

Russell L.M., "X Chromosome Loss and Ageing," Cytogenetic and Genome Research, 2007, vol. 116, pp. 181-185.

Ryan A., et al., "Informatics-Based, Highly Accurate, Noninvasive Prenatal Paternity Testing," Genetics in Medicine, (Advance Online Publication), 2012, 5 Pages.

Rychlik W., et al., "Optimization of the Annealing Temperature for DNA Amplification in Vitro," Nucleic Acids Research, 1990, vol. 18, No. 21, pp. 6409-6412.

Sahota A., et al., "Evaluation of Seven PCR-Based Assays for the Analysis of Microchimerism," Clinical Biochemistry, 1998, vol. 31, No. 18, pp. 641-645.

Samango-Sprouse C., et al., "SNP-Based Non-Invasive Prenatal Testing Detects Sex Chromosome Aneuploidies With High Accuracy," Prenatal Diagnosis, 2013, vol. 33, 643-649.

Sander C., "Genomic Medicine and the Future of Health Care," Science, Mar. 17, 2000, vol. 287, No. 5460, pp. 1977-1978 (3 Pages).

Santalucia J., J.R., et al., "Improved Nearest-Neighbor Parameters for Predicting DNA Duplex Stability," Biochemistry, 1996, vol. 35, pp. 3555-3562.

Santalucia J., Jr., et al., "The Thermodynamics of DNA Structural Motifs," Annual Reviews, Biophysics and Biomolecular Structure, 2004, vol. 33, pp. 415-440 (30 Pages).

Sasabe Y., "Genetic Diagnosis of Gametes and Embryos Resulting from ART," Japanese Journal of Fertility and Sterility, 2001, vol. 46, No. 1, pp. 43-46 (6 Pages).

Schmitt M.W., "Detection of Ultra-Rare Mutations by the Next Generation Sequencing," Proceedings of the National Academy of Sciences of the United States of America, Sep. 4, 2012, vol. 109, No. 36, pp. 14508-14513 (9 Pages), Supporting Information.

Schoumans J., et al., "Detection of Chromosomal Imbalances in Children With Idiopathic Mental Retardation by Array Based Comparative Genomic Hybridisation (Array-CGH)," Journal of Medical Genetics, 2005, vol. 42, pp. 699-705 (8 Pages).

Sebat J., et al., "Strong Association of De Novo Copy Number Mutations with Autism," Science, Apr. 20, 2007, vol. 316, pp. 445-449 (6 Pages).

Sehnert A.J., et al., Optimal Detection of Fetal Chromosomal Abnormalities by Massively Parallel DNA Sequencing of Cell-Free Fetal DNA from Maternal Blood, Clinical Chemistry, Apr. 25, 2011, vol. 57, No. 7, pp. 1-8.

Sermon K., et al., "Preimplantation Genetic Diagnosis," The Lancet, Lancet Limited, May 15, 2004, vol. 363, No. 9421, pp. 1633-1641, 2000.

Servin B., et al., "MOM: A Program to Compute Fully Informative Genotype Frequencies in Complex Breeding Schemes", Journal of Heredity, Jan. 1, 2022, vol. 93, No. 3, pp. 227-228.

Shaw-Smith C., et al., "Microarray Based Comparative Genomic Hybridisation (array-CGH) Detects Submicroscopic Chromosomal Deletions and Duplications in Patients with Learning Disability/Mental Retardation and Dysmorphic Features," J Med Genet, 2004, vol. 41, pp. 241-248.

Shen P., et al., "High-quality DNA Sequence Capture of 524 Disease Candidate Genes," Proceedings of the National Academy of Sciences, Apr. 5, 2011, vol. 108, No. 16, pp. 6549-6554.

(56) References Cited

OTHER PUBLICATIONS

Shen R., et al., "High-Throughput SNP Genotyping on Universal Bead Arrays," Mutation Research, 2005, vol. 573, pp. 70-82.
Shen Z., et al., "MPprimer: A Program for Reliable Multiplex PCR Primer Design," BMC Bioinformatics, Mar. 18, 2010, vol. 11, No. 143, pp. 1-7.
Sherlock J., et al., "Assessment of Diagnostic Quantitative Fluorescent Multiplex Polymerase Chain Reaction Assays Performed on Single Cells," Annals of Human Genetics, 1998, vol. 62, No. 1, pp. 9-23.
Shiroguchi K., et al., "Digital RNA Sequencing Minimizes Sequence-Dependent Bias and Amplification Noise with Optimized Single-Molecule Barcodes," PNAS, Jan. 24, 2012, vol. 109, No. 4, pp. 1347-1352.
Simpson J.L., et al., "Fetal Cells in Maternal Blood: Overview and Historical Perspective," Annals New York Academy of Sciences, Sep. 1994, vol. 731, pp. 1-8.
Sint D., et al., "Advances in Multiplex PCR: Balancing Primer Efficiencies and Improving Detection Success," Methods in Ecology and Evolution, 2012, vol. 3, pp. 898-905.
Slater H.R., et al., "High-Resolution Identification of Chromosomal Abnormalities Using Oligonucleotide Arrays Containing 116,204 SNPs," The American Journal of Human Genetics, 2005, vol. 77, No. 5, pp. 709-726.
Snijders A.M., et al., "Assembly of Microarrays for Genome-Wide Measurement of DNA Copy Number," Nature Genetic, Nov. 2001, vol. 29, pp. 263-264.
Sourceforge: "PRIMER3," Information Sheet, Sourceforge.net, (Online), Oct. 26, 2009, 1 Page, [Retrieved on Nov. 12, 2012], Retrieved from URL: http://primer3.sourceforge.net/.
Sparks A.B., et al., "Selective Analysis of Cell-free DNA in Maternal Blood for Evaluation of Fetal Trisomy," Prenatal Diagnosis, 2012, vol. 32, No. 1-7, pp. 3-9 (7 Pages), Epublished on Jan. 6, 2012.
Sparks A.B., et al., "Non-invasive Prenatal Detection and Selective Analysis of Cell-free DNA Obtained From Maternal Blood: Evaluation for Trisomy 21 and Trisomy 18," American Journal of Obstetrics & Gynecology, Apr. 2012, vol. 206, pp. 319.e1-319.e9.
Spiro A., et al., "A Bead-Based Method for Multiplexed Identification and Quantitation of DNA Sequences Using Flow Cytometry," Applied and Environmental Microbiology, Oct. 2000, vol. 66, No. 10, pp. 4258-4265.
Spits C., et al., "Optimization and Evaluation of Single-Cell Whole Genome Multiple Displacement Amplification," Human Mutation, 2006, vol. 27, No. 5, pp. 496-503.
Srinivasan A., et al., "Noninvasive Detection of Fetal Subchromosome Abnormalities via Deep Sequencing of Maternal Plasma," The American Journal of Human Genetics, Feb. 7, 2013, vol. 92, pp. 167-176, Published Jan. 10, 2013.
Stephens M., et al., "A Comparison of Bayesian Methods for Haplotype Reconstruction from Population Genotype Data," The American Journal of Human Genetics, 2003, vol. 73, pp. 1162-1169.
Stevens R., et al., "Ontology-Based Knowledge Representation for Bioinformatics," Briefings in Bioinformatics, Nov. 2000, vol. 1, No. 4, pp. 398-414.
Steyerberg E.W., et al., "Application of Shrinkage Techniques in Logistic Regression Analysis: A Case Study," Statistica Neerlandica, 2001, vol. 55, No. 1, pp. 76-88.
Strom C.M., et al., "Neonatal Outcome of Preimplantation Genetic Diagnosis by Polar Body Removal: The First 109 Infants," Pediatrics, 2000, vol. 106, No. 4, pp. 650-653 (6 Pages).
Strom C.M., et al., "Three Births after Preimplantation Genetic Diagnosis for Cystic Fibrosis with Sequential First and Second Polar Body Analysis," American Journal of Obstetrics and Gynecology, Jun. 1998, vol. 178, No. 6, pp. 1298-1306.
Stroun M., et al., "Prehistory of the Notion of Circulating Nucleic Acids in Plasma/Serum (CNAPS): Birth of a Hypothesis," Annals of the New York Academy of Sciences, 2006, vol. 1075, pp. 10-20.

Su S-Y., et al., "Inferring Combined CNV/SNP Haplotypes From Genotype Data," Bioinformatics, Jun. 1, 2010, vol. 26, No. 11, pp. 1437-1445.
Sun G., et al., "SNPs in Human Mirna Genes Affect Biogenesis and Function," RNA, 2009, vol. 15, No. 9, pp. 1640-1651.
Sweetkind-Singer J.A., "Log-Penalized Linear Regression," International Symposium on Information Theory, Jun. 29, 2003-Jul. 4, 2003, p. 286.
Takara Biomedicals: "Competitive PCR Guide," Lit. # L0126 Rev. Aug. 1999, Aug. 1999, 9 Pages.
Taliun D., et al., "Efficient Haplotype Block Recognition of Very Long and Dense Genetic Sequences," BMC Bioinformatics, Jan. 14, 2014, vol. 15, No. 10, pp. 1-18.
Tamura A., et al., "Sibling Incest and Formulation of Paternity Probability Case Report," Legal Medicine, Dec. 2000, vol. 2, No. 4, pp. 189-196.
Tang N., et al., "Detection of Fetal-Derived Paternally Inherited X-Chromosome Polymorphisms in Maternal Plasma," Clinical Chemistry, 1999, vol. 45, No. 11, pp. 2033-2035.
Tebbutt S.J., et al., "Microarray Genotyping Resource to Determine Population Stratification in Genetic Association Studies of Complex Disease," BioTechniques, Dec. 2004, vol. 37, No. 6, pp. 977-985.
Ten Bosch J.R., et al., "Keeping Up With the Next Generaton Massively Parallel Sequencing in Clinical Diagnostics," Journal of Molecular Diagnostics, Nov. 2008, vol. 10, No. 6, pp. 484-492.
Tewhey R., et al., "The Importance of Phase Information for Human Genomics," Nature Reviews Genetics, Mar. 1, 2011, vol. 12, No. 3, pp. 215-223.
Thermofisher Scientific: "Ion AmpliSeq Cancer Hotspot Panel v2," 2015, 2 Pages, Retrieved from URL: https://tools.thermofisher.com/content/sfs/brochures/Ion-AmpliSeq-Cancer-Hotspot-Panel-Flyer.pdf.
Thomas M.R., et al., "The Time of Appearance and Disappearance of Fetal DNA from the Maternal Circulation," Prenatal Diagnosis, 1995, vol. 15, pp. 641-646.
Tong Y.K., et al., "Noninvasive Prenatal Detection of Fetal Trisomy 18 by Epigenetic Allelic Ratio Analysis in Maternal Plasma: Theoretical and Empirical Considerations," Clinical Chemistry, 2006, vol. 52, No. 12, pp. 2194-2202.
Tong Y.K., et al., "Noninvasive Prenatal Detection of Trisomy 21 by an Epigenetic-Genetic Chromosome-Dosage Approach," Clinical Chemistry, Jan. 2010, vol. 56, No. 1, pp. 90-98.
Troyanskaya O.G., et al., "A Bayesian Framework for Combining Heterogeneous Data Sources for Gene Function Prediction (In *Saccharomyces cerevisiae*)," The Proceedings of the National Academy of Sciences, Jul. 8, 2003, vol. 100, No. 14, pp. 8348-8353.
Tsui N.B.Y., et al., "Non-invasive Prenatal Detection of Fetal Trisomy 18 by RNA-SNP Allelic Ratio Analysis Using Maternal Plasma SERPINB2 MRNA: A Feasibility Study," Prenatal Diagnosis, 2009, vol. 29, pp. 1031-1037.
Tu J., et al., "Pair-barcode High-throughput Sequencing for Large-scale Multiplexed Sample Analysis," BMC Genomics, Jan. 25, 2012, vol. 13, No. 43, pp. 1-9.
Turner E.H., et al., "Massively Parallel Exon Capture and Library-Free Resequencing Across 16 Genomes," Nature Methods, May 2009, vol. 6, No. 5, pp. 315-316.
Vallone P.M., et al., "AutoDimer: A Screening Tool for Primer-Dimer and Hairpin Structures," BioTechniques, Aug. 2004, vol. 37, pp. 226-231.
Varley K.E., et al., "Nested Patch PCR Enables Highly Multiplexed Mutation Discovery in Candidate Genes," Genome Research, Nov. 2008, vol. 18, No. 11, pp. 1844-1850, DOI: 10.1101/gr.078204.108.
Verlinsky Y., et al., "Over a Decade of Experience with Preimplantation Genetic Diagnosis," Fertility and Sterility, Aug. 2004, vol. 82, No. 2, pp. 302-303.
Wagner J., et al., "Non-invasive Prenatal Paternity Testing From Maternal Blood," International Journal of Legal Medicine, 2009, vol. 123, pp. 75-79 (3 Pages), Published Online Oct. 24, 2008.
Wang D.G., et al., "Large-Scale Identification, Mapping, and Genotyping of Single-Nucleotide Polymorphisms in the Human Genome," Science, May 15, 1998, vol. 280, No. 5366, pp. 1077-1082, 7 Pages.

(56) References Cited

OTHER PUBLICATIONS

Wang E., et al., "Gestational Age and Maternal Weight Effects on Fetal Cell-Free DNA in Maternal Plasma," Prenatal Diagnosis, 2013, vol. 33, pp. 662-666.
Wang H-Y., et al., "A Genotyping System Capable of Simultaneously Analyzing 1000 Single Nucleotide Polymorphisms in a Haploid Genome," Genome Research, 2005, vol. 15, pp. 276-283, 9 Pages.
Wang T-L., et al., "Digital Karyotyping," Dec. 10, 2002, vol. 99, No. 25, pp. 16156-16161.
Wang Y., et al., "Allele Quantification Using Molecular Inversion Probes (MIP)," Nucleic Acids Research, Oxford University 1 Press, GB, Nov. 1, 2005, vol. 33, No. 21, pp. e183/1-e183/14, XP009127259, ISSN: 1362-4962, DOI: 10.1093/NAR/GNI177 [retrieved on Nov. 28, 2005], Abstract.
Wapner R., et al., "First-Trimester Screening forTrisomies 21 and 18," The New England Journal of Medicine, Oct. 9, 2003, vol. 349, No. 15, pp. 1405-1413.
Wapner R.J., et al., "Chromosomal Microarray Versus Karyotyping for Prenatal Diagnosis," The New England Journal of Medicine, Dec. 6, 2012, vol. 367, No. 23, pp. 2175-2184.
Watkins N.E., et al., "Thermodynamic Contributions of Single Internal rA. dA, rC. dC, rG. dG and rU. dT Mismatches in RNA/DNA Duplexes," Nucleic Acids Research, 2011, vol. 39, No. 5, pp. 1894-1902, 2010.
Wells D., "Advances in Preimplantation Genetic Diagnosis," European Journal of Obstetrics and Gynecology and Reproductive Biology, 2004, vol. 115, Supplement, pp. S97-S101.
Wells D., et al., "Detailed Chromosomal and Molecular Genetic Analysis of Single Cells by Whole Genome Amplification and Comparative Genomic Hybridisation," Nucleic Acids Research, 1999, vol. 27, No. 4, pp. 1214-1218.
Wells D., et al., "Microarray for Analysis and Diagnosis of Human Embryos," 12th International Congress on Prenatal Diagnosis and Therapy, Budapest, Hungary, Jun. 24-27, 2004, pp. 9-17.
Wen D., et al., "Universal Multiplex PCR: A Novel Method of Simultaneous Amplification of Multiple DNA Fragments," Plant Methods, Null, Aug. 15, 2012, vol. 8, No. 32, pp. 1-9.
Wikipedia: "Maximum a Posteriori Estimation," The Free Encyclopedia, Oct. 30, 2005, 2 Pages, [Retrieved on Aug. 1, 2017] Retrieved from URL: https://en.wikipedia.org/w/index.php?title=Maximum_a_posteriori_estimation&oldid=26878808.
Wikipedia: "Stimulant," 17 Pages, [Retrieved on Mar. 14, 2016], Retrieved from URL: https://en.wikipedia.org/wiki/Stimulant.
Wilton L., et al., "Birth of a Healthy Infant After Preimplantation Confirmation of Euploidy by Comparative Genomic Hybridization," The New England Journal of Medicine, Nov. 22, 2001, vol. 345, No. 21, pp. 1537-1541.
Wilton L., "Preimplantation Genetic Diagnosis and Chromosome Analysis of Blastomeres Using Comparative Genomic Hybridization," Human Reproduction Update, 2005, vol. 11, No. 1, pp. 33-41.
Wright C.F., et al., "Cell-Free Fetal DNA and RNA in Maternal Blood: Implications for Safer Antenatal Testing," BMJ, Jul. 18, 2009, vol. 339, b2451, pp. 161-165.
Wright C.F., et al., "The Use of Cell-free Fetal Nucleic Acids in Maternal Blood for Non-invasive Prenatal Diagnosis," Human Reproduction Update, 2009, vol. 15, No. 1, pp. 139-151.
Wu Y.Y., et al., "Rapid and/or High-Throughput Genotyping for Human Red Blood Cell, Platelet and Leukocyte Antigens, and Forensic Applications," Clinica Chimica Acta, 2006, vol. 363, pp. 165-176.
Xia T., et al., "Thermodynamic Parameters for an Expanded Nearest-Neighbor Model for Formation of RNA Duplexes with Watson-Crick Base Pairs," Biochemistry, 1998, vol. 37, pp. 14719-14735.
Xu S., et al., "Circulating Tumor DNA Identified by Targeted Sequencing in Advanced-stage Non-small Cell Lung Cancer Patients" Cancer Letters, New York, NY, US, Nov. 12, 2015, vol. 370, No. 2, pp. 324-331, XP029337565, ISSN: 0304-3835, DOI: 10.1016/J.CANLET.2015.11.005.
Xu Y., et al., "A Mutation in the Fibroblast Growth Factor Receptor 1 Gene Causes Fully Penetrant Normosmic Isolated Hypogonadotropic Hypogonadism," The Journal of Clinical Endocrinology & Metabolism, Mar. 2007, vol. 92, No., 3, pp. 1155-1158.
Yeh I., et al., "Knowledge Acquisition, Consistency Checking and Concurrency Control for Gene Ontology (GO)," Bioinformatics, 2003, vol. 19, No. 2, pp. 241-248.
You F.M., et al., "Batchprimer3: a High Throughput Web Application for PCR and Sequencing Primer Design," BMC Bioinformatics, Biomed Central, London, GB, May 29, 2008, vol. 9, No. 1, Article No. 253, 13 Pages.
Yuan X., et al., "Probability Theory-based SNP Association Study Method for Identifying Susceptibility Loci and Genetic Disease Models in Human Case-Control Data," IEEE Trans Nanobioscience, Dec. 2010, vol. 9, No. 4, pp. 232-241 (29 Pages).
Zhang R., "Quantifying RNA Allelic Ratios by Microfluidic Multiplex PCR and Sequencing," Nature Methods, Jan. 2014, vol. 11, No. 1, pp. 51-56.
Zhao X., et al., An Integrated View of Copy No. and Allelic Alterations in the Cancer Genome Using Single Nucleotide Polymorphism Arrays, Cancer Research, May 1, 2004, vol. 64, pp. 3060-3071.
Zhong X.Y., et al., "Risk Free Simultaneous Prenatal Identification of Fetal Rhesus D Status and Sex by Multiplex Real-time PCR using Cell Free Fetal DNA in Maternal Plasma," Swiss Medical Weekly, Mar. 2001, vol. 131, pp. 70-74 (7 Pages).
Zhou W., et al., "Counting Alleles to Predict Recurrence of Early-Stage Colorectal Cancers," The Lancet, Jan. 19, 2002, vol. 359, pp. 219-225.
Zimmermann B., et al., "Noninvasive Prenatal Aneuploidy Testing of Chromosomes 13, 18, 21, X, and Y, using Targeted Sequencing of Polymorphic Loci," Prenatal Diagnosis, Dec. 2012, vol. 32, No. 13, pp. 1233-1241, DOI: 10.1002/pd.3993, Epub Oct. 30, 2012.
Zimmermann B., "Noninvasive Prenatal Aneuploidy Testing of Chromosomes 13, 18, 21, X, and Y, using Targeted Sequencing of Polymorphic Loci, Supplemental Information," Prenatal Diagnosis, 2012, vol. 32, 7 Pages.

* cited by examiner

| One Pass vs 1st & 2nd Pass Recovery | % Recovery of 100% RC | | | |
|---|---|---|---|---|
| | 72 bp | 118 bp | 194 bp | 1078 bp |
| Ctrl pH (Lysate pH 5.78) One-Pass | 89.78% | 89.97% | 86.55% | 91.06% |
| 1st Pass High pH Lysate (pH 7.17) | 5.80% | 93.57% | 88.80% | 92.87% |
| 2nd Pass Acidified Lysate (pH 5.32) | 51.76% | 0.02% | 0.08% | 0.01% |

FIG. 15

| Exp. 4 | | BB Titration | | | | | Yield Recovery (pg/µl) | | | | 1st Pass % Recovery % Recovery of 100% RC | | | |
|---|---|---|---|---|---|---|---|---|---|---|---|---|---|---|
| # | PKDB | Binding Buffer | Wash Conditions | Column | Spike | Filt. (min) | 72 bp | 118 bp | 194 bp | 1078 bp | 72 bp | 118 bp | 194 bp | 1078 bp |
| 1 | 6.5 mL + PK | 3 mL BB | WB1, WB2, EtOH | Sigma | 200pg | 6 | 0.005 | 0.045 | 0.392 | 0.917 | 0.16% | 1.38% | 12.00% | 28.04% |
| 2 | 6.5 mL + PK | 3 mL BB | WB1, WB2, EtOH | Sigma | 200pg | 6 | 0.006 | 0.110 | 0.710 | 1.377 | 0.19% | 3.38% | 21.75% | 42.11% |
| 3 | 6.5 mL + PK | 3.5 mL BB | WB1, WB2, EtOH | Sigma | 200pg | 6 | 0.006 | 0.135 | 0.861 | 1.345 | 0.20% | 4.15% | 26.38% | 41.11% |
| 4 | 6.5 mL + PK | 3.5 mL BB | WB1, WB2, EtOH | Sigma | 200pg | 6 | 0.007 | 0.160 | 0.946 | 1.605 | 0.22% | 4.93% | 28.99% | 49.06% |
| 5 | 6.5 mL + PK | 4 mL BB | WB1, WB2, EtOH | Sigma | 200pg | 6 | 0.007 | 0.132 | 0.838 | 1.467 | 0.21% | 4.07% | 25.69% | 44.84% |
| 6 | 6.5 mL + PK | 4 mL BB | WB1, WB2, EtOH | Sigma | 200pg | 7 | 0.009 | 0.250 | 1.418 | 1.991 | 0.28% | 7.70% | 43.44% | 60.89% |
| 7 | 6.5 mL + PK | 4.5 mL BB | WB1, WB2, EtOH | Sigma | 200pg | 8 | 0.010 | 0.331 | 1.568 | 2.095 | 0.32% | 10.21% | 48.04% | 64.05% |
| 8 | 6.5 mL + PK | 4.5 mL BB | WB1, WB2, EtOH | Sigma | 200pg | 6.5 | 0.014 | 0.523 | 1.679 | 2.029 | 0.43% | 16.12% | 51.44% | 62.05% |
| 9 | 6.5 mL + PK | 5 mL BB | WB1, WB2, EtOH | Sigma | 200pg | 8.5 | 0.011 | 0.518 | 1.773 | 2.146 | 0.36% | 15.95% | 54.31% | 65.60% |
| 10 | 6.5 mL + PK | 5 mL BB | WB1, WB2, EtOH | Sigma | 200pg | 7 | 0.022 | 0.950 | 2.071 | 2.307 | 0.69% | 29.24% | 63.47% | 70.55% |
| 11 | 6.5 mL + PK | 5.5 mL BB | WB1, WB2, EtOH | Sigma | 200pg | 9 | 0.020 | 0.979 | 2.015 | 2.244 | 0.64% | 30.15% | 61.73% | 68.62% |
| 12 | 6.5 mL + PK | 5.5 mL BB | WB1, WB2, EtOH | Sigma | 200pg | 7 | 0.021 | 0.859 | 1.590 | 1.795 | 0.68% | 26.44% | 48.71% | 54.87% |

FIG. 17

| Exp. 5 | | BB Titration, pH Adjusted | | | | | Yield Recovery (pg/μl) | | | | 1st Pass % Recovery | | | |
| | | | | | | | | | | | % Recovery of 100% RC | | | |
| # | PKDB | Binding Buffer | Wash Conditions: | Column | Spike: | Filt. (min) | 72 bp | 118 bp | 194 bp | 1078 bp | 72 bp | 118 bp | 194 bp | 1078 bp |
|---|---|---|---|---|---|---|---|---|---|---|---|---|---|---|
| 1 | 6.5 mL + PK | 5 mL BB (normal) | WB1, WB2, EtOH | Sigma | 200pg | 7.25 | 0.014 | 0.568 | 1.868 | 1.948 | 0.39% | 16.03% | 52.74% | 55.20% |
| 2 | 6.5 mL + PK | 5 mL BB (normal) | WB1, WB2, EtOH | Sigma | 200pg | 9 | 0.014 | 0.576 | 2.134 | 2.350 | 0.40% | 16.25% | 60.22% | 66.59% |
| 3 | 6.5 mL + PK | 4 mL BB (pH 9) | WB1, WB2, EtOH | Sigma | 200pg | 9 | 0.006 | 0.027 | 0.421 | 1.408 | 0.18% | 0.77% | 11.89% | 39.90% |
| 4 | 6.5 mL + PK | 4 mL BB (pH 9) | WB1, WB2, EtOH | Sigma | 200pg | 7.25 | 0.005 | 0.031 | 0.659 | 1.727 | 0.15% | 0.87% | 18.59% | 48.93% |
| 5 | 6.5 mL + PK | 4.5 mL BB (pH 9) | WB1, WB2, EtOH | Sigma | 200pg | 7 | 0.005 | 0.052 | 0.932 | 2.098 | 0.16% | 1.45% | 26.30% | 59.45% |
| 6 | 6.5 mL + PK | 4.5 mL BB (pH 9) | WB1, WB2, EtOH | Sigma | 200pg | 6.25 | 0.005 | 0.043 | 0.889 | 1.894 | 0.13% | 1.22% | 25.09% | 53.69% |
| 7 | 6.5 mL + PK | 5 mL BB (pH 9) | WB1, WB2, EtOH | Sigma | 200pg | 6.5 | 0.007 | 0.081 | 1.360 | 2.318 | 0.19% | 2.27% | 38.38% | 65.69% |
| 8 | 6.5 mL + PK | 5 mL BB (pH 9) | WB1, WB2, EtOH | Sigma | 200pg | 6.25 | 0.006 | 0.049 | 1.024 | 2.098 | 0.16% | 1.39% | 28.90% | 59.45% |
| 9 | 6.5 mL + PK | 5.5 mL BB (pH 9) | WB1, WB2, EtOH | Sigma | 200pg | 7.25 | 0.007 | 0.125 | 1.863 | 2.739 | 0.21% | 3.54% | 52.60% | 77.61% |
| 10 | 6.5 mL + PK | 5.5 mL BB (pH 9) | WB1, WB2, EtOH | Sigma | 200pg | 6.75 | 0.006 | 0.132 | 1.746 | 2.478 | 0.18% | 3.73% | 49.29% | 70.24% |
| 11 | 6.5 mL + PK | 6 mL BB (pH 9) | WB1, WB2, EtOH | Sigma | 200pg | 6.25 | 0.008 | 0.230 | 1.848 | 2.664 | 0.23% | 6.49% | 52.15% | 75.49% |
| 12 | 6.5 mL + PK | 6 mL BB (pH 9) | WB1, WB2, EtOH | Sigma | 200pg | 9 | 0.010 | 0.231 | 2.158 | 2.977 | 0.28% | 6.51% | 60.92% | 84.37% |
| 13 | N/A | N/A | N/A | N/A | None.RC | | 3.479 | 3.524 | 3.513 | 3.504 | | | | |
| 14 | N/A | N/A | N/A | N/A | None.RC | | 3.533 | 3.570 | 3.572 | 3.553 | | | | |

FIG. 18

Exp. 7

| # | PKDB | 1st/2nd Pass Binding Conditions | Wash Conditions | Column | Spike | Yield Recovery (pg/μL) 72 bp | 118 bp | 194 bp | 1078 bp | % Recovery of 100% RC 72 bp | 118 bp | 194 bp | 1078 bp | |
|---|---|---|---|---|---|---|---|---|---|---|---|---|---|---|
| 1 | 6.5 mL | Stock BB, 23.5mL (Control) | WB1, WB2, EtOH | Sigma | 200pg | 1.382 | 3.377 | 3.235 | 2.959 | 32.20% | 76.58% | 71.96% | 67.33% | 1st Pass |
| 2 | 6.5 mL | 4mL BB (pH9), no NAS | WB1, WB2, EtOH | Sigma | 200pg | 0.005 | 0.007 | 0.143 | 0.411 | 0.11% | 0.15% | 3.18% | 9.35% | 2nd Pass |
| 3 | 6.5 mL | 4mL BB (pH9), no NAS + 19.5mL Stock BB | WB1, WB2, EtOH | Sigma | 200pg | 0.951 | 2.880 | 2.407 | 2.241 | 22.16% | 65.31% | 53.54% | 50.99% | |
| 4 | 6.5 mL | 4mL BB (pH9) | WB1, WB2, EtOH | Sigma | 200pg | 0.007 | 0.025 | 0.264 | 1.350 | 0.16% | 0.56% | 5.88% | 30.72% | 1st Pass |
| 5 | 6.5 mL | 4mL BB (pH9) + 19.5 mL Stock BB | WB1, WB2, EtOH | Sigma | 200pg | 3.706 | 3.707 | 3.517 | 2.468 | 86.33% | 84.08% | 78.22% | 56.17% | 2nd Pass |
| 6 | None | None | None | None | None. RC | 4.292 | 4.409 | 4.496 | 4.394 | | | | | |

Recovery of All 72, 118, 194 bp in 2nd Pass

Loss of some 1078 bp to 1st Pass pH 9 shows more discrimination than pH 10

Exp# 8

| # | PKDB | Binding Buffer | Wash Conditions | Column | Spike | Yield Recovery (pg/μL) 72 bp | 118 bp | 194 bp | 1078 bp | % Recovery of 100% RC 72 bp | 118 bp | 194 bp | 1078 bp | |
|---|---|---|---|---|---|---|---|---|---|---|---|---|---|---|
| 1 | 6.5 mL | Pilot Lot BB (23.5 mL) | WB1, WB2, EtOH | Sigma | 200pg | 3.469 | 3.368 | 3.336 | 3.276 | 89.43% | 90.78% | 86.02% | 91.11% | 1st Pass |
| 2 | 6.5 mL | Pilot Lot BB (23.5 mL) | WB1, WB2, EtOH | Sigma | 200pg | 3.349 | 3.300 | 3.318 | 3.201 | 86.33% | 88.95% | 85.57% | 89.03% | 2nd Pass |
| 3 | 6.5 mL | 4 mL BB (pH 9) | WB1, WB2, EtOH | Sigma | 200pg | 0.004 | 0.021 | 0.312 | 0.622 | 0.10% | 0.57% | 8.03% | 17.29% | |
| 4 | 6.5 mL | 4 mL BB (pH 9) + 19.5 mL BB + additional MES | WB1, WB2, EtOH | Sigma | 200pg | 3.202 | 3.095 | 2.716 | 2.350 | 82.56% | 83.42% | 70.05% | 65.37% | 1st Pass |
| 5 | 6.5 mL | 4.5 mL BB (pH 10) | WB1, WB2, EtOH | Sigma | 200pg | 0.003 | 0.004 | 0.006 | 0.097 | 0.08% | 0.11% | 0.15% | 2.70% | 2nd Pass |
| 6 | 6.5 mL | 4 mL BB (pH 10) + 19.5 mL BB + additional MES | WB1, WB2, EtOH | Sigma | 200pg | 3.208 | 3.043 | 3.072 | 2.948 | 82.70% | 82.04% | 79.23% | 82.01% | |
| 7 | None | None | None | None | None. RC | 3.879 | 3.710 | 3.878 | 3.595 | | | | | |

FIG. 19

| Case# | Condition: | Lysate pH: | 72 bp | 118 bp | 194 bp | 1078 bp | CFE % | Increase | Noise Parameter |
|---|---|---|---|---|---|---|---|---|---|
| 1 | Ctrl | | | | | | 11.82% | 0% | 1116.29 |
| 1 | 2nd Pass | 5.53 | 86.20% | 74.50% | 11.54% | 0.97% | 13.63% | 1.80% | 674.87 |
| 1 | 1st Pass | 6.65 | 0.22% | 2.23% | 61.30% | 93.05% | 10.32% | -1.50% | 991.34 |
| 2 | Ctrl | | | | | | 12.73% | 0% | 961.70 |
| 2 | 2nd Pass | 5.54 | 80.46% | 50.03% | 0.27% | 0.10% | 17.84% | 5.11% | 400.96 |
| 2 | 1st Pass | 6.51 | 0.23% | 9.56% | 76.77% | 94.23% | 10.92% | -1.80% | 1078.57 |
| 3 | Ctrl | | | | | | 6.31% | 0% | 1269.59 |
| 3 | 2nd Pass | 5.57 | 75.05% | 35.55% | 0.17% | 0.03% | 18.14% | 11.82% | 1521.75 |
| 3 | 1st Pass | 6.52 | 0.39% | 24.44% | 78.40% | 94.52% | 4.41% | -1.90% | 1185.28 |
| 4 | Ctrl | | | | | | 12.42% | 0% | |
| 4 | 2nd Pass | 5.51 | 70.31% | 19.72% | 0.11% | 0.04% | 22.14% | 9.72% | 1229.91 |
| 4 | 1st Pass | 6.52 | 0.54% | 42.84% | 86.91% | 90.30% | 11.02% | -1.40% | 1181.51 |
| 5 | Ctrl | | | | | | 11.32% | 0% | 377.16 |
| 5 | 2nd Pass | 5.57 | 82.87% | 52.56% | 0.29% | 0.02% | 20.44% | 9.12% | 1073.34 |
| 5 | 1st Pass | 6.52 | 0.37% | 5.79% | 39.80% | 95.22% | 7.92% | -3.41% | 1188.08 |
| 6 | Ctrl | | | | | | 11.02% | 0% | 449.49 |
| 6 | 2nd Pass | 5.59 | 84.91% | 53.34% | 0.93% | 0.07% | 15.43% | 4.41% | 1109.95 |
| 6 | 1st Pass | 6.46 | 0.45% | 21.42% | 89.94% | 94.07% | 9.72% | -1.30% | 1555.92 |
| 7 | Ctrl | | | | | | 5.31% | 0% | 438.50 |
| 7 | 2nd Pass | 5.67 | 71.15% | 49.38% | 0.49% | 0.01% | 7.41% | 2.10% | 909.70 |
| 7 | 1st Pass | 6.46 | 0.33% | 13.92% | 91.82% | 95.02% | 4.51% | -0.80% | 1293.68 |
| 8 | Ctrl | | | | | | 3.91% | 0% | 764.09 |
| 8 | 2nd Pass | 5.63 | 78.89% | 62.76% | 8.27% | 0.01% | 4.51% | 0.60% | 1106.80 |
| 8 | 1st Pass | 6.44 | 0.26% | 10.46% | 72.30% | 92.41% | 3.41% | -0.50% | 1366.13 |
| 9 | Ctrl | | | | | | 9.12% | 0% | 859.89 |
| 9 | 2nd Pass | 5.63 | 68.93% | 62.91% | 45.93% | 0.11% | 12.02% | 2.91% | 1118.86 |
| 9 | 1st Pass | 6.4 | 0.29% | 3.51% | 15.81% | 93.97% | 5.11% | -4.01% | 797.03 |
| 10 | Ctrl | | | | | | 5.01% | 0% | 1036.26 |
| 10 | 2nd Pass | 5.6 | 78.97% | 73.01% | 23.85% | 0.03% | 5.81% | 0.80% | 1294.70 |
| 10 | 1st Pass | Recal 6.3 | 0.30% | 2.42% | 50.70% | 94.88% | 3.71% | -1.30% | 1161.90 |
| 11 | Ctrl | | | | | | 6.01% | 0% | 996.13 |
| 11 | 2nd Pass | 5.64 | 80.24% | 81.00% | 62.28% | 0.02% | 6.81% | 0.80% | 811.84 |
| 11 | 1st Pass | 6.33 | 0.27% | 1.51% | 14.12% | 93.14% | 3.71% | -2.30% | 665.82 |
| 12 | Ctrl | | | | | | 23.25% | 0% | 616.96 |
| 12 | 2nd Pass | 5.55 | 71.63% | 69.17% | 55.14% | 0.01% | 24.35% | 1.10% | 478.02 |
| 12 | 1st Pass | 6.31 | 0.29% | 0.91% | 7.62% | 95.07% | 18.94% | -4.31% | |

NSI-SSAP: Concentrations in the Low Stringency Binding Condition (lysate volume = 21.9 mL)

| Compontent | Concentration in Low Stringency Binding Condition | Weight in Low Stringency Binding Condition | Percent* in Low Stringency Binding Condition |
|---|---|---|---|
| Human Plasma | 45.66% (v/v) | na | 46.66% (v/v) |
| Tris-base | 20 mM | 0.053 g | 0.242% (w/v) |
| Guanidine-Cl | 3.2055M | 6.706 g | 30.622% (w/v) |
| EDTA | 0.8014 mM | 0.005129 g | 0.023% (w/v) |
| Tween 20 | 5.34% (v/v) | na | 5.34% (v/v) |
| Acetonitrile | 8.013% (v/v) | na | 8.0103% (v/v) |

NSI-SSAP: Concentrations in the High Stringency Binding Condition (lysate volume = 43.9 mL)

| Compontent | Concentration in High Stringency Binding Condition | Weight in High Stringency Binding Condition | Percent* in High Stringency Binding Condition |
|---|---|---|---|
| Human Plasma (10mL) | 22.78% (v/v) | na | 22.78% (v/v) |
| Tris-base | 10 mM | 0.053 g | 0.121% (w/v) |
| Guanidine-Cl | 3.2031 M | 13.4328 g | 30.5986% (w/v) |
| EDTA | 0.726 mM | 0.009257 g | 0.0211% (w/v) |
| EtOH | 0.65% (v/v) | na | 0.65% (v/v) |
| MES | 29.3 mM | 0.25113 g | 0.572% (w/v) |
| Tween 20 | 5.17 (v/v) | na | 5.17% (v/v) |
| Acetonitrile | 21.537% (v/v) | na | 21.537% (v/v) |

*Percentages listed variably as weight per volume (w/v) or volume per volume (v/v) and thus do not sum to 100%.

METHODS FOR ISOLATING NUCLEIC ACIDS WITH SIZE SELECTION

CROSS-REFERENCE TO RELATED APPLICATIONS

This application is a National Stage Entry of PCT/US19/18274, filed Feb. 15, 2019, which claims the benefit of U.S. Provisional Application Ser. No. 62/631,336, filed Feb. 15, 2018, and PCT Application Ser. No. PCT/US2018/18425, filed Feb. 15, 2018. PCT Application Serial No. PCT/US2018/18425 claims the benefit of U.S. Provisional Application Ser. No. 62/461,735, filed Feb. 21, 2017. Each of these applications cited above is hereby incorporated by reference in its entirety.

BACKGROUND

Non-invasive and minimally invasive liquid biopsy tests utilize sample material collected from external secretions or by needle aspiration for analysis. The extracellular nuclear DNA present in the cell-free fraction of bodily fluids such as urine, saliva and other glandular secretions, cerebrospinal and peritoneal fluid, and plasma or serum from blood, contain sufficient amounts of target sequences to support accurate detection of genetic anomalies that underlie many disorders that could otherwise be difficult or impossible to diagnosis outside of expensive medical biopsy procedures bearing substantial risk. In blood, the circulating cell free DNA (cfDNA) fraction represents a sampling of nucleic acid sequences shed into the blood from numerous sources which are deposited there as part of the normal physiological condition. The origin of a majority of cfDNA can be traced to either hematological processes or steady-state turnover of other tissues such as skin, muscle, and major organ systems. Of great clinical importance was the discovery that a significant and detectable fraction of cfDNA derives from exchange of fetal DNA crossing the placental boundary and from immune-mediated, apoptotic or necrotic cell lysis of tumor cells or cells infected by viruses, bacterium, or intracellular parasites. This makes plasma an extremely attractive specimen for molecular analytical tests and in particular, test that leverage the power of deep sequencing for diagnosis and detection.

Physical separation by molecular sieving has been exploited many times and in many ways to characterize DNA. The most common sieving techniques that separate DNA by size are electrophoretic in nature. These include native fragment analysis in agarose gels or capillary electrophoresis (CE) through polymer supports, or denaturing methods in polyacrylamide-urea gels or through urea polymer CE, so extensively used in Maxim-Gilbert and Sanger sequencing. Chromatographic separation of DNA using ion exchange (IE) or reverse phase (RP) supports is also widely used to characterize or purify DNA. IE and RP methods are routinely used to separate conjugates from non-conjugates and unincorporated label following covalent modification with for example, reactive amines, sulfhydril or azido groups, and ligands such as biotin or fluorescent dyes. These techniques depend on the chemical differences imparted by the presence of the particular substituent, which typically alter charge and/or hydrophobicity of the DNA-adduct relative to unlabeled DNA. Molecular sieving and chromatographic techniques rely on physical-hydrodynamic differences associated with DNA length, or chemical-physical difference associated with covalent modification.

There are other techniques that achieve size dependent fractionation of native DNA based on size, that do not depend on sieving or chemical differences, but which operate by differential adsorption to solid supports. The most famous and highly applied approach is Solid Phase Reversible Isolation (SPRI) selection which utilizes carboxyl coated paramagnetic beads in the presence of high salt and the crowding agent polyethylene glycol (PEG), to promote controlled adsorption, tuned for a given size by the varying PEG concentrations. DNA molecules of differing length can be partitioned by subjecting source DNA to various binding and elution schemes in the presence of different amounts of PEG. This size selection method is routinely applied to separate PCR primers or un-ligated adapters smaller in size than PCR amplified or ligation products. It has also been used to fractionate sheared genomic DNA (gDNA) and even "clean up" purified cell-free DNA (cfDNA) by removing larger contaminating gDNA prior to molecular analysis or sequencing library preparation. In all cases, the input for SPRI-based selection fit one or more of the following criterion: (1) the input DNA has already been purified from the biological sample; (2) the volume is relatively small (e.g., 50 to 100 µL); and/or (3) the DNA exists in a defined composition (e.g., highly pure in buffer, or in reaction conditions such as end repair, ligation, PCR amplification, etc.).

SUMMARY

Disclosed here is a purification size selection method that is performed concomitant with nucleic acid isolation directly from a complex biological sample as the first step in sample preparation for molecular analysis. The does not require the input of previously purified DNA to achieve fine discrimination in the small DNA size regime (50 to 300 bp), and can be adjusted for large volume (10 to 20 mL) of liquid sample (e.g., human plasma, serum, or urine). The method is based on selective adsorption to a solid support. The workflow described herein encompasses simultaneous purification and size selection of cfDNA by sequential low and high stringency binding and elution, and is comprised of the following elements; (1) proteolysis and establishment of a low stringency binding condition; (2) DNA immobilization, washing, and first elution; (3) establishment of a high stringency binding condition; and (4) DNA immobilization, washing, and second elution. The size distribution of cfDNA preserved in the first and second elution reflects the differential binding affinity of long versus short dsDNA fragments that is dependent on the underlying low and high stringency binding conditions established. The net result is a partitioning of longer cfDNA fragments to the first eluate and shorter cfDNA to the second eluate. Both are preserved in the process and due to the extremely high capture efficiency, little loss of the starting DNA from the sample is lost, and therefore all molecules can be processed for analysis post purification/selection.

Accordingly, in one aspect, the inventions described herein relate to a method for isolating nucleic acids from a biological sample, comprising: (a) contacting a first composition comprising nucleic acids obtained from a biological sample with a first matrix under a low-stringency binding condition that comprises less than 1% aliphatic alcohols, that binds less than 5% of nucleic acids of about 72 bp or shorter and more than 30% of nucleic acids of about 194 bp or longer to the first matrix; and (b) contacting a second composition comprising remainder of the first composition with a second matrix under a high-stringency binding condition that also comprises less than 1% aliphatic alcohols, that binds more than 70% of nucleic acids of about 72 bp or longer and more than 30% of nucleic acids of about 50 bp or longer to the second matrix.

In another aspect, the inventions described herein relate to a kit for isolating nucleic acids from a biological sample, comprising (a) a first binding buffer for establishing a low-stringency binding condition that comprises less than 1% aliphatic alcohols, that binds less than 5% of nucleic acids of about 72 bp or shorter and more than 30% of nucleic acids of about 194 bp or longer to a matrix, and (b) a second binding buffer for establishing a high-stringency binding condition that also comprises less than 1% aliphatic alcohols, that binds more than 70% of nucleic acids of about 72 bp or longer and more than 30% of nucleic acids of about 50 bp or longer to the matrix.

These and other features, together with the organization and manner of operation thereof, will become apparent from the following detailed description when taken in conjunction with the accompanying drawings.

BRIEF DESCRIPTION OF THE DRAWINGS

FIG. 15 shows data from a proof-of-concept experiment in which the second passage of acidified lysate was able to recover small fragments missed in the first passage.

FIG. 17 shows data from an experiment that tested low stringency binding conditions by uniform titration of binding buffer to progressively increase the stringency. The proteolysis conditions (PKDB+PK) are kept the same.

FIG. 18 shows data from an experiment that tested increasing the pH of the low stringency binding condition. The pH 9 adjusted binding buffer (BB) promoted improved matrix retention of fragments 194 and 1078 bp in length, but did not retain fragments 72 and 118 bp in length compared to: compare $1^{st}$ pass recovery of the 118 bp fragment of rows 1 and 2 with that of rows 7 and 8, where both received 5 mL of BB at the normal pH and at pH 9, respectively.

FIG. 19 shows (top) data from an experiment that tested low stringency binding-high stringency binding system with ACN or without ACN Rows 3 and 5 show the improved $2^{nd}$ pass recovery of the 72, 118 and 194 bp fragments in the presence of ACN. The bottom table show data from an experiment that tested further increasing the pH of the low stringency binding-high stringency binding system that suggest better $1^{st}$ pass retention of the larger 1078 bp fragment with pH 9 binding buffer (row 3 vs row 5).

FIG. 22 tabulates child fraction estimate (CFE) from the experiment shown in FIG. 20, applying the two-step filtration method to preferentially enrich for fetal cfDNA from 12 plasma samples from pregnant mothers. Nearly all 72 bp fragments in are captured in second pass eluate, while almost no 194 bp and 1078 bp fragments are captured in second pass eluate. % CFE increased in second pass eluate.

FIG. 27 shows a table of compositions for low and high stringency binding conditions for the methods depicted in FIG. 26 and FIG. 31, and tested throughout FIGS. 28 to 35. The upper table lists components and concentrations established with low stringency buffer (LSBB) when added to plasma or library products in the proportions described in FIGS. 26 and 31. The lower table lists components and concentrations established following addition of high stringency HSBB to lysates recovered following $1^{st}$ Pass vaccum or $1^{st}$ Spin Column filtration.

FIG. 36 depicts such a strategy for adding a length of 25 bp to each library product by tailing PCR. As depicted, one round of PCR with primers F1/R1-LibAddition would add ~50 bp. Another ~50 bp would then be added to the F1/R1-LibAdditon long product in a subsequent round of amplification with primers F2/R2-LibAddition. Under the scenario depicted, the cutoff for cfDNA fragments selected in the Small Library Fraction would be <~200 bp for F1/R1 products and <~150 bp for the F2/R2 products. Given that the underlying cfDNA fragments preserved in original libraries are ~166 bp, (incidentally in close agreement with data in FIG. 33 (~229−63=166 bp)). This means that size selection of the F1/R1-LibAddition products would shift the average cutoff to <~116 bp and further to a cutoff of <~66 bp if applied to the F2/R2-LibAdditon products.

DETAILED DESCRIPTION

Figure 1:
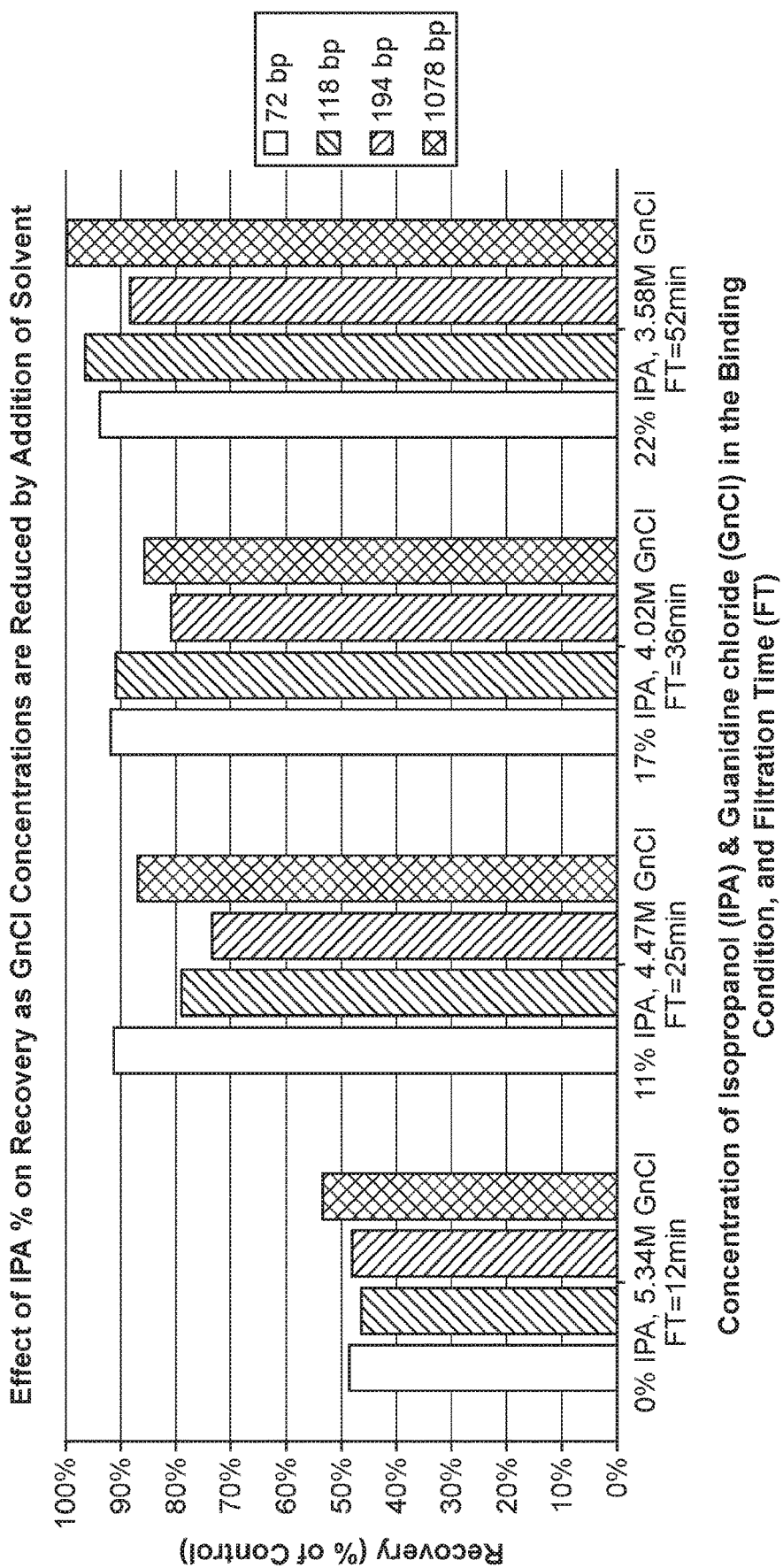
FIG. 1 shows recovery of DNA as a function of the concentration of isopropanol (IPA) and guanidine chloride (GnCl) in the nucleic acid binding state. Recovery of short dsDNA increased as the IPA concentration was raised and GnCl concentrations fell as a certain amount of volume was displaced by the added solvent. Exogenous DNA targets were spiked after plasma proteolysis and quantified by real time PCR and standard curve methods. Percent recovery of target fragments was determined by comparing against spike controls assembled by adding the original spike amount to eluates recovered from matched plasma samples by DNA isolation methods similar to the test method. Each test sample was normalized with buffer to account for the volume of spike targets added to recovery controls.

Reference will now be made in detail to some specific embodiments of the invention contemplated by the inventors for carrying out the invention. Certain examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details.

Various techniques and mechanisms of the present invention will sometimes be described in singular form for clarity. However, it should be noted that some embodiments include multiple iterations of a technique or multiple instantiations of a mechanism unless noted otherwise.

Introduction

Characteristics of cfDNA in the circulation. The half-life of cfDNA can be longer than naked DNA spiked into fresh, unpreserved, plasma or when injected into the bloodstream in vivo. This can be due to the fact that circulating nuclear DNA remains in tight association with core and linker histones which protect two wraps or gyres of DNA, in mononucleosomes and chromatosomes, from active nucleases in blood or plasma, thus preserving fragments of ~130 to ~170 base pairs (bp) in length. Fragments of two or three times this length can also be recovered from plasma, demonstrating that oligonucleosomes and oligochromatosomes can exist in the circulation as well. In addition to chromatinized DNA, both DNA and various RNA species survive for a substantial length of time in the circulation within membrane bound microvesicles (exosomes), actively shed by cells via exocytosis and blebbing. The steady-state concentration of circulating cell free DNA (cfDNA) fluctuates in the ng/mL range, and reflects the net balance between release of fragmented chromatin into the bloodstream and the rate of clearance by nucleases, hepatic uptake and cell mediated engulfment. Normal and health compromised individuals, exhibit cfDNA concentrations averaging 1 and 40 ng/mL of plasma (*J. Clin. Inv.* (1975) 56:512). No single source or mechanism can explain from where or how such short chromatin bits enter the circulation with such regularity, but as discussion, the process is dominated by erythrocytic apoptosis in the blood and bone marrow. Lesser contributions from apoptotic, necrotic and traumatic cell death, coupled with macrophage destruction throughout the body (*Cancer. Res*. (2001) 61:1659) spill cfDNA sequences into the blood that potentially include rare variants indicative of latent disease or serious fetal genetic anomalies. When coupled to the power of next generation genetic testing, cfDNA can provide unprecedented access to genetic information from disease states that might elude conventional detection, or where the site of origin is inaccessible to biopsy. Accurate and early detection of tumor associated genetic mutation, rearrangements, copy number variation, insertions/deletions or fusions is possible through deep analysis of cfDNA from plasma.

Preservation of cfDNA for genetic analysis. The key to liquid biopsy approaches which target cfDNA, is the ability to bind and purify sufficient quantities of the highly fragmented DNA from blood plasma collected by needle stick, typically from an arm vein. With respect to non-invasive prenatal testing and cancer detection, a huge problem is presented by the fact that an overwhelming majority of cfDNA in blood comes from normal cells. This background of normal DNA dilutes the far scarcer fragments originating from the developing fetus or tumor cells. Thus care needs to be taken to preserve circulating nucleosomes from the time of blood collection to sample processing, and to prevent or minimize further dilution of cfDNA by genomic DNA released by lysis of nucleated cells. Such precautions begin at blood collection with the utilization of blood collection tubes (BCT's) which contain anticlotting and cell stabilizing agents which prevent lysis of mononuclear cells during storage for up to 14 days. To compensate for the low endogenous levels of cfDNA in plasma and to improve the odds of sampling a comparatively rare population of sequences of interest, tests routinely call for the processing of large volumes, up to 10 mL, of plasma through DNA extraction methods. This necessitates collection of at least two 10 mL blood samples to generate one 10 mL plasma sample. The present invention describes methods for release of bound cfDNA from nucleoprotein complexes contained in human plasma and the high efficiency capture and recovery (>85-95%) of the liberated cfDNA fragments from 10 mL of plasma. The method is extendable to isolation of cfDNA from serum and other body fluids.

DNA Extraction from large volume plasma samples. The isolation and purification of cfDNA from plasma poses a particular set of challenges due to the low starting concentration, matrix complexities, and the variable nature of plasma samples collected by venipuncture into vacuum tubes. Conventionally, 10 to 60 ng of cfDNA is recoverable from 10 mL of human plasma, and the average small size of DNA fragments make them difficult to capture and retain on solid supports through sequential wash steps. Plasma is a complicated fluid, and in comparison to the total mass of other macromolecular constituents (e.g., proteins, lipids and protein-lipid complexes), cfDNA represents a tiny fraction. Any successful plasma nucleic acid extraction process needs to accomplish three things to isolate cfDNA in pure form and at high rates of recovery. First, the protein complexes that serve to protect cfDNA (i.e., chromatinized DNA in the form of mono-, di-, tri-nucleosomes or longer) from nucleases need to be deconstructed to release cfDNA and expose it for capture on solid phases. Second, the macromolecular components which predominate in plasma (e.g., albumin, immunoglobulins, fibrinogen/fibrin, free hemoglobin, proteinase inhibitors, nucleases, lipids and lipoprotein complexes) need to be dissolved, degraded, solubilized, or neutralized to prevent them from interacting with released cfDNA or the capture matrix in ways that would interfere with (for example clog or foul) or reduce the efficiency of nucleic acid binding. Third, the establishment of a chemical environment, binding proficient condition or nucleic acid binding state that supports and promotes complete, preferential, stable, and reversible interaction of nucleic acids, in particular cfDNA fragments of all sizes, with the solid phase support material or capture matrix comprised of glass fiber or silica.

Release of cfDNA by proteolysis, chemical denaturation or both. The two main methods used to disrupt stable noncovalent DNA-protein interactions are chemical denaturation and enzymatic destruction. Early methods employed organic liquid phase extraction utilizing phenol and phenol-chloroform mixtures to disintegrate nucleoprotein complexes and sequester proteins and lipids into the organic phase while partitioning the highly hydrophilic DNA and RNA into the aqueous phase in very pure form. Phenol-chloroform methods proved highly efficient and delivered DNA highly suitable for enzymatic manipulation. However, user and environmental safety, ease of use considerations, and practical difficulties of scaling large volume extractions to phenol-chloroform methods have led to its replacement with safer, highly scalable solid phase methods that can more easily purify nucleic acids from almost any starting material. One of the earliest solid phase methods used to purify DNA was described by E.M. Southern (*J. Mol. Biol*. (1975) 94:51-70) where the DNA excised from agarose hydrogels was recovered following dissolution in strongly chaotropic salts, sodium perchlorate or sodium iodide (NaI), followed direct DNA capture on hydroxyapatite (mineralized calcium phosphate) particles, washed and eluted into a low ionic strength buffer. Vogelstein and Gillespie (*PNAS, USA* (1979)76:615-619) later improved upon this earliest example by substituting powdered glass for hydroxyapatite and captured DNA from bits of agarose gels dissolved in saturated NaI. Excess NaI was removed by washing glass particles in 50% buffered ethanol and the bound DNA eluted in Tris buffered saline, EDTA. This method, which utilized glass or silica as a solid support to bind nucleic acids in the presence of high salt, followed by washes in high percentage alcohol to remove contaminants, and elution in low ionic strength buffers, forms the basis for most commercial nucleic acid purification kits on the market. These safer and highly scalable methods work by exploiting the strong yet reversible hydrophilic interaction promoted between DNA and silanols and siloxanes on the surface of glass and silica (*Colloids and Surfaces, A: Physiochemical and Engineering Aspects*, (2000)173:1-38) in high salt solutions. Unlike phenol-chloroform methods which efficiently denature and strip bound proteins off DNA and simultaneously denature, solvate and move proteins, lipids and other contaminants into the organic phase, solid phase extraction methods need to deal with DNA bound proteins and background sample contaminants differently. Proteolysis of protein-DNA complexes is the most widely employed method of releasing proteins bound to DNA and for degrading other protein contaminants contained in the starting sample. Still other effective methods utilize only strong chemical denaturants to disrupt protein tertiary and secondary structure, dissociate DNA/RNA from chromatin or binding proteins, and unfold other proteins contained in the sample to greatly diminish their interference with the glass/silica solid phase during DNA capture. Boom et al. (*J*

*Clin Micro*. (1990) 28(3):495-503) were the first to detail the use of solid phase capture on powdered glass and diatomaceous silica from clinical samples such as serum and urine. Their method used a solid phase of glass or silica particles to adsorb nucleic acids from complex biological samples following direct chemical lysis in high concentrations of chaotropic salts.

Figure 8:
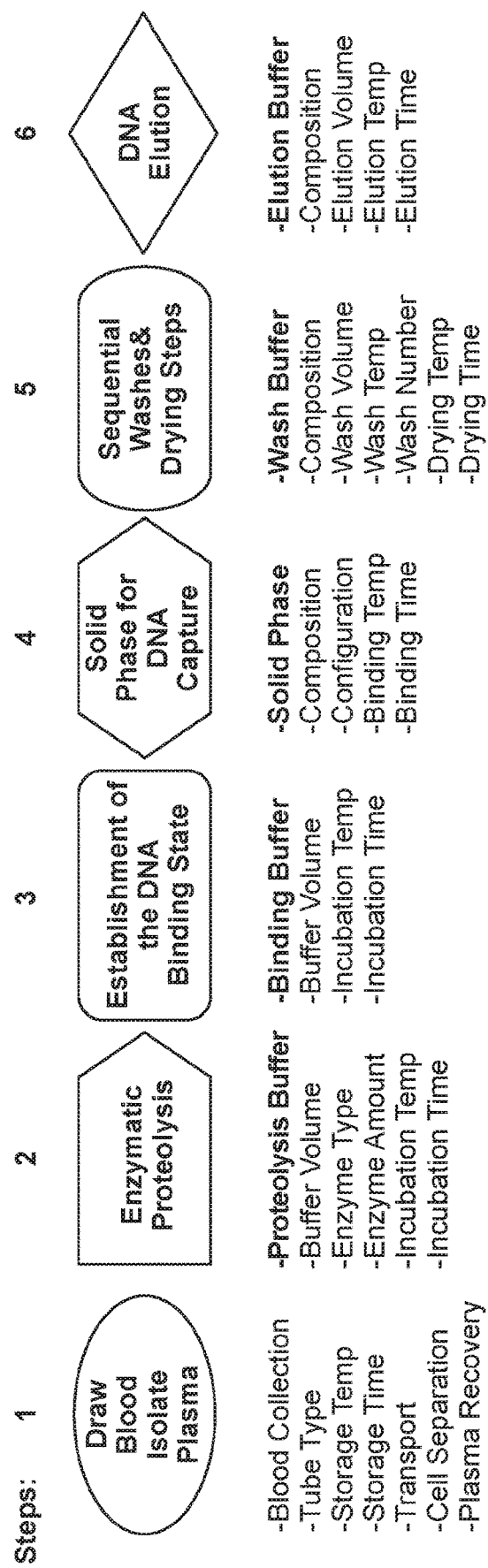
FIG. 8 shows a generalized Plasma ccfDNA Extraction Workflow.

A generalized scheme by which cfDNA can be isolated from plasma is presented in FIG. 8, which describes major effectors for each phase of the extraction. For cfDNA isolation by solid phase capture, plasma proteins and protein-DNA complexes are typically disrupted by a combination of proteolytic lysis and chemical lysis which sets up the nucleic acid binding state, a condition that necessitates the sequential, serial addition of two buffers, Proteolysis Buffer and Binding Buffer to samples, separated by an incubation step (see FIG. 8, steps 2 & 3). The constituents of Proteolysis Buffer and Binding Buffer should be optimized to effect complete proteolysis and the combination of which should establish a chemical environment that promotes highly efficient interaction of nucleic acids (DNA/RNA) with a Solid Phase or Binding Matrix (FIG. 8, step 4) such as glass fiber or silica particles. Proteinase K is the most common broad spectrum protease used for proteolytic lysis in DNA extraction methods. It is a stable serine protease that is active under a wide range of pH, temperature, salt, solvent, and detergent concentrations. The activity of Proteinase K peaks in the presence of moderate denaturants, 2-4 molar chaotropic salts and ionic detergents, which act both to stimulate enzymatic activity and increase substrate accessibility by destabilizing protein secondary structure. At completion, Proteinase K digestion will have reduced polypeptides to small di- and tri-peptides, and in the process degraded itself by autodigestion, thus eliminating the vast majority of enzyme added to samples. Proteolysis Buffer is a key additive in DNA extraction methods, and critical to DNA isolation from complex biological samples. In sample mixtures, Proteolysis Buffer is designed to preserve target nucleic acids, establish optimum conditions for proteolysis, solubilize lipids and microvesicles, breakdown colloids and particulate matter, and prevent precipitation over the course of protease reactions. Moreover, Proteolysis Buffer must be compatible with Binding Buffers which are added to samples following proteolysis in order to complete the denaturation process and establish the nucleic acid binding state (see FIG. 8, step 3). Binding Buffers act to chemically complete denaturation, quench remaining PK activity, and sets up a nucleic acid binding state that ensures high efficiency capture of short nucleic acids to silicate supports (see FIG. 8, steps 3 & 4). Available methods designed to isolate cfDNA from plasma or serum typically begin with a proteinase K lysis step initiated under moderately harsh conditions optimized for protease activity, followed by much harsher and highly denaturing chemical lysis steps optimized for DNA binding. Proteolysis Buffers and Binding Buffers serve two separate yet complimentary functions when combined with sample matrices in an ordered fashion, and form an articulated chemical system that supports high level solid phase adsorption of large and small nucleic acid fragments contained in complex biological samples.

Figure 9:
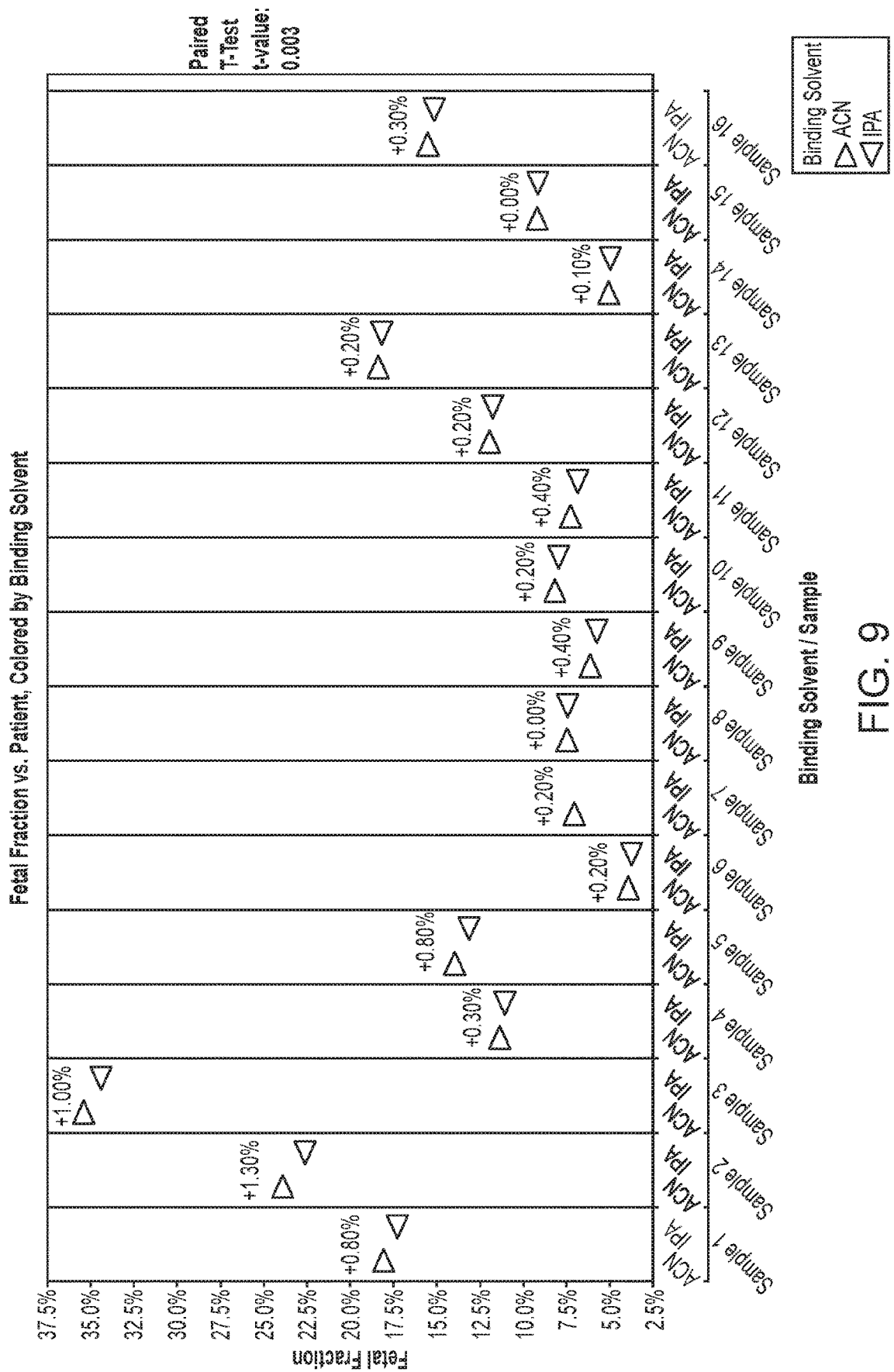
FIG. 9 Details the increased recovery of fetal cfDNA by when ACN and GnCl are present in the nucleic acid binding state, as revealed by NIPT analysis. Fetal fraction estimates derived from the ratio of fetal to maternal SNPs are shown. The pairwise comparison included 16 maternal plasma samples isolated with two different optimized methods, one utilizing acetonitrile (ACN) and one isopropyl alcohol (IPA), to establish the nucleic acid binding state. Differences in fetal fraction ((ACN)–(IPA)) are shown above each matched pair. A paired t-test reveals a statistically significant increase (t=0.003) when acetonitrile was used to establish the nucleic acid binding state.

Many next generation genetic tests utilize plasma cfDNA from a simple blood draw as an input. This patient sampling technique known as a liquid biopsy is considered a non-invasive medical procedure valuable in cancer surveillance (*J Clin Oncol*. (2014) 32(6):579-586) and detection, and prenatal health screening (*Annu Rev Genomics Hum Genet*. (2012)13:285-306). Non-invasive prenatal tests (NIPT's) which utilize cfDNA from the plasma of pregnant women to detect chromosomal aneuploidies and microdeletions that may affect child health, are prime examples of such liquid biopsy based NGS tests. Most NGS assays begin with the preservation and amplification of the very small amounts of cfDNA obtained from plasma samples in a process known as library preparation. Construction of the library immortalizes the original cfDNA isolate and uniformly multiplies the sample through a series of molecular reactions that enzymatically repair, tail, and amplify fragments to prepare them for NGS analysis. In the NIPT assay referred to herein, libraries are subject to massively multiplexed amplification reactions that amplify single nucleotide polymorphisms (SNPs) used in the genetic analysis. The amplified SNP targets are then barcoded and readied for NGS sequencing. Sequence data is processed and allelic designations for each SNP are assigned to the mother or fetus (i.e., of paternal origin) according to a bimodal mixture model of homozygous (AA) or heterozygous (AB) allele distribution (*Bioinformatics*, 28(2):2883-2890). A higher fraction of fetal cfDNA in plasma isolates leads to a greater proportion of fetal SNP's out of the total (maternal+fetal) for each target SNP detected. A higher fetal fraction produces a greater divergence between the fetal genotype and the underlying maternal genotype, and thus increases the call confidence of ploidy estimates at the chromosome and locus level. More than one factor can profoundly influence the fetal fraction in cfDNA preparations, most critical is the storage condition and anticoagulant preservative used in blood collection tubes and the time between collection and plasma isolation. Conditions that minimize lysis of leucocytes significantly reduces leakage of maternal genomic DNA into the plasma, and thereby increase the fraction of fetal cfDNA as a percentage of total. Additionally, DNA purification methods that recover the broadest range of DNA sizes, particularly small fragments <100 bp in length, will ensure yield of the highest fetal fraction. This derives from the fact that circulating fetal DNA is on average ~23 bp shorter (143 bp vs 166 bp) than maternal cfDNA (PNAS, USA (2016) 113(50) E8159-E8168). Most recent evidence, based on the analysis of ssDNA libraries, suggests that much more cfDNA shorter in length is present (*Cell* (2016) 164:57-68), but indeed much of it may be excluded by the extraction method and library construction processes themselves (*PNAS, USA* (2016) 112(11):3178-3179). Thus plasma cfDNA extraction methods that rescue short <100 bp, <75 bp, or even <50 bp cfDNA fragments may well be expected to return higher fetal fraction estimates than methods that do not. FIG. 9 compares the fetal fraction estimates from 16 paired maternal samples where plasma cfDNA was isolated with IPA or ACN used as the co-solvent to establish the nucleic acid binding state. A highly statistically significant increase in the average fetal fraction was obtained from the otherwise identical analysis treatment of the cfDNA isolated with acetonitrile compared to isopropanol. This result is surprising and it was not anticipated that an increase in fetal fraction would result from the substitution of a protic solvent such as IPA with the aprotic solvent ACN. Though highly unexpected, the increase in fetal fraction could be explained by an improve preservation and subsequent recovery of short cfDNA fragments.

Two-Step Filtration Method for Capturing cfDNA

Many embodiments described herein relate to a method for isolating nucleic acids from a biological sample, comprising: (a) contacting a first composition comprising nucleic acids obtained from a biological sample with a first matrix under a low-stringency binding condition in the presence of <1% aliphatic alcohols, that binds less than 5% of nucleic acids of about 72 bp and more than 30% of nucleic acids of about 194 bp to the first matrix; and (b) contacting a second composition comprising the remainder of the first composition with a second matrix under a high-stringency binding condition at less than 1% aliphatic alcohol, that binds more than 70% of nucleic acids of about 72 bp and more than 30% of nucleic acids of about 50 bp to the second matrix.

In some embodiments, step (a) comprises filtering the first composition through the first matrix to obtain a filtrate, and the second composition comprises the filtrate of step (a). In some embodiments, after nucleic acids are bound to the first matrix, the method further comprises washing the first matrix with a washing buffer, drying the matrix, and/or eluting nucleic acids from the first matrix with an elution buffer.

In some embodiments, step (b) comprises filtering the second composition through the second matrix. In some embodiments, after nucleic acids are bound to the second matrix, the method further comprises washing the second matrix with a washing buffer, drying the matrix, and/or eluting nucleic acids from the second matrix with an elution buffer.

In some embodiments, the method further comprises incubating the biological sample with a protease such as proteinase K prior to step (a). The biological sample can be, for example, a sample of a maternal blood, plasma, or serum. The biological sample can be, for example, a plasma sample from a pregnant woman comprising fetal cfDNA and maternal cfDNA, or a plasma sample from a cancer patient comprising circulating tumor DNA. In addition, the biological sample can comprise cfDNA selected from, for example, nucleic acids of virus, fungal or bacterial origin, as virus or virus-like particles, fungal mycelium, yeast or bacterial cells, in particle-free, cell-free, aggregate, vesicle or platelet bound forms.

In some embodiments, the first composition of step (a) is obtained by adding a first binding buffer to the biological sample after digestion by protease, wherein the first binding buffer establishes the low-stringency binding condition.

In some embodiments, the second composition of step (b) is obtained by adding a second binding buffer to the filtrate of step (a), wherein the second binding buffer establishes the high-stringency binding condition.

In some embodiments, the first and/or second binding buffer comprises a chaotropic compound and a solvent, wherein the solvent comprises a nitrile compound, tetrahydrofuran (THF), or a combination thereof.

In some embodiments, the first and/or second binding buffer comprises a nitrile compound selected from acetonitrile (ACN), propionitrile (PCN), butyronitrile (BCN), isobutylnitrile (IBCN), or a combination thereof. The first and/or second binding buffer can comprise, for example, about 15% to about 35%, or about 20% to about 30%, or about 25% of the nitrile compound (e.g., ACN).

In some embodiments, the first and/or second binding buffer comprises a chaotropic compound selected from GnCl, urea, thiourea, guanidine thiocyanate, NaI, guanidine isothiocyanate, D-/L-arginine, a perchlorate or perchlorate salt of Li+, Na+, K+, or a combination thereof. The first and/or second binding buffer can comprise, for example, about 5 M to about 8 M, or about 5.6 M to about 7.2 M, or about 6 M of the chaotropic compound (e.g., GnCl).

After the addition of the first binding buffer, the first composition can comprise, for example, about 4% to about 6%, or about 4.8% to about 5.6% of the nitrile compound (e.g., ACN). The first composition can also comprise, for example, about 3 M to about 4 M, or about 3.2 M to about 3.4 M of the chaotropic compound (e.g., GnCl).

After the addition of the second binding buffer, the second composition can comprise, for example, about 10% to about 20%, or about 13% to about 18%, or about 14% to about 15% of the nitrile compound (e.g., ACN). The second composition can also comprise, for example, about 3.5 M to about 6 M, or about 4 M to about 5 M, or about 4.3 M to about 4.5 M of the chaotropic compound (e.g., GnCl).

The pH of the first binding buffer can be, for example, about 8 to about 10, or about 8.5 to about 9.5, or about 8.9 to about 9.1, or about 9. The pH of the second binding buffer can be, for example, about 4 to about 6, or about 4.5 to about 5.5, or about 4.9 to about 5.1, or about 5. The pH of the first and/or second binding buffer can be adjusted using a buffering agent (e.g. MES or 2-(N-morpholino)ethanesulfonic acid, Tris(hydroxymethyl) aminomethane (Tris-base), or a mono, di- or tri-carboxylic acid such as formic, acetic, malonic, succinic, glutaric, citric, or malic).

In some embodiments, after the addition of the first binding buffer, the first composition can have a pH of, for example, about 7 to about 10, about 6 to about 8, or about 6 to about 7, or about 6.2 to about 6.8, or about 6.3 to about 6.7. In some embodiments, after the addition of the second binding buffer, the second composition can have a pH of, for example, about 4 to about 6, or about 5 to about 6, or about 5.3 to about 5.9, or about 5.4 to about 5.8.

In some embodiments, the first and/or second binding buffer comprises less than 5% of alcohol, or less than 2% of alcohol, or less than 1% of alcohol, or less than 0.1% of alcohol, or comprises no alcohol. In some embodiments, the first and/or second binding buffer comprises less than 5% of propanol, or less than 2% of propanol, or less than 1% of propanol, or less than 0.1% of propanol, or comprises no propanol such as isopropanol. In some embodiments, the first and/or second binding buffer comprises less than 5% of non-water protic solvents, or less than 2% of non-water protic solvents, or less than 1% of non-water protic solvents, or less than 0.1% of non-water protic solvents, or comprises no non-water protic solvents.

Alternatively, in some embodiments, the first and/or second binding buffer comprises an alcohol solvent instead of a nitrile solvent such as ACN. In some embodiments, the first and/or second binding buffer comprise isopropanol (IPA).

In some embodiments, the matrix comprises siliceous materials, silica gel, glass, glass fiber, zeolite, aluminum oxide, titanium dioxide, zirconium dioxide, kaolin, gelatinous silica, magnetic particles, ceramics, polymeric supporting materials, or a combination thereof. In a particular embodiment, the matrix comprises glass fiber. In one embodiment, the first matrix is different from the second matrix. In another embodiment, the first matrix is the same as the second matrix.

In some embodiments, the first composition and/or the second composition further comprises a chelating compound. The chelating compound can be, for example, ethylenediaminetetracceticc (EDTA), ethyleneglycol-bis(2-aminoethylether)-N,N,N',N'-tetraacetic acid (EGTA), citric acid, N,N,N',N'-Tetrakis(2-pyridylmethyl)ethylenediamine (TPEN), 2,2'-Bipyridyl, deferoxamine methanesulfonate salt (DFOM), 2,3-Dihydroxybutanedioic acid (tartaric acid), or a combination thereof. In a particular embodiment, the chelating compound is EDTA.

In some embodiments, the first composition and/or the second composition further comprises a detergent. The detergent can be, for example, Triton X-100, Tween 20, N-lauroyl sarcosine, sodium dodecylsulfate (SDS), dodecyldimethylphosphine oxide, sorbitan monopalmitate, decylhexaglycol, 4-nonylphenyl-polyethylene glycol, or a combination thereof. In a particular embodiment, the detergent is Triton X-100.

In some embodiments, the first binding buffer and/or the second binding buffer can comprise, for example, about 1% to about 6% of Triton X-100, or about 2% to about 4% of Triton X-100, or about 3% of Triton X-100. In some embodiments, after the addition of the first binding buffer, the first composition can comprise, for example, about 5% to about 6% of Triton X-100, or about 5.3% to about 5.6% of Triton X-100, or about 5.4 to about 5.5% of Triton X-100. In some embodiments, after the addition of the second binding buffer, the second composition can comprise, for example, about 4% to about 5% of Triton X-100, or about 4.2 to about 4.5% of Triton X-100, or about 4.3% to about 4.4% of Triton X-100.

The low stringency binding condition of step (a) is configured to restrict binding of shorter nucleic acid molecules while permitting binding of longer nucleic acid molecules to the matrix or solid support. In some embodiments, step (a) comprises binding less than 20%, or less than 10%, or less than 5%, or less than 2%, or less than 1% of nucleic acids of about 72 bp to the first matrix under the low-stringency binding condition. In some embodiments, step (a) comprises binding less than 70%, or less than 60%, or less than 50%, or less than 40%, or less than 30%, or less than 20%, or less than 10%, or less than 5% of nucleic acids of about 118 bp to the first matrix under the low-stringency binding condition. In some embodiments, step (a) comprises binding less than 90%, or less than 80%, or less than 70%, or less than 60%, or less than 50%, or less than 40%, or less than 30%, or less than 20% of nucleic acids of about 194 bp to the first matrix under the low-stringency binding condition. In some embodiments, step (a) comprises binding more than 20%, or more than 30%, or more than 40%, or more than 50%, or more than 60%, or more than 70%, or more than 80%, or more than 90% of nucleic acids of about 1078 bp to the first matrix under the low-stringency binding condition.

In contrast, the high stringency binding condition of step (a) is configured to facilitate binding of shorter nucleic acid molecules to the matrix or solid support. In some embodiments, step (b) comprises binding more than 40%, or more than 50%, or more than 60%, or more than 70%, or more than 80%, or more than 90% of nucleic acids of about 72 bp to the second matrix under the high-stringency binding condition. In some embodiments, step (b) comprises binding more than 40%, or more than 50%, or more than 60%, or more than 70%, or more than 80%, or more than 90% of nucleic acids of about 118 bp to the second matrix under the high-stringency binding condition. In some embodiments, step (b) comprises binding more than 40%, or more than 50%, or more than 60%, or more than 70%, or more than 80%, or more than 90% of nucleic acids of about 194 bp to the second matrix under the high-stringency binding condition. In some embodiments, step (b) comprises binding more than 50%, or more than 60%, or more than 70%, or more than 80%, or more than 90% of nucleic acids of about 1078 bp to the second matrix under the high-stringency binding condition. In some embodiments, step (b) comprises binding more than 20%, or more than 30%, or more than 40%, or more than 50%, or more than 60% or more than 70% of nucleic acids of about 50 bp to the second matrix under the high-stringency binding condition.

Figure 13:
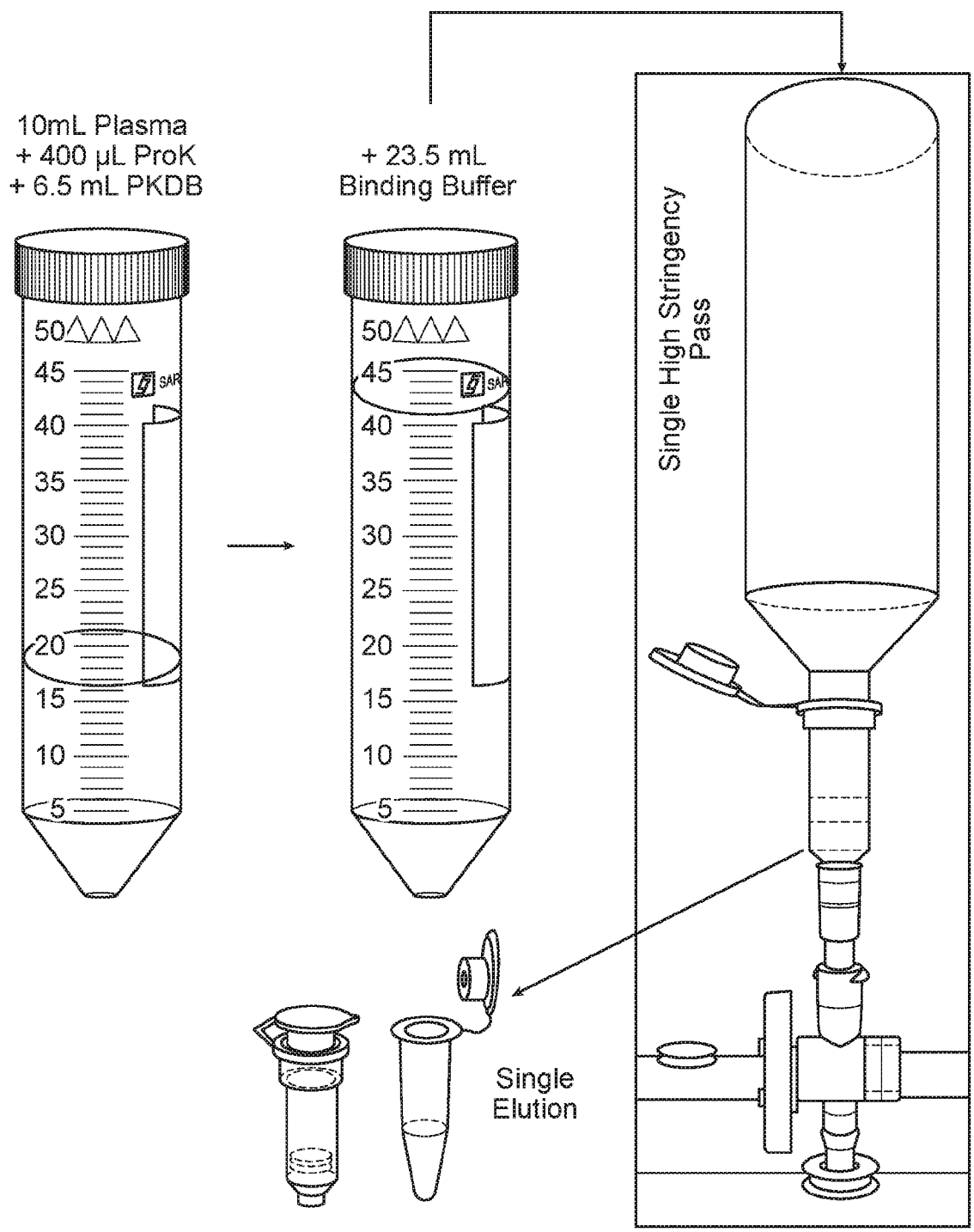
FIG. 13 shows a comparative workflow of a standard, single or one pass, cfDNA extraction process. The method shown establishes a high-stringency binding condition to isolate and purify DNA from a biological sample.

In some embodiments, the fetal fraction of nucleic acids elutable from the second matrix is at least 1%, or at least 2%, or at least 3%, or at least 5%, or at least 10% higher than fetal fraction of nucleic acids elutable from the first matrix. In some embodiments, the fetal fraction of nucleic acids elutable from the second matrix according to the two-step filtration method described herein (see e.g., FIG. 14) is at least 0.5%, or at least 0.8%, or at least 1%, or at least 2%, or at least 3%, or at least 5% higher than fetal fraction of nucleic acids elutable from a corresponding matrix according to the single-step filtration method (see e.g., FIG. 13).

In some embodiments, the method described herein does not comprise molecular sieving and chromatographic techniques. In some embodiments, the method described herein does not comprise covalent modification, conjugation, or labeling of the nucleic acids. In some embodiments, the method described herein does not comprise differential adsorption to solid supports such as Solid Phase Reversible Isolation (SPRI) selection. In some embodiments, the method described herein does not comprise use of artificial crowding agent such as polyethylene glycol (PEG), ficoll, dextran, or serum albumin.

Further embodiments described herein relate to a kit for isolating nucleic acids from a biological sample, comprising (a) the first binding buffer described herein for establishing the low-stringency binding condition for binding nucleic acids to the first matrix, and (b) the second binding buffer described herein for establishing the high-stringency binding condition for binding nucleic acids to the second matrix. In some embodiments, the kits further comprises a digestion buffer, a protease, a washing buffer, and/or an elution buffer.

Further Embodiments of Binding Composition and Binding Buffer

Many embodiments described herein relate to a composition for isolating nucleic acids from a biological sample, comprising a chaotropic compound and a solvent, wherein the solvent comprises an aprotic solvent such as a nitrile compound, tetrahydrofuran, or a combination thereof.

In some embodiments, the solvent comprises a nitrile compound. The nitrile compound can be, for example, acetonitrile (ACN), propionitrile (PCN), butyronitrile (BCN), isobutylnitrile (IBCN), or a combination thereof.

In a particular embodiment, the nitrile compound is ACN. The composition can comprise, for example, about 10% to about 20% of ACN, or about 13% to about 18% of ACN, or about 15% of ACN.

In some embodiments, the composition comprises less than 10%, or less than 5%, or less than 2%, or less than 1% of alcohol, or substantially or totally free of alcohol. In some embodiments, the composition comprises less than 10%, or less than 5%, or less than 2%, or less than 1% of propanol such as isopropanol, or substantially or totally free of isopropanol. In some embodiments, the composition comprises less than 10%, or less than 5%, or less than 2%, or less than 1% of non-water protic solvents, or substantially or totally free of non-water protic solvents. The pH of the composition can be, for example, about 4 to about 10, or about 4 to about 5, or about 5 to about 6, or about 6 to about 7, or about 7 to about 8, or about 8 to about 9, or about 9 to about 10, or about 4 to about 8, or about 4.5 to about 6, or about 4.9 to about 5.1.

The chaotropic compound can be, for example, guanidine chloride (GnCl), urea, thiourea, guanidine thiocyanate, NaI, guanidine isothiocyanate, arginine, hydrogen perchlorate or perchlorate salt of Li+, Na+, K+, or a combination thereof.

In a particular embodiment, the chaotropic compound is GnCl. The composition can comprise, for example, about 2.0 M to about 3.5 M, about 3.5 M to about 6 M of GnCl, or about 4 M to about 5 M of GnCl, or about 4.4 M of GnCl.

In some embodiments, the composition further comprises a chelating compound. The chelating compound can be, for example, ethylenediaminetetraccetic (EDTA), ethylenegly-col-bis(2-aminoethylether)-N,N,N',N'-tetraacetic acid (EGTA), citric acid, N,N,N',N'-Tetrakis(2-pyridylmethyl) ethylenediamine (TPEN), 2,2'-Bipyridyl, deferoxamine methanesulfonate salt (DFOM), 2,3-Dihydroxybutanedioic acid (tartaric acid), or a combination thereof. In a particular embodiment, the chelating compound is EDTA.

In some embodiments, the composition further comprises a detergent. The detergent can be, for example, Triton X-100, Tween 20, N-lauroyl sarcosine, sodium dodecylsulfate (SDS), dodecyldimethylphosphine oxide, sorbitan monopalmitate, decylhexaglycol, 4-nonylphenyl-polyethylene glycol, or a combination thereof.

In a particular embodiment, the detergent is Triton X-100. The composition can comprise, for example, about 3% to about 6% of Triton X-100, or about 4% to about 5% of Triton X-100, or about 4.5% of Triton X-100.

In a particular embodiment, the first binding buffer (also referred to as low-stringency binding buffer or LSBB) comprises Tris-base, a nitrile compound, a chelating compound, a detergent, and a chaotropic compound. In a further embodiment, the first binding buffer comprises Tris-base in an amount of about 10 mM to about 50 mM, the nitrile compound in an amount of about 0% to about 20%, the chelating compound in an amount of about 0 mM to about 2 mM, the detergent in an amount of about 0% to about 15%, and the chaotropic compound in an amount of about 4 M to about 8 M. In a yet further embodiment, the nitrile compound is acetonitrile, the chelating compound is EDTA, the detergent is Tween 20, and the chaotropic compound is guanidine chloride. In one preferred embodiment, the LSBB comprise between about 0 to about 20% Acetonitrile, about 0 to about 15% Tween 20, about 6 to about 7.8 molar Guanidine chloride, about 10 to about 50 mM Tris (free base), about 0 to about 2 mM EDTA (free acid), and have a pH of about 7.0 to about 10.

In a particular embodiment, the second binding buffer (also referred to as high-stringency binding buffer or HSBB) comprises MES, a nitrile compound, a detergent, an alcohol, a chaotropic compound, and a chelating compound. In a further embodiment, the second binding buffer comprises MES in an amount from about 10 mM to about 70 mM, the nitrile compound in an amount of about 10% to about 40%, the detergent in an amount from about 0% to about 10%, the alcohol in an amount of about 0 to about 2%, the chaotropic compound in an amount of about 2 M to about 4 M, and the chelating compound in an amount from about 0 mM to 2 mM. In one preferred embodiment, the HSBB may comprise between about 10 to about 40% Acetonitrile, about 0 to about 10% Tween 20, about 0 to about 2% Ethanol, about 3.2 to about 3.6 molar Guanidine chloride, about 10 to about 70 mM MES (free acid), about 0 to about 2 mM EDTA (free acid), and have a pH of about 4.05 to about 6.5.

In a particular embodiment, contacting a biological sample with a first binding buffer forms the low-stringency binding condition. In one particular embodiment, the low-stringency binding condition comprises the biological sample in an amount from about 40% to about 50%, the Tris-base in an amount from about 0.1% to about 0.3%, the chaotropic compound in an amount from about 25% to about 35%, the chelating compound from about 0% to about 0.05%, the detergent in an amount from about 0% to about 10%, and the nitrile compound in an amount from about 0% to about 10%. In one embodiment, the first binding buffer and/or the low-stringency condition has a pH of about 7.0 to 10. In one preferred embodiment, the low-stringency binding condition comprises one or more of the following: plasma (about 38.9% to about 45.66%), Acetonitrile (about 0% to about 12.1%), Tris base (about 5.43 mM to about 20 mM), Guanidine chloride (about 3.2055 M to about 4.76 M), Tween 20 (about 0% to about 9%), EDTA (about 0% to about 1.2%) and a pH of about 7 to about 9.

In a particular embodiment, contacting a biological sample with the second binding buffer forms the high-stringency binding condition. In one particular embodiment, the high-stringency binding condition comprises the biological sample in an amount from about 40% to about 50%, the Tris-base in an amount from about 0.001% to about 0.5%, the MES in an amount from about 0.1% to about 1.0%, the chaotropic compound in an amount from about 25% to about 35%, the chelating compound from about 0% to about 0.05%, the detergent in an amount from about 0% to about 10%, the alcohol in an amount from about 0.1% to about 1%, and the nitrile compound in an amount from about 10% to about 30%. In one embodiment, the second binding buffer and/or the high-stringency binding condition has a pH of about 7.0 to 10. In one preferred embodiment, the high-stringency binding condition one or more of the following: plasma (about 19.27% to about 22.78%), Acetonitrile (about 4.59% to about 26.09%), Guanidine chloride (about 3.2055 M to about 4.76 M, optionally with concentrations holding constant at low and high stringency), Tween 20 (about 0 to about 9.55%), Tris-base (about 1.22 mM to about 5.33 mM), MES (about 4.59 mM to about 38 mM), Ethanol (about 0 to about 1%), EDTA (about 0 to about 0.61 mM), and a pH of about 4.05 to about 5.5.

In some embodiments, the composition further comprises nucleic acids. The nucleic acids can comprise, for example, DNAs and/or RNAs.

The nucleic acids can comprise, for example, maternal nucleic acids or fetal nucleic acids. The nucleic acids can comprise, for example, cell free nucleic acids or circuiting tumor nucleic acids. The cell free nucleic acids may be obtained from a sample of a maternal blood, plasma, or serum. The nucleic acids can comprise, for example, DNAs or RNAs. The cell free nucleic acids can comprise, for example, cell free fetal DNA and cell free maternal DNA. The cell free DNA can comprise, for example, nucleic acids of virus, fungal or bacterial origin, as virus or virus-like particles, fungal mycelium, yeast or bacterial cells, in particle-free, cell-free, aggregate, vesicle or platelet bound forms.

The nucleic acids can be, for example, about 50 to about 1200 base pairs in length, or about 70 to about 500 base pairs in length, or about 100 to about 200 base pairs in length, or about 130 to about 170 base pairs in length.

In one particular embodiment, the cell-free DNA or circulating tumor DNA in the sample may be amplified prior to forming the low stringency binding condition. The amplification may be performed by ligating the cfDNA or the ctDNA to a plurality of DNA adapter molecules, wherein the DNA adapter molecules comprises common forward and reverse primer binding sites, and then amplifying the ligated cfDNA or ctDNA by using forward and reverse primers complementary to the common primer binding sites in the DNA adaptor molecules.

In one particular embodiment, the size of the cell-free DNA or circulating tumor DNA in the sample may be increased with trailing PCR prior to forming the low-stringency binding condition. The cell-free DNA or circulating tumor DNA may be increased with 10 bp, 15 bp, 20 bp, 25 bp, 30 bp, or 35 bp.

In some embodiments, the composition further comprises a matrix. The matrix can comprise, for example, siliceous materials, silica gel, glass, glass fiber, zeolite, aluminum oxide, titanium dioxide, zirconium dioxide, kaolin, gelatinous silica, magnetic particles, ceramics, polymeric supporting materials, or a combination thereof. In a particular embodiment, the matrix comprises glass fiber.

It was surprising and highly unexpected that such highly efficient recovery of nucleic acids, in particular cfDNA from plasma, could be achieved when protic solvents such as ethanol, propanol, or isopropanol were replaced by the aprotic solvents of the nitrile series including acetonitrile ((ACN), ethyl nitrile or methyl cyanide), propionitrile ((PCN), propyl nitrile or ethyl cyanide), butyronitrile ((BCN) butane nitrile or propyl cyanide), and isobutylnitrile ((IBCN), isobutyl nitrile or isopropyl cyanide), in the presence of a chaotropic compound through binding to a matrix such as glass fiber or silica. Just as unexpected was the fact that this combination also increased the calculated fetal fraction deriving from a SNP based NIPT method, given that contact times between the glass fiber matrix and the DNA binding state were much shorter than under binding conditions established with IPA as a solvent.

Further embodiments described herein relate to a method for binding nucleic acids to a matrix and isolating the nucleic acids, comprising contacting the nucleic acids from a biological sample with a matrix in the presence of a chaotropic compound and a solvent, thereby binding the nucleic acids to the matrix, wherein the solvent comprises an aprotic solvent such as a nitrile compound, tetrahydrofuran, or a combination thereof.

In some embodiments, the nucleic acids are contacted with the matrix in the presence of a nitrile compound selected from ACN, PCN, BCN, IBCN, or a combination thereof. In a particular embodiment, the nitrile compound is ACN. The nucleic acids can be contacted with the matrix in the presence of, for example, about 10% to about 20% of ACN, or about 13% to about 18% of ACN, or about 15% of ACN.

In some embodiments, the nucleic acids are contacted with the matrix in the presence of less than 10% of alcohol, or less than 5% of alcohol, or less than 2% of alcohol, or less than 1% of alcohol, or substantially or totally in the absence of alcohol. In some embodiments, the nucleic acids are contacted with the matrix in the presence of less than 10% of propanol, or less than 5% of propanol, or less than 2% of propanol, or less than 1% of propanol such as isopropanol, or substantially or totally in the absence isopropanol. In some embodiments, the nucleic acids are contacted with the matrix in the presence of less than 10% of non-water protic solvents, or less than 5% of non-water protic solvents, or less than 2% of non-water protic solvents, or less than 1% of non-water protic solvents, or substantially or totally in the absence non-water protic solvents.

In some embodiments, the nucleic acids are contacted with the matrix in the presence of a chaotropic compound selected from GnCl, urea, thiourea, guanidine thiocyanate, NaI, guanidine isothiocyanate, D-/L-arginine, hydrogen perchlorate or perchlorate salt of Li+, Na+, K+, or a combination thereof. In a particular embodiment, the chaotropic compound is GnCl. The nucleic acids can be contacted with the matrix in the presence of, for example, about 3.5 M to about 6 M of GnCl, or about 4 M to about 5 M of GnCl, or about 4.4 M of GnCl.

In some embodiments, the nucleic acids are contacted with the matrix in the presence of a chelating compound selected from EDTA, EGTA, citric acid, TPEN, 2,2'-Bipyridyl, DFOM, tartaric acid, or a combination thereof. In a particular embodiment, the chelating compound is EDTA.

In some embodiments, the nucleic acids are contacted with the matrix in the presence of a detergent selected from Triton X-100, Tween 20, N-lauroyl sarcosine, SDS, dodecyldimethylphosphine oxide, sorbitan monopalmitate, decylhexaglycol, 4-nonylphenyl-polyethylene glycol, or a combination thereof. In a particular embodiment, the detergent is Triton X-100. The nucleic acids can be contacted with the matrix in the presence of, for example, about 3% to about 6% of Triton X-100, or about 4% to about 5% of Triton X-100, or about 4.5% of Triton X-100.

In some embodiments, the nucleic acids comprise maternal nucleic acids or fetal nucleic acids. In some embodiments, the nucleic acids are cell free nucleic acids or circuiting tumor nucleic acids. In some embodiments, the cell free nucleic acids are obtained from a sample of a maternal blood, plasma, or serum. In some embodiments, the cell free nucleic acids comprise, for example, cell free fetal DNA and cell free maternal DNA.

The nucleic acids can be, for example, about 50 to about 1200 base pairs in length, or about 70 to about 500 base pairs in length, or about 100 to about 200 base pairs in length, or about 130 to about 170 base pairs in length. In one embodiment, the nucleic acids comprise DNAs. In another embodiment, the nucleic acids comprise RNAs.

In some embodiments, the matrix comprises siliceous materials, silica gel, glass, glass fiber, zeolite, aluminum oxide, titanium dioxide, zirconium dioxide, kaolin, gelatinous silica, magnetic particles, ceramics, polymeric supporting materials, and or a combination thereof. In a particular embodiment, the matrix comprises glass fiber.

In some embodiments, the method further comprises incubating a biological sample comprising the nucleic acids with a protease such as proteinase K, prior to contacting the nucleic acids with the matrix. The biological sample can be, for example, a sample of a maternal blood, plasma, or serum.

In some embodiments, the method further comprises washing the matrix with at least one washing buffer to remove impurities. In some embodiments, the method further comprises drying the matrix. In some embodiments, the method further comprises eluting the nucleic acids from the matrix with an elution buffer.

In some embodiments, the contacting step binds at least 40%, at least 50%, or at least 60%, or at least 70%, or at least 80%, or at least 90%, of nucleic acids having a length of about 72 bp that are present in the composition to the matrix. In some embodiments, the contacting step binds at least 40%, at least 50%, or at least 60%, or at least 70%, or at least 80%, or at least 90%, of nucleic acids having a length of about 118 bp that are present in the composition to the matrix. In some embodiments, the contacting step binds at least 40%, at least 50%, or at least 60%, or at least 70%, or at least 80%, or at least 90%, of nucleic acids having a length of about 194 bp that are present in the composition to the matrix. In some embodiments, the contacting step binds at least 30%, at least 40%, or at least 50%, or at least 60%, of nucleic acids having a length of about 50 bp that are present in the composition to the matrix.

Additional embodiments of described herein relate to a kit for isolating nucleic acids from a biological sample, comprising a binding buffer, wherein the binding buffer comprises a chaotropic compound and a solvent, wherein the solvent comprises an aprotic solvent such as a nitrile compound, tetrahydrofuran, or a combination thereof.

In some embodiments, the binding buffer comprises a nitrile compound selected from ACN, PCN, BCN, IBCN, or a combination thereof. In a particular embodiment, the binding buffer comprises ACN. The binding buffer can comprise, for example, about 15% to about 35% of ACN, or about 20% to about 30% of ACN, or about 25% of ACN.

In some embodiments, the binding buffer comprises less than 5% of alcohol, or less than 2% of alcohol, or less than 1% of alcohol, or less than 0.1% of alcohol, or comprises no alcohol. In some embodiments, the binding buffer comprises less than 5% of propanol, or less than 2% of propanol, or less than 1% of propanol, or less than 0.1% of propanol, or comprises no propanol such as isopropanol. In some embodiments, the binding buffer comprises less than 5% of non-water protic solvents, or less than 2% of non-water protic solvents, or less than 1% of non-water protic solvents, or less than 0.1% of non-water protic solvents, or comprises no non-water protic solvents. The pH of the binding buffer can be, for example, about 4 to about 10, or about 4 to about 5, or about 5 to about 6, or about 6 to about 7, or about 7 to about 8, or about 8 to about 9, or about 9 to about 10, or about 4 to about 8, or about 4.5 to about 6, or about 4.9 to about 5.1.

In some embodiments, the binding buffer comprises a chaotropic compound selected from GnCl, urea, thiourea, guanidine thiocyanate, NaI, guanidine isothiocyanate, D-/L-arginine, a perchlorate or perchlorate salt of Li+, Na+, K+, or a combination thereof. In a particular embodiment, the binding buffer comprises GnCl. The binding buffer can comprise, for example, about 5 M to about 8 M of GnCl, or about 5.6 M to about 7.2 M of GnCl, or about 6 M of GnCl.

In some embodiments, the binding buffer comprises a chelating compound selected from EDTA, EGTA, citric acid, TPEN, 2,2'-Bipyridyl, DFOM, tartaric acid, or a combination thereof. In a particular embodiment, the binding buffer comprises EDTA.

In some embodiments, the binding buffer comprises a detergent selected from Triton X-100, Tween 20, N-lauroyl sarcosine, SDS, dodecyldimethylphosphine oxide, sorbitan monopalmitate, decylhexaglycol, 4-nonylphenyl-polyethylene glycol, or a combination thereof. In a particular embodiment, the binding buffer comprises Triton X-100. The binding buffer can comprise, for example, about 1% to about 6% of Triton X-100, or about 2% to about 4% of Triton X-100, or about 3% of Triton X-100.

In some embodiments, the kit further comprises a digestion buffer comprising a protease such as proteinase K for digesting a biological sample. In some embodiments, the kit further comprises a washing buffer for washing the matrix to remove impurities. In some embodiments, the kit further comprises an elution buffer for eluting the nucleic acids from the matrix.

The binding buffer described herein can be used in a process for binding nucleic acids to a matrix, wherein the binding buffer is mixed with a biological sample (e.g., blood, plasma, or serum) that has been pre-treated with a digestion buffer comprising a protease such as proteinase K.

WORKING EXAMPLES

Example 1—Solvent System for Isolating cfDNA 1.1—Plasma Separation from Whole Blood For each pair of blood collection tubes (BCT's) label one 15 mL conical tube and one 50 mL conical tube with the corresponding sample ID. Centrifuge BCTs at 2,000 rcf for 20 minutes at 22° C. to separate plasma from cells. Recover plasma from each BCT tube, without disturbing the pelleted cell layer, with a 10 mL serological pipette and transferred to a single 15 mL conical tube and remove remaining cell debris with a second 30 minute clarifying spin at 3,220 rcf at 22° C. Transfer the clarified plasma to 50 mL conical tubes avoiding pelleted material. Record volume and hemolysis grade for each plasma (i.e., yellow=None, pink/orange=Moderate, and red/dark red=Severe). Low volume (<6 mL) and severely hemolyzed plasma samples should not be processed. Begin the extraction process of plasma samples immediately or store frozen at −80° C.

Reagents:

| Formula | Reagent |
| --- | --- |
| Proteolysis Buffer | Triton X100 (Triton) |
| | Guanidine chloride (GnCl) |
| | Tris chloride (Tris-Cl) |
| | Ethlenediaminetetraacetic acid solution (EDTA) |
| Proteinase K | Proteinase K from Tritirachium album |
| Binding Buffer | Guanidine chloride (GnCl) |
| | Ethlenediaminetetraacetic acid solution (EDTA) |
| | Acetonitrile (ACN), Ethanenitrile, Ethyl nitrile, Cyanomethane, Methyl cyanide |
| | Triton X100 (Triton) |
| Wash | Ethanol |
| Buffer 1 | N-Lauroylsarcosine (NLS) |
| | Tris chloride (Tris-Cl) |
| | Ethlenediaminetetraacetic acid solution (EDTA) |
| | Distilled Water |
| Wash | Ethanol |
| Buffer 2 | Tris chloride Buffer Solution (Tris-Cl) |
| | Ethlenediaminetetraacetic acid solution (EDTA) |
| | Distilled Water |
| Elution Buffer | 10 mM Tris, 0.1 mM EDTA (pH 8) |

1.2—Plasma Proteolysis/Establishing Proteinase K Digestion Conditions

Adjust the volume of fresh or thawed frozen plasma samples to 10 mL with 1×PBS and process immediately. Samples may be held at room temperature for up to 1 hour at room temperature or placed at 4° C. for wait times <12 hours. Prepare a 20 mg/mL Proteinase K solution less than 30 minutes prior to use. Reconstitute each 100 mg lyophilized vial of Proteinase K (PK) by adding 5 mL dH$_2$O followed by pipetting up and down at least 5× to completely wet the dried protein pellet. Close each PK vial and invert 10× to thoroughly dissolve the protease pellet and place on ice for at least 5 minutes to ensure complete dissolution. Gently flick or shake contents to the bottom of each vial and for consistency pool multiple vials to homogenize and place immediately on ice.

Initiate plasma proteolysis by adding 400 uL freshly prepared Proteinase K solution to each 10 mL plasma sample, cap and inverted each tube 5× to thoroughly mix. Place tubes back into racks at room temperature and proceed until PK has been added to all samples. Without delay, open caps and add 5 mL of PK Proteinase Buffer to each sample one at a time, quickly recap and mix by vortex at high speed for 5 seconds. Arrange samples in racks and submerge in a 42° C. water bath until the water level reaches at least three quarter height of the digestion mix and incubate for 45 minutes. Once the Proteinase K digestion process is complete, immediately move to the next step—Establishing the Nucleic Acid Binding State.

TABLE 1

Composition and Ranges for Enzymatic Plasma Proteolysis by Proteinase K

| Reagents | Range |
| --- | --- |
| Plasma (Sample) | 61.7-68.2% |
| Tris-Cl | 10-15 mM |
| EDTA | 2.5-10 mM |
| Guanidine chloride | 1.8-2.2 M |
| Triton X100 | 5%-8% |
| Proteinase K | 0.4-0.6 mg/mL |

1.3—Establishing the Nucleic Acid (NA) Binding State

Remove racks from the water and blot dry. If samples are to receive quantification targets, add the requisite amount of spike material to test samples, recap, and mix thoroughly. Uncap tubes and add Binding Buffer to each, recap, invert 10× to mix contents, and place back into the water bath at 42° C. for 10 minutes. This step completes the lysis process and sets up a chemical environment which favors binding of nucleic acids to solid phase glass fiber or silica supports. Remove the plasma lysates from the water bath, blot dry, and cool at room temperature (18-22° C.) for 10 minutes in preparation for Nucleic Acid Capture by Glass Fiber Vacuum Filtration

TABLE 3

Composition and Ranges for the Nucleic Acid Binding State

| Reagents | Range* |
| --- | --- |
| Plasma (Sample)** | 27.5-30.5% |
| Tris-Cl | 1.5-2.2 mM |
| Proteinase K (Inactivated) | — |
| Triton X100 | 4%-5% |
| EDTA | 3-5 mM |
| Guanidine chloride | 4.2-4.5 M |
| Acetonitrile | 13-18% |

*Ranges listed are working ranges expected to give high level recovery of short cfDNA fragments.
**Reagents listed in "italics" are carried over from proteolysis and are not present in Binding Buffer.

1.4—Nucleic Acid Capture by Glass Fiber Vacuum Filtration

Prepare glass fiber spin columns for filtration by labeling and fitting a disposable plastic vacuum connector to the exit port. The connectors prevent spin column contamination from the vacuum manifold. Install spin columns on the vacuum manifold and check that all connections are secure. Plug any unused vacuum ports and connect vacuum lines to the manifold and keep the pressure at zero mBar. Wet each column by carefully pipetting 500 µL of Spin Column Conditioning Solution onto the center of each membrane without directly contacting the membrane with the pipette tip. Engage the vacuum briefly to initiate a slow flow of the conditioning solution through the columns. Once complete, interrupt the vacuum. Attach a 45 mL Column Extender to each column and check to make sure the connections are snug. Initiate NA binding by carefully pouring plasma lysates in the nucleic acid binding state into reservoir extenders and initiate filtration by bringing the vacuum to −600 to −800 mBar. Filtration times may vary from sample to sample, but should complete within 45 minutes, and not typically less than 10 minutes. Wash both columns as described below and elute sequentially with 55 uL elution buffer passed over both columns ($1^{st}$ Pass and $2^{nd}$ Pass), recovering the eluate in a separate tube for each binding matrix.

1.5—Sequential Wash Steps, Residual Wash Removal and Drying

Once filtration of all plasma binding lysates is complete, remove the reservoir extender from each spin column, and add 850 uL of Wash Buffer 1 to each spin column. Release the vacuum, bring the pressure to 0 mBar, and add 825 µL of Wash Buffer 2 and reengage the vacuum to draw wash buffer through column. Turn off the vacuum and allow the pressure to reach 0 mbar and add 825 uL of 100% ethanol resume filtration under a vacuum of −600 mBar. Once filtration is complete, allow columns to dry under vacuum for 1 minute, then deduce the vacuum pressure to 0 mBar and close the lid of each spin column. Take each column off the vacuum manifold, remove the disposable vacuum connectors, and place each into a clean 2.0 mL collection tube. Load into a microcentrifuge and spin at 14,000 rpm for 3 minutes to dry residual EtOH. Preheat Elution Buffer to 56° C. prior to elution. Transfer each spin column to a 1.5 mL pre-labeled LoBind microcentrifuge tube.

1.6—NA Elution from Glass Fiber Spin Columns

Add 50 uL of pre-heated Elution Buffer to the center of each filter without touching the filter membrane with the pipette tip. Close spin column lids and incubate at room temperature (18° C. to 22° C.) for 7-10 minutes. Elute cfDNA by centrifugation at 14,000 rpm for 1 minute. Recovered cfDNA can be taken directly into NGS library preparation or stored at −20° C. for future analysis.

1.7—Comparative Testing

As shown in FIG. 1, when IPA was used as solvent, recovery of short dsDNA increased as the IPA concentration was raised and the GnCl concentration fell due to volume displaced by the added solvent.

Figure 2:
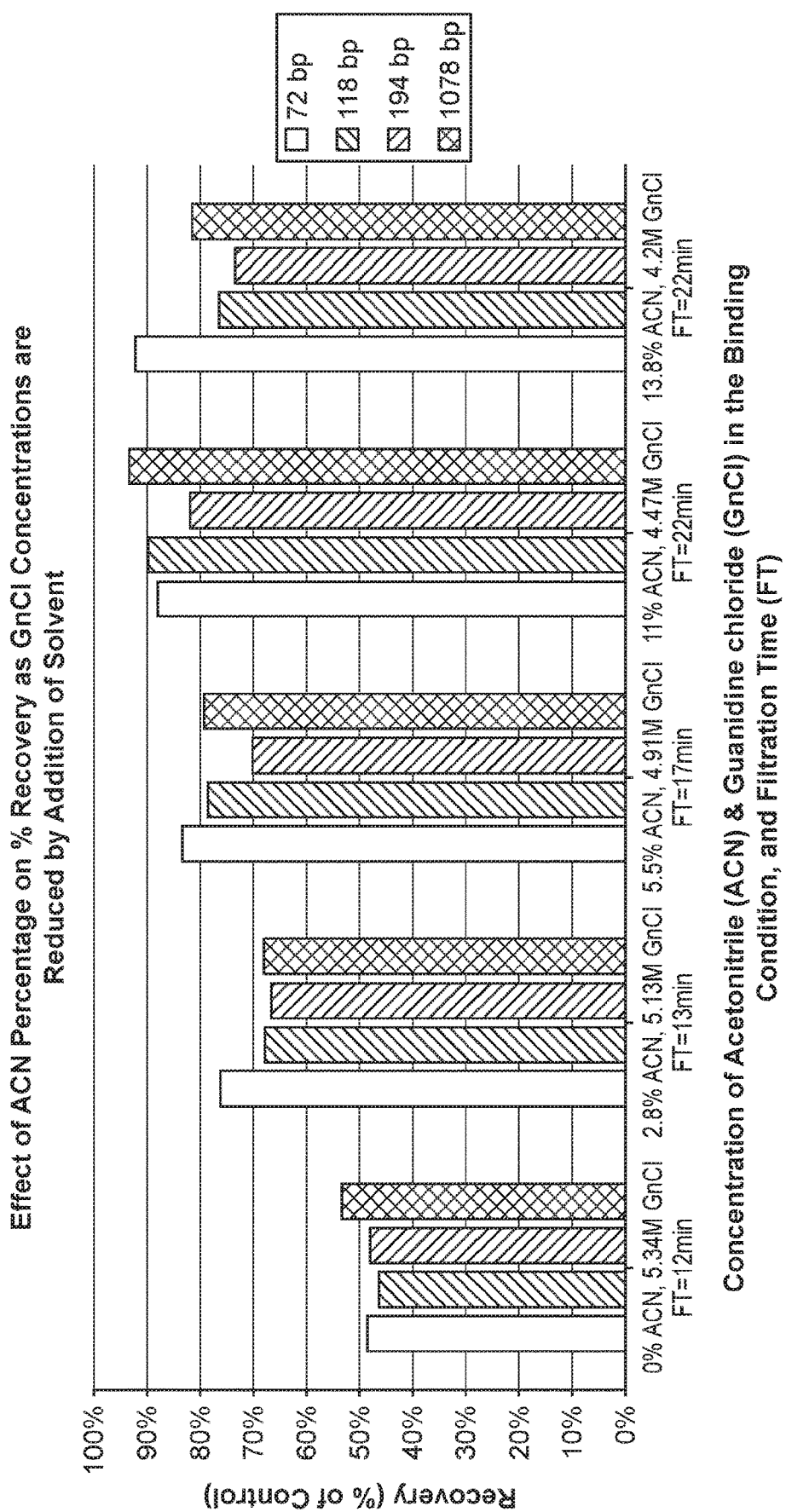
FIG. 2 shows recovery of DNA as a function of the concentration of acetonitrile (ACN) and GnCl in the nucleic acid binding state. Recovery of short dsDNA increases as the ACN concentration is raised and GnCl concentrations fall due to volume displaced by the added solvent. Exogenous DNA targets spiked following proteolysis were quantified by real time PCR quantified using standard curve methods. The percent recovery for each target was determined by comparison against recovery controls assembled by adding the original spike amount to eluates recovered from matched plasma samples isolated with a similar test chemistry. Test samples were normalized with buffer to account for spike volumes added to recovery controls.

As shown in FIG. 2, when ACN was used as solvent, recovery of short dsDNA increased as the ACN concentration was raised and the GnCl concentration fell due to volume displaced by the added solvent.

Figure 3:
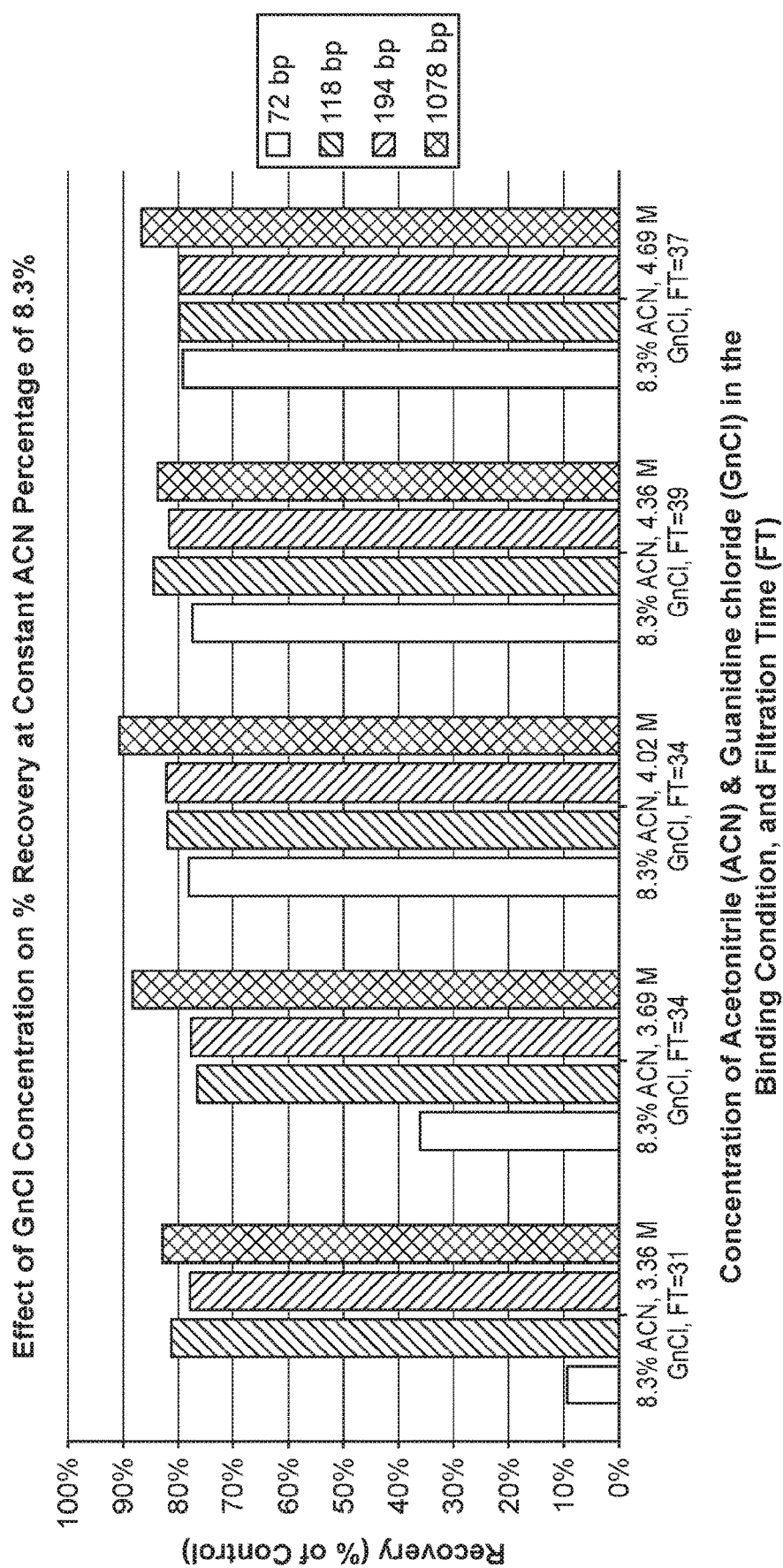
FIG. 3 shows recovery of DNA as a function of GnCl concentration in the nucleic acid binding state when ACN was held constant at 8.3%. Recovery of short dsDNA increased as the concentration of GnCl was increased relative to a constant amount of ACN. Exogenous DNA targets were spiked following proteolysis and quantified by real time PCR and standard curve methods. The percent recovery of each target fragment was calculated by comparing against spike controls in which the original spike amount was added to eluates recovered from matched plasma samples. All test samples were normalized with buffer to account for spike volumes added to recovery controls.

As shown in FIG. 3, recovery of short dsDNA increased as the concentration of GnCl was increased relative to a constant amount of ACN (8.3% ACN in the NA binding state).

Figure 4:
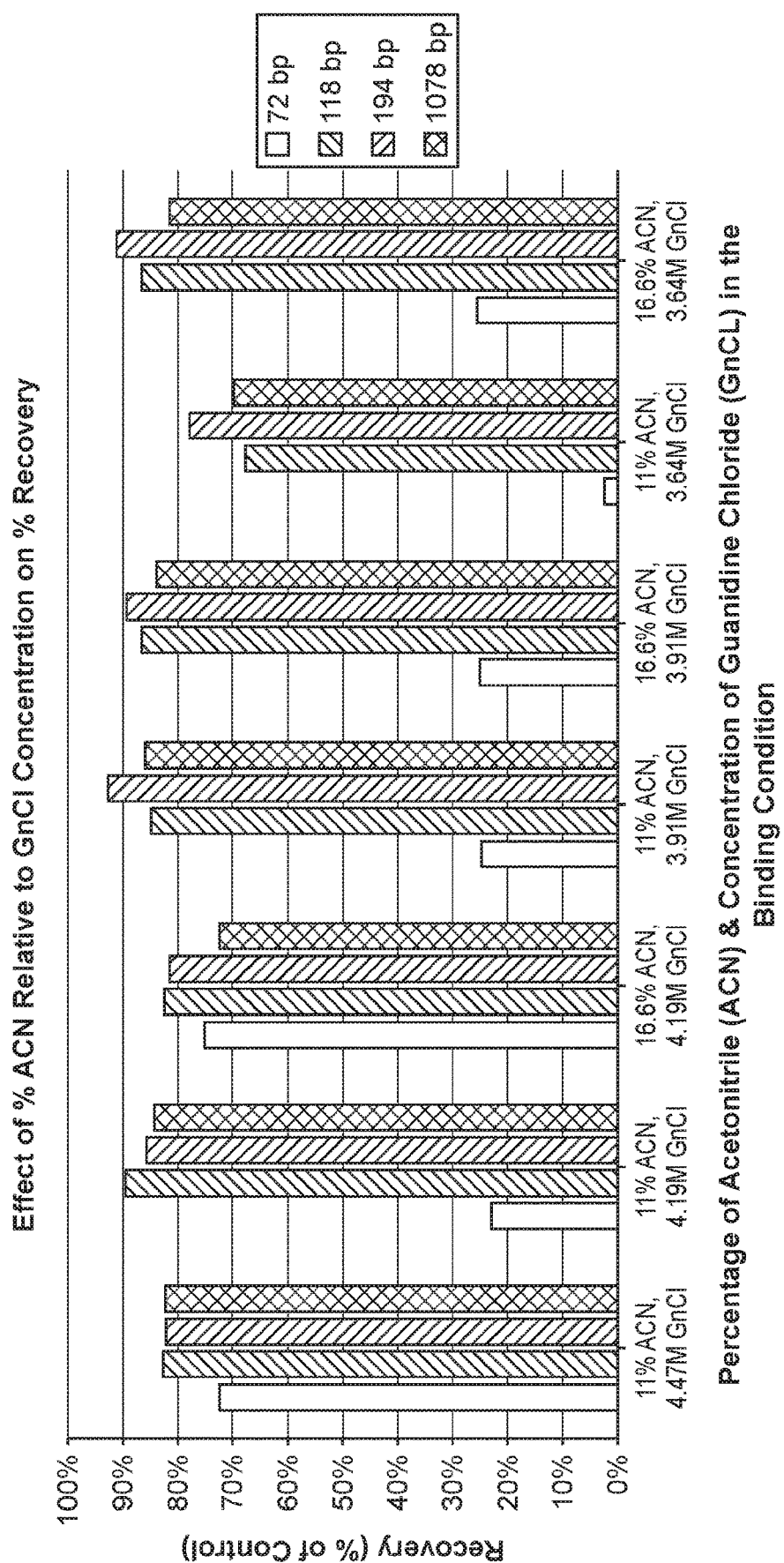
FIG. 4 shows recovery of DNA as a function of the relative amount of ACN and GnCl in the nucleic acid binding state. Recovery of short dsDNA decreased as the concentration of GnCl or percentage of ACN was reduced in the nucleic acid binding state. An increase of either ACN or GnCl compensated for the deficiency of the other. For instance, recovery of the 72 bp fragment improved when ACN was held constant at 11% and GnCl increased from 4.19 M to 4.47 M. This also happened when GnCl was held constant at 4.19 M and ACN increased from 11% to 16.6%. Exogenous DNA targets were spiked following proteolysis and quantified by real time PCR using standard curve methods. Percent recovery for each fragment was determined by comparison to spike controls established by adding the original spike amount to eluted cfDNA isolated from plasma samples by a similar test method. All test samples were normalized with buffer to account for the volume added to recovery controls.

As shown in FIG. 4, recovery of short dsDNA decreased as the concentration of GnCl or percentage of ACN was reduced. An increase of either ACN or GnCl can compensate for the insufficiency of the other. For instance, recovery of the 72 bp and 118 bp fragment improved when ACN was held constant at 11% and GnCl was increased from 4.19 M to 4.47 M, and also when GnCl was held constant at 4.19 M and ACN was increased from 11% to 16.6% in the nucleic acid binding state.

Figure 5:
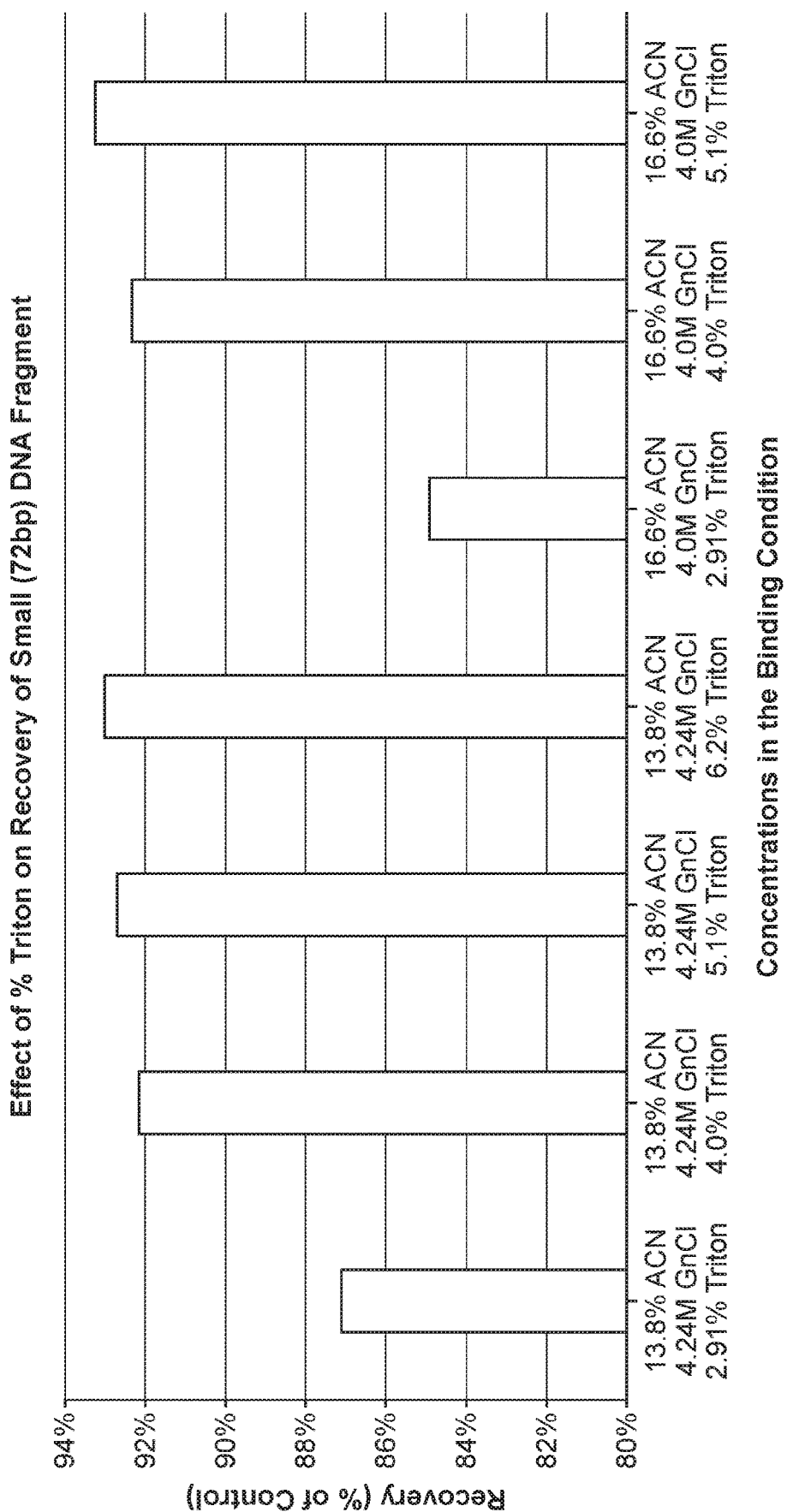
FIG. 5 shows recovery of DNA with increasing amount of Triton X100 in the nucleic acid binding state. Increased concentration of Triton yielded an increase in spike recovery of the 72 bp exogenous DNA target. Targets were quantified by real time PCR using standard curve methods. Percent recovery was determined by comparison against spike controls generated by adding spike targets to eluted cfDNA isolated from plasma samples by a similar test method. All test samples were normalized with buffer to account for the addition of spike material to recovery controls.

As shown in FIG. 5, increased concentration of Triton in the binding condition yielded an increase in spike recovery of the 72 bp exogenous DNA target, under two different test conditions (13.8% ACN and 4.24 M GnCl, or 16.6% ACN and 4 M GnCl).

Figure 6:
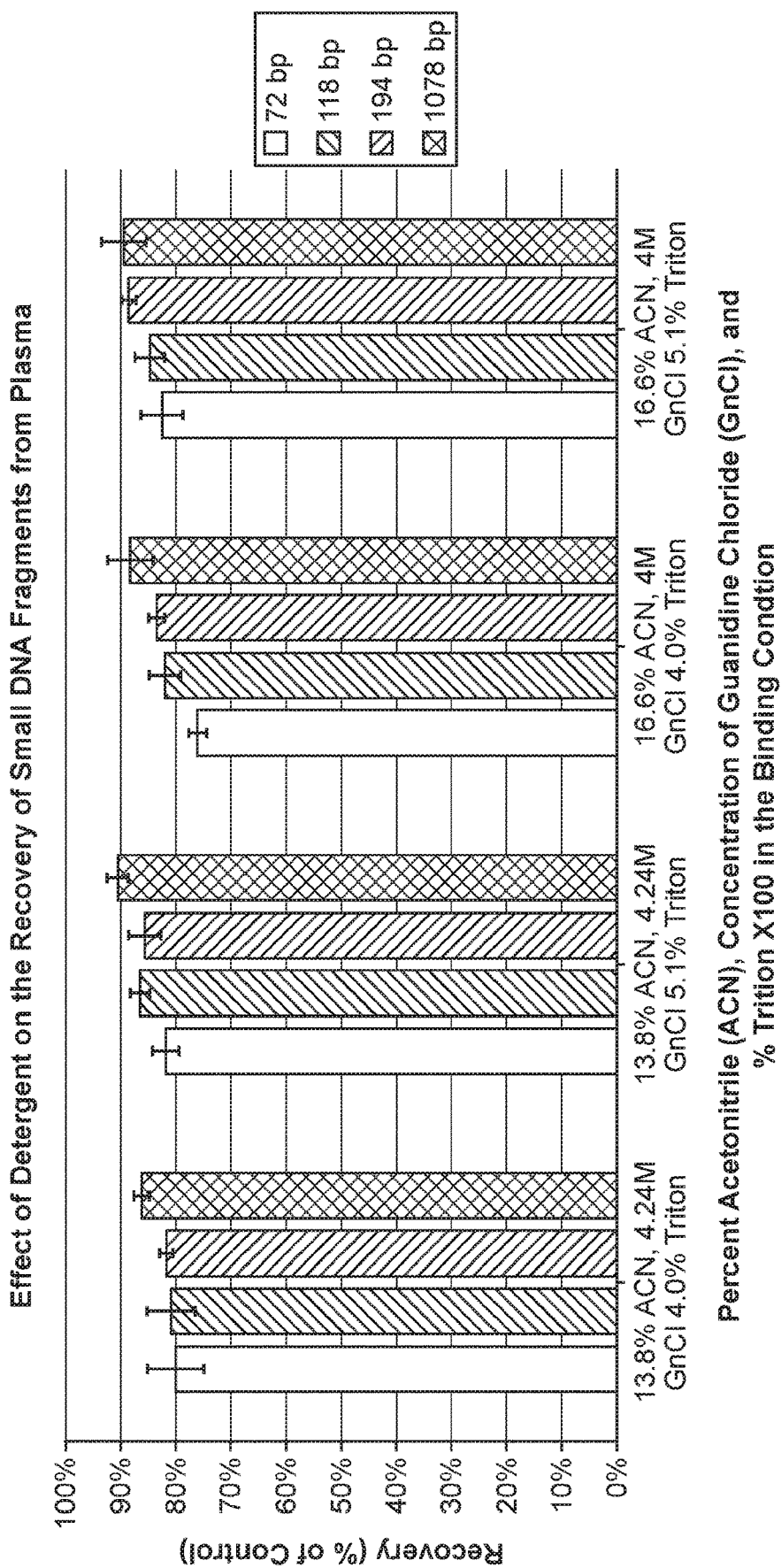
FIG. 6 shows recovery of DNA from 2 extractions from 2 single donor plasma samples (N=4). The amount of Triton X100 in the nucleic acid binding state was varied to reveal an overall increase in spike recovery with increased Triton at two different ACN and GnCl concentrations in the nucleic acid binding state. Exogenous DNA targets spiked following proteolysis were quantified by real time PCR using standard curve methods. Percent recovery for each target fragment was determined by comparison against the original amount of spike target added to recovered plasma cfDNA extracted by a similar test method. All test samples were normalized with buffer to account for the addition of spike material to recovery controls.

As shown in FIG. 6, increased concentration of Triton in the binding condition yielded an increase in recovery of small DNA fragments from 2 single donor plasma samples under two different test conditions (13.8% ACN and 4.24 M GnCl, or 16.6% ACN and 4 M GnC1).

Figure 7:
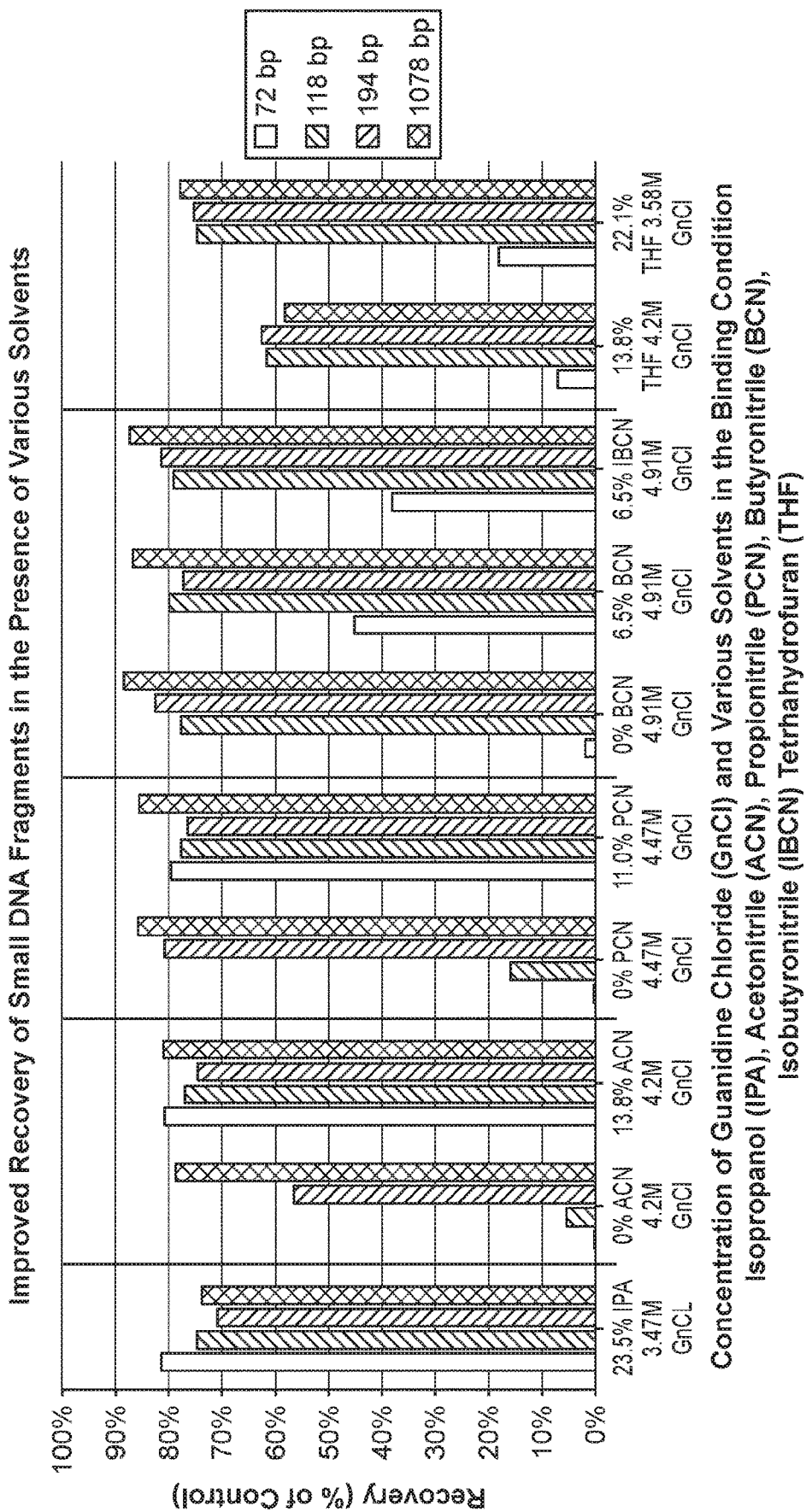
FIG. 7 shows recovery of DNA as a function of organic solvent used to establish the nucleic acid binding state. Various water soluble solvents were added to create the binding condition, and surprisingly it was revealed that solvents whose results are presented (ACN, PCN, BCN, IBCN and THF) all promoted an increase in recovery of the 72 bp and 118 bp fragments compared to the 0% controls (series 2, 4 and 6) in which solvent was replaced by water. Exogenous DNA targets spiked following proteolysis were quantified by real time PCR using standard curve methods. Percent recovery for each target fragment was determined by comparison against the original amount of spike target added to recovered plasma cfDNA extracted by a similar test method. All test samples were normalized with buffer to account for the addition of spike material to recovery controls.

As shown in FIG. 7, various water soluble solvents other than ACN were added to create binding conditions that could promote increased recovery of the 72 bp DNA fragment.

As shown in FIG. 9, fetal fraction estimates for matched pair pregnancy samples were significantly increased when cfDNA was isolated when ACN served as a co-solvent in comparison to IPA in the nucleic acid binding state.

Figure 10:
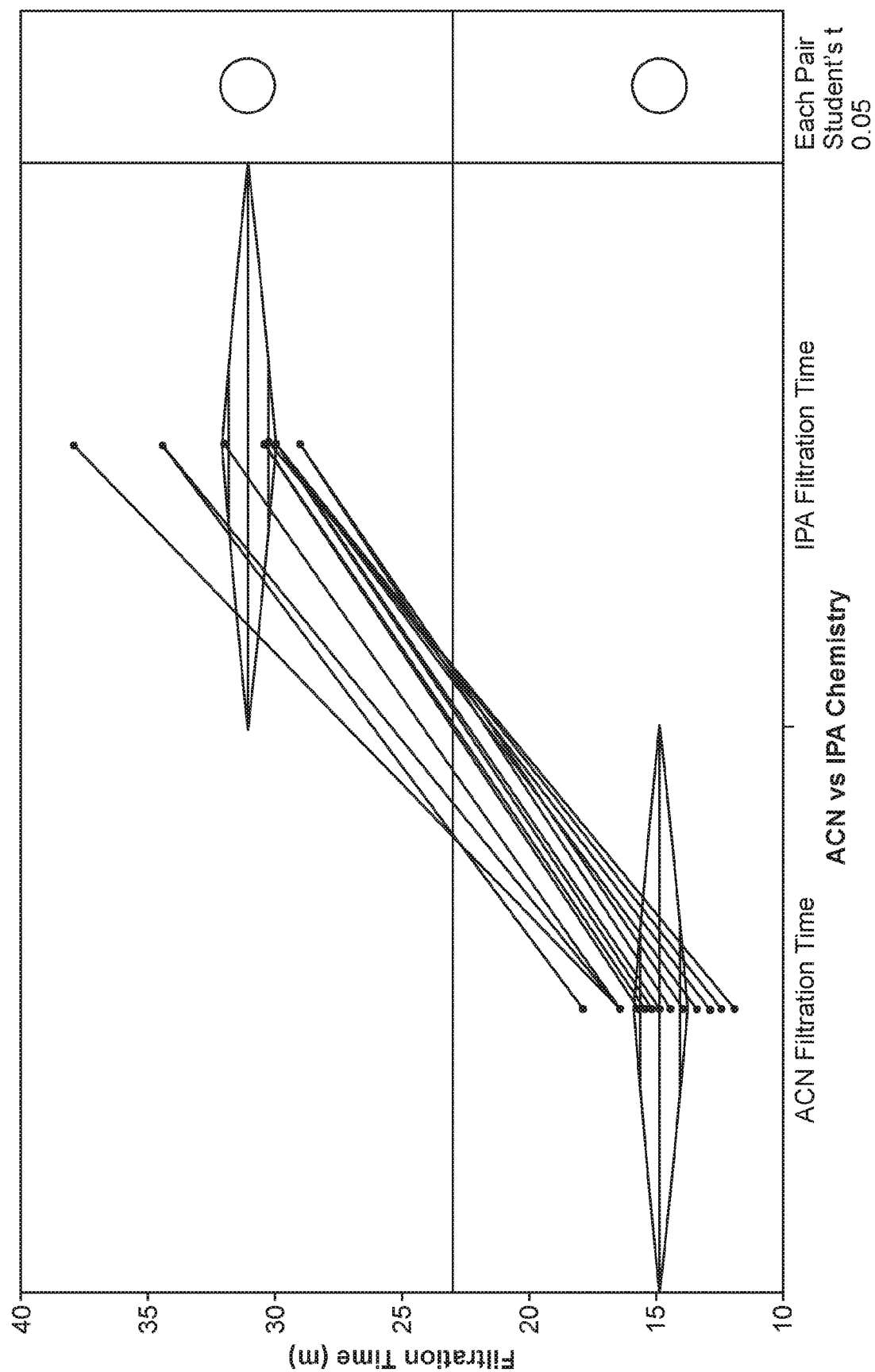
FIG. 10 presents a one-way analysis of variance showing decreased filtration times for plasma cfDNA extractions for which the binding state was established with acetonitrile (ACN) and compared directly to isopropyl alcohol (IPA). The pairwise comparison is of 16 plasma samples from maternal donors isolated by two different optimized methods, one utilizing acetonitrile (ACN) and one isopropyl alcohol (IPA) to establish the nucleic acid binding state (Refer to FIGS. 1 and 2 for a comparison of yield of fragments of various size). Mean filtration times were much shorter when the aprotic solvent ACN was used.
Figure 11:
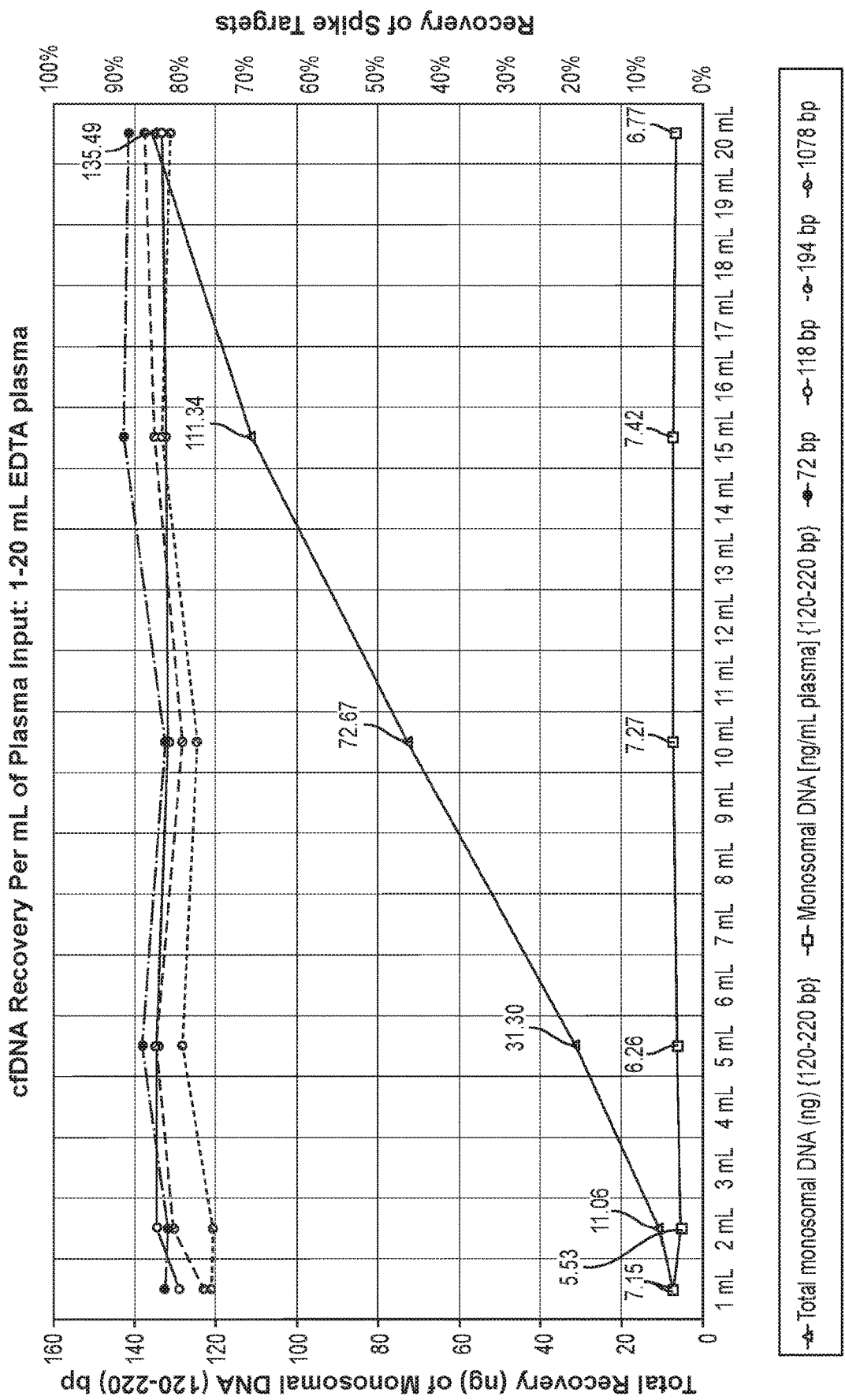
FIG. 11 shows extraction linearity. The plot summarized the total yield of cfDNA and % recovery of the 72, 118, 194 and 1078 bp spike targets from varying input amounts of human plasma. Human plasma; 1, 2, 5, 10, 15 and 20 mL were used as input. The 1 to 5 mL plasma samples were normalized to 10 mL with the addition of 1×PBS and extracted, along with the 10 mL plasma sample, by the standard 10 mL plasma NAS protocol. Reagent volumes were increased proportionally for the 15 and 20 mL plasma samples. 200 pg of spike target mixture was added to each normalized plasma and recovery, as a % of control, was determined by qPCR. Recovery of cfDNA was estimated from Caliper LabChip CE traces by quantifying DNA between 120 and 220 bp (i.e., mono-nucleosome in size). The results show that DNA extraction efficiency is consistent across all plasma volumes. This is shown in the upper portion of the plot by the clustering of recovery data for all four DNA fragment, which returned 80 to 92% of the original spike amount (right axis), for the 72 bp (solid line), 118 bp (dot-dash-dot), 194 bp (dotted line), and 1078 bp (dashed line), respectively. Recovery of monosomal cfDNA scaled linearly with plasma volume input, and correspondingly, the recovery per mL of plasma was constant from 1 to 20 mL of plasma, demonstrating that this method is scalable and efficient across a broad range of input.
Figure 12:
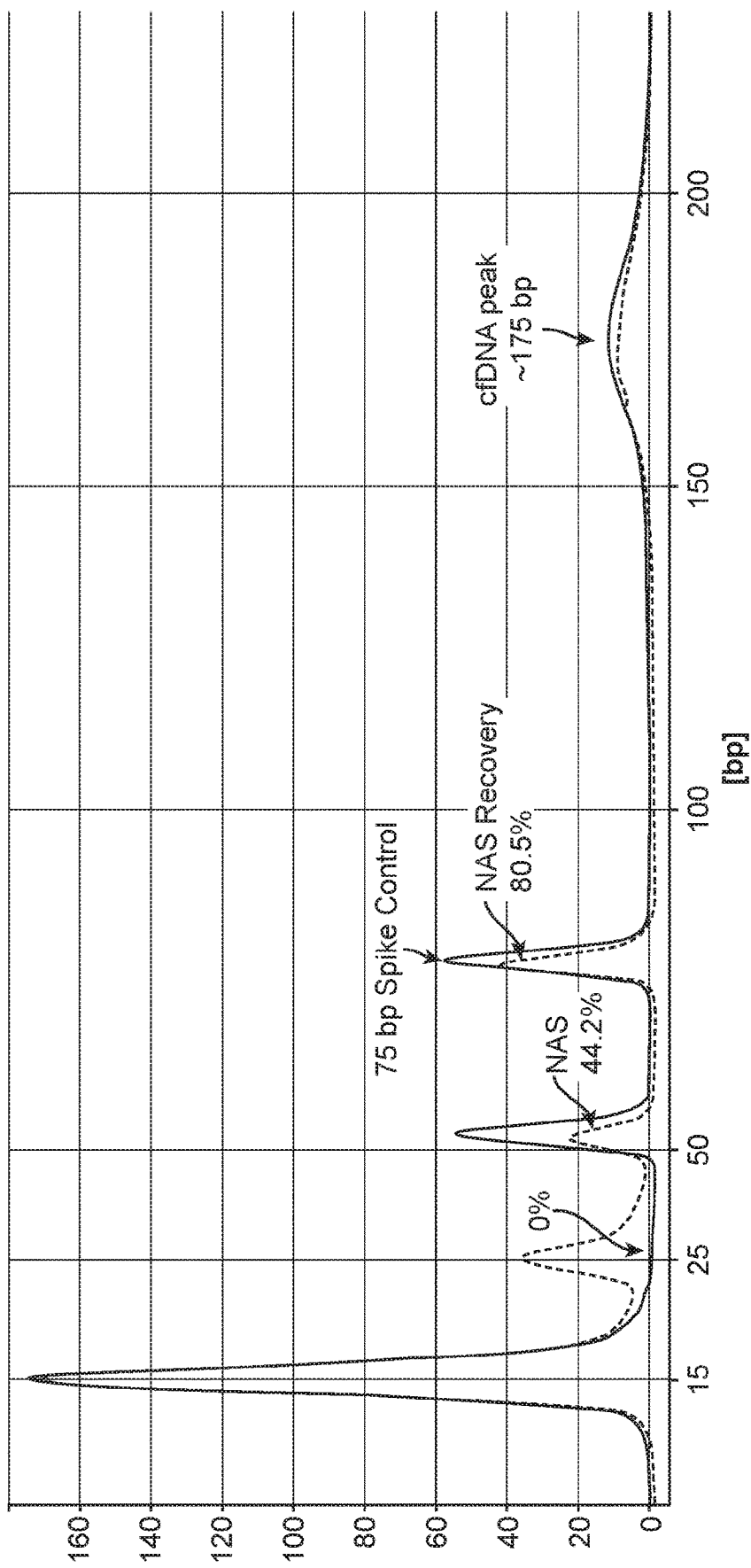
FIG. 12 shows extraction recovery of 25 bp, 50 bp and 75 bp dsDNA fragments from plasma. A mixture of these dsDNA spike fragments was added to a 10 mL Test plasma sample, and buffer only to a matched 10 mL plasma to serve as Control. The NAS extraction method was carried out on both samples. An equivalent amount of spike fragments were added eluted cfDNA from the Control and the same amount of buffer to the Test eluate. 1 uL of each eluate was separated by capillary electrophoresis on an Agilent Bioanalyzer HS chip and the fluorescence plots for each run were overlayed. The plot of the Control run shows three of the tallest peaks at 25, 50 and 75 bp. The plot of lower amplitude shows that 80.5% and 44.2% of the 75 and 50 bp fragments, respectively, were recovered from 10 mL plasma by the NAS extraction method. None of the 25 bp fragment, however, was recovered. This suggests that the NAS chemistry is capable of recovering fragments as small as 50 bp with reasonable efficiency, and fragments of 75 bp in length with good efficiency, in agreement with the qPCR results shown in other figures.

As shown in FIG. 10, filtration times through glass fiber filters were significantly shorter for match paired plasma samples when the nucleic acid binding state was established with ACN as a co-solvent compared to IPA.

Example 2—High-Precision Size Selection & Purification of cfDNA

Figure 14:
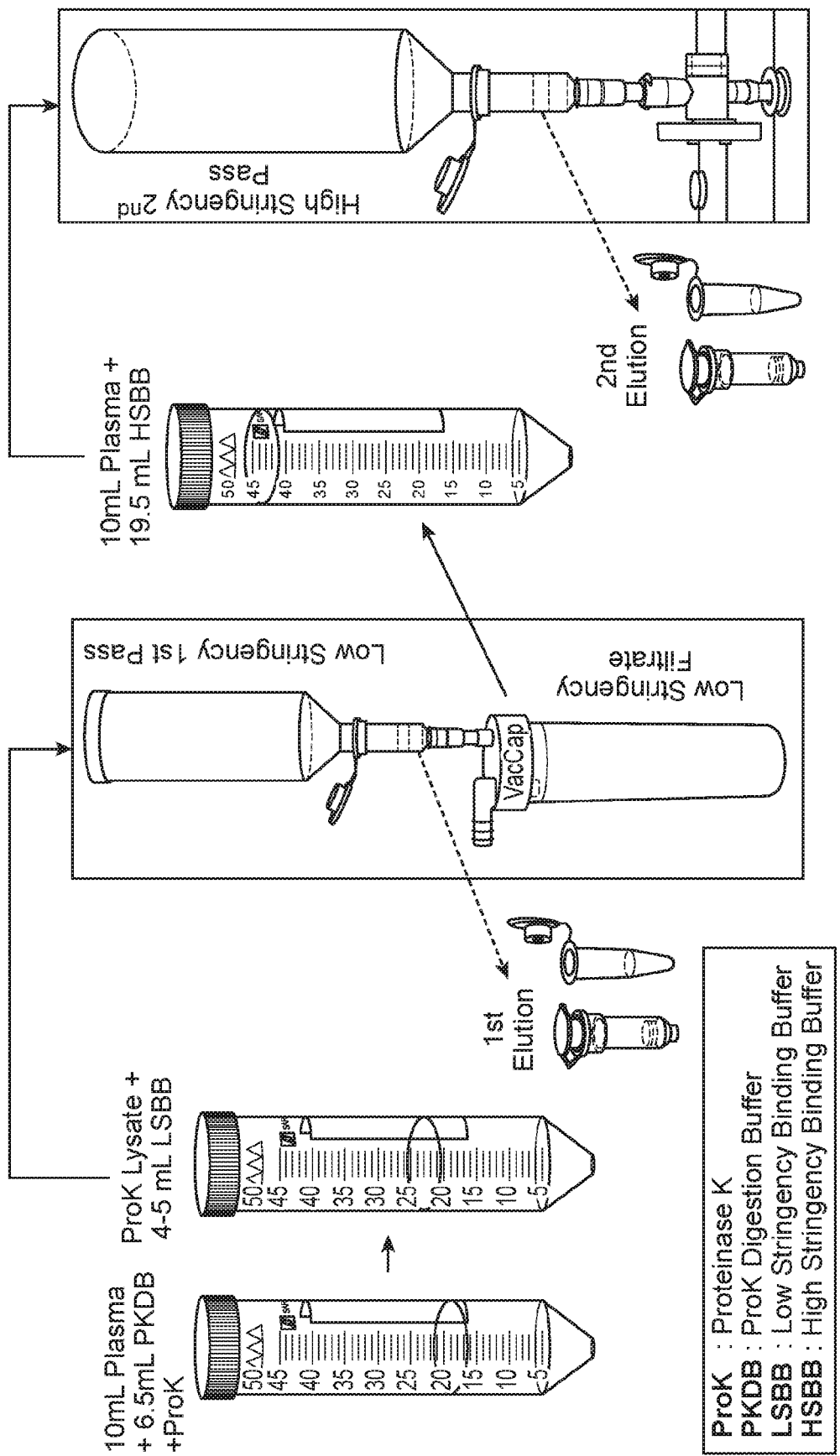
FIG. 14 shows an exemplary workflow of dual filtration size selection using low and high stringency binding buffers (LSBB, HSBB). The method shown is a two-step process wherein the pass though fraction of the $1^{st}$, low stringency, matrix contacting step serves as the input for the $2^{nd}$, high stringency, matrix contacting step. Following washes to remove contaminants, the purified nucleic acids bound to both $1^{st}$ and $2^{nd}$ pass contact matrices can be eluted.

FIG. 14 shows an exemplary workflow of dual filtration size selection using low and high stringency binding buffers (LSBB, HSBB). The lysis portion consists of a 10 mL plasma from whole blood in a 50 mL conical tube, to which 400 µL of 20 mg/mL Proteinase K 6.5 mL of proteinase K digestion buffer (PKDB) was added. The solution was vortexed and incubated at 42° C. for 45 minutes to digest plasma proteins. Once lysis was complete, a low stringency binding buffer (LSBB) was added to the solution, creating the ideal environment for binding of larger DNA fragments to the glass fiber membrane. The LS lysate was cooled to room temperature and passed through an immobilized silica membrane, and the first pass filtrate was collected into a 50 mL conical tube by use of a device known as a VacCap. The first pass flow-through was supplemented with a high stringency binding buffer (HSBB) that established a binding condition for membrane capture of the remaining DNA species. The spent flow-through was treated as waste. Wash and elution steps followed and both captured fraction were eluted and saved.

Figure 20:
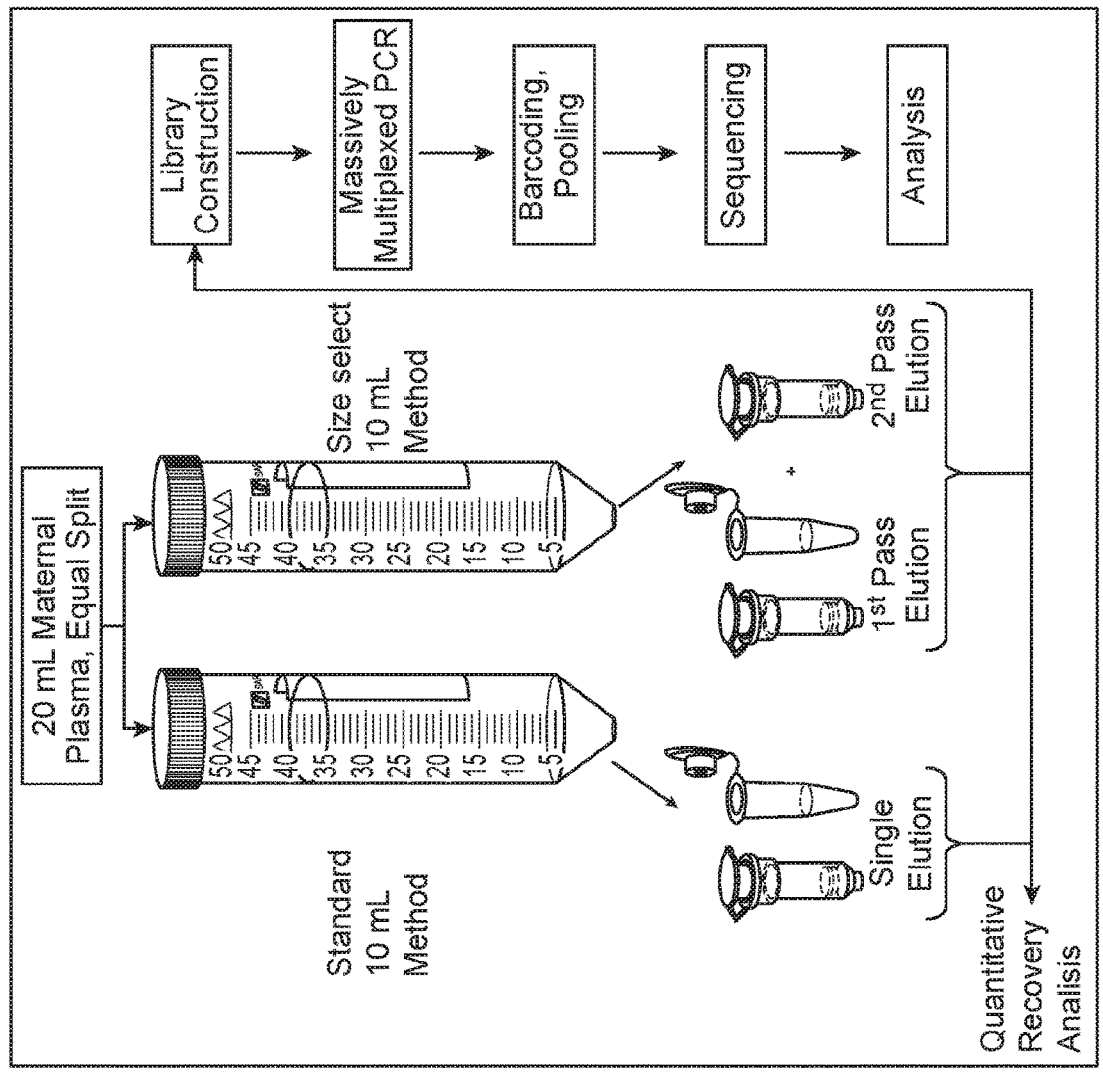
FIG. 20 shows data from an experiment applying the two-step filtration method to preferentially enrich for fetal cfDNA from 12 plasma samples from pregnant mothers. The right panel presents the experimental scheme by which maternal plasma was divided equally and extracted by the standard one pass method in parallel with the two-step method. cfDNA from the one pass, and $1^{st}$ and $2^{nd}$ pass of the 2-step method, served as input for library construction preceding SNP based, next generation sequencing based, prenatal genotypic analysis. Essentially all 1078 bp fragments were captured in the first Pass; nearly all 72 bp fragments were captured in second pass eluate; almost no 194 bp and 1078 bp fragments were captured in second pass eluate; and variable percentage of the 118 bp fragment were captured in second pass eluate. cfDNA is presumed to follow the same pattern of size discrimination.

An proof-of concept experiment was performed as shown in FIG. 20 (right panel) to demonstrate that the sequential two-step capture can be successfully applied for isolation of cfDNA. Two plasma samples of the same origin were utilized. The first was processed with the single-filtration comparative workflow shown in FIG. 13 (i.e., total, single stage DNA capture and elution). The pH of the binding lysate in the comparative workflow was 5.78.

The second plasma sample was treated to the two-step binding protocol shown in FIG. 14 in which the pH of the plasma lysate was adjusted to pH 7.17 prior to first vacuum filtration step. The flow-through was recovered pH adjusted to 5.32 with malic acid and the lysate subjected to a second filtration step. The objective was to reduce the pH to below the control sample (5.78) to ensure capture of the remaining DNA spike targets.

Figure 16:
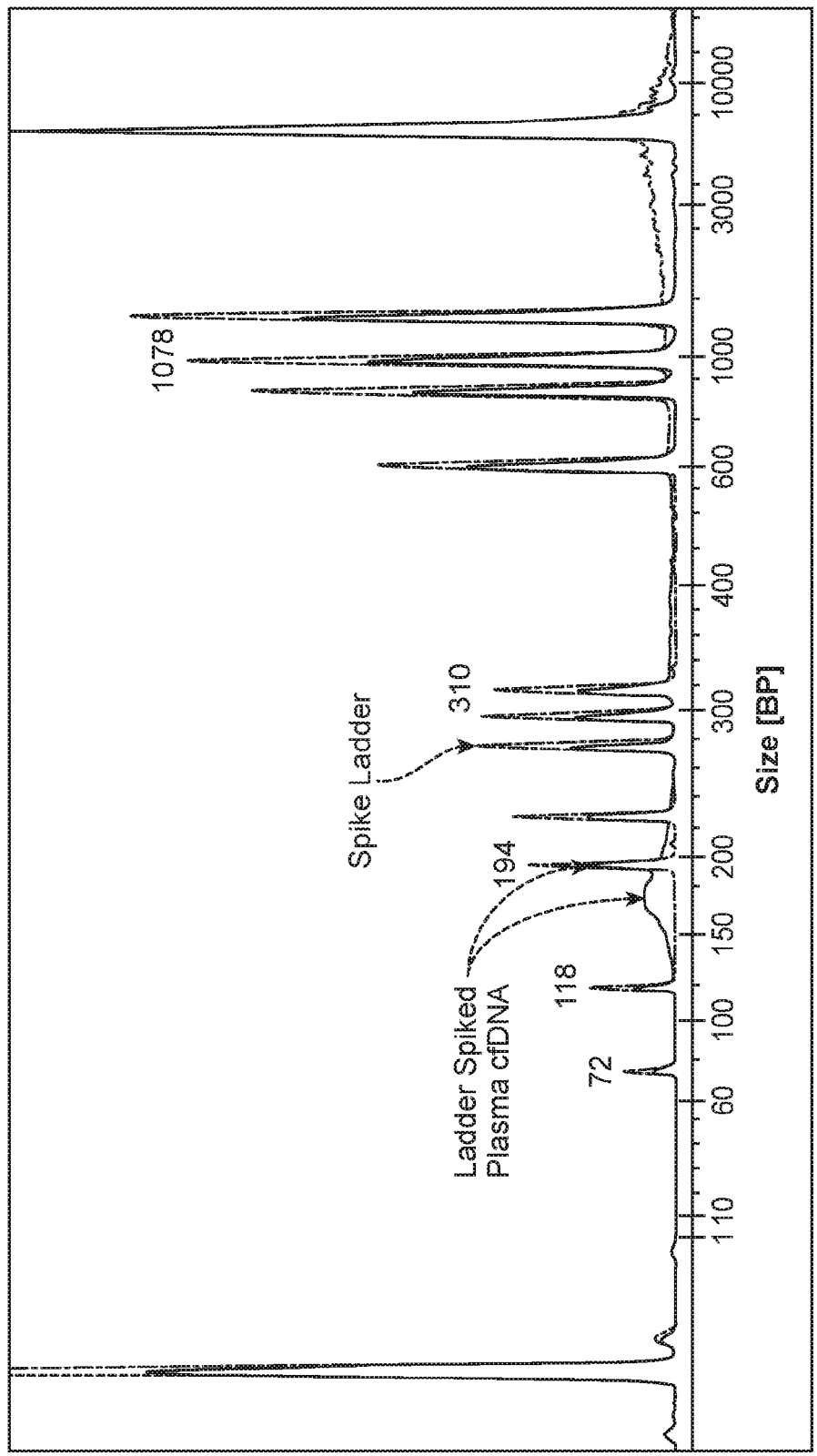
FIG. 16 is an electropherogram showing plasma cfDNA and co-purified defined fragments. The 72 bp, 118 bp, 194 bp, and 1078 bp fragments tracked by qPCR are shown. The main cfDNA peak falls between 118 and 310 bp, 194 bp fragment falls within the leading edge. Fragments from di- and tri-nucleosomes are bigger.

As shown in FIG. 15, DNA fragments were differently captured based on the pH of the lysate prior to immobile phase capture, which proves that the dual filtration method can be applied for partitioning and thus enriching cfDNA fragments directly from plasma during the nucleic acid purification step. The electropherogram of FIG. 16 shows plasma cfDNA and co-purified defined fragments and demonstrates that the major cfDNA peak around 160 bp in size is bracketed by the spike targets that were quantitatively tracked by quantitative polymerase chain reaction (qPCR). All the peaks observed in the electropherogram are ladder fragments that make up the tracked spike fragments.

FIG. 17 shows data from an experiment that tested low stringency binding conditions by uniform titration of components to progressively increase the stringency of the first pass. It was found that incremental increases altered in a predictable way the selective retention of the 118 and 194 bp spike fragments.

Seeing that pH had an effect on size selection, the observations from the experiment of FIG. 15 and the experiment of FIG. 17 were combined to improve the ability to resolved DNA fragments directly from plasma. FIG. 18 shows that by increasing the pH of the low stringency binding condition, in ever increasing GnCl, Triton, and ACN concentration, we can adjust size selection to increase separation between small fragment capture compared to larger DNA fragments.

There are two experiments shown in FIG. 19. The top panel of FIG. 19 demonstrates the difference between low stringency binding without ACN or with ACN. Rows 2 has recorded the first Pass capture and row 3 has recorded the second Pass percent capture results without ACN in Pass 1. Likewise, Rows 4 and 5 show first and second Pass percent capture with ACN added. Higher efficiency of DNA capture was achieved with ACN present in the LS lysate, suggesting benefit for minimizing small fragment capture as evidenced by less 72 bp fragment capture (compare rows 3 and 5).

The second experiment looked into whether a higher pH of the first pass lysate would be even more beneficial. As shown in the bottom panel of FIG. 19, the higher pH condition pH 10 binding buffer did not increase the binding of larger DNA fragments (compare rows 5 and 3, lower table). It was concluded that the lysate pH obtained by adding 4 mL of pH 9 binding buffer was more preferably than that obtained by adding 4 mL of pH 10 binding buffer.

Results from the two-step filtration experiments suggested that it is possible to preferentially enrich for fetal cfDNA directly from maternal plasma, and this was tested on twelve 20 mL plasma samples from pregnant mothers. FIG. 20 shows how, for comparison, each plasma sample was divided into two 10 mL aliquots. One aliquot was treated to the standard one-step purification method outlined in FIG. 13. The matched sample was purified by the two-step method shown in FIG. 14.

Figure 21:
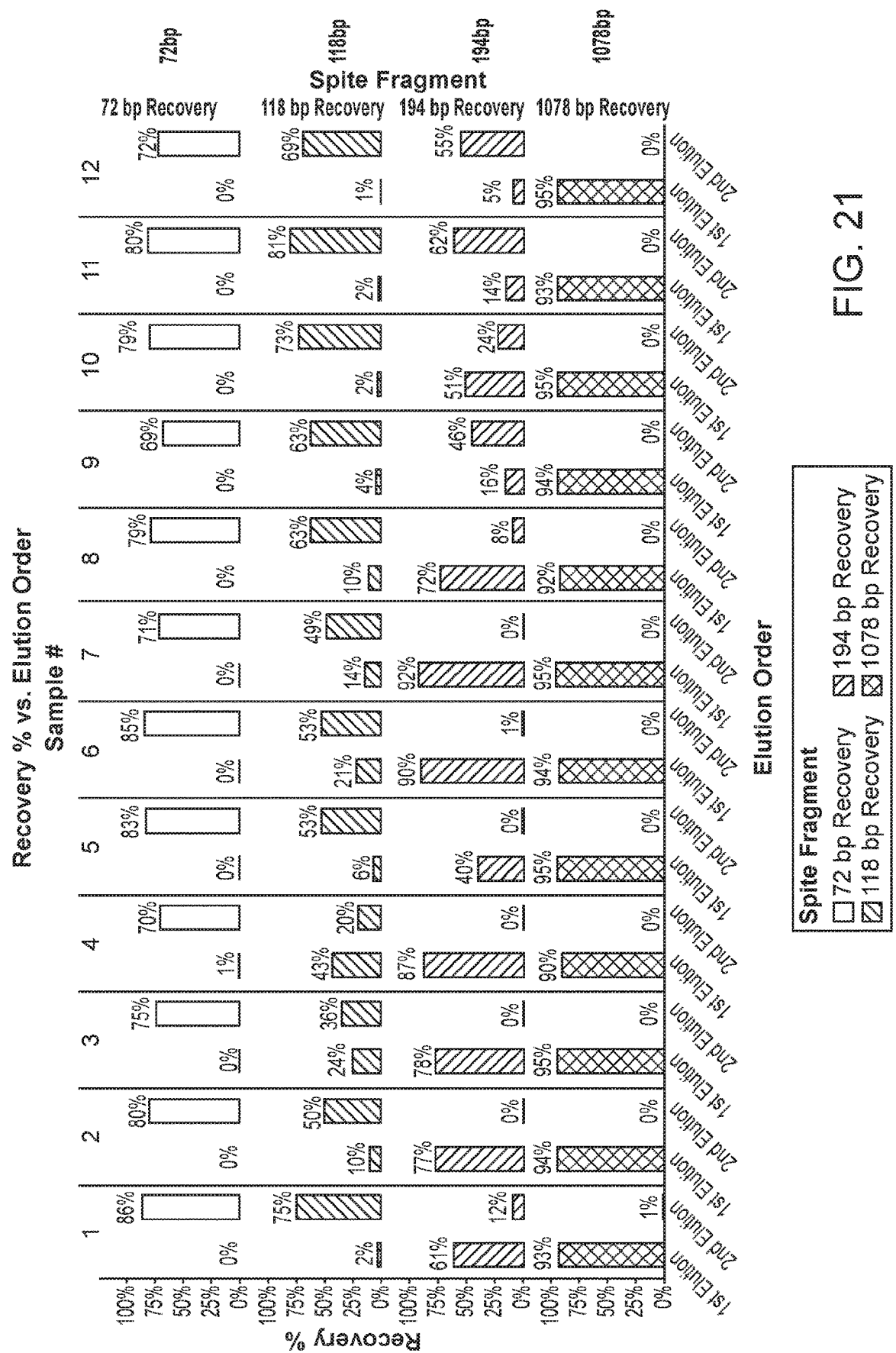
FIG. 21 shows graphically the percentage recovery data of FIG. 20.

FIG. 20 (left panel) shows a heat map of the percentage of spiked fragments captured by the first and second pass filtration step under low and high stringency conditions, respectively. The second pass filter, labeled second Elution is presented in the top half of the table. The size of fragments tracked is listed above the last 8 columns. The Reaction header in column 1 indicate the numbering of the paired sample, pair 1, 2, 3, and so on. This experiment demonstrated the astounding degree to which DNA lost (not captured) in the low stringency first pass, but is subsequently captured entirely by high stringency second pass. This demonstrates that a high degree of discrimination can be achieved between fragments differing by as little as 80 bp, with near complete recovery of all DNA fragments in either the first or second pass elutions. This means a powerful new method for sized selection at purification (SSAP) that is highly efficient and does not result in the loss of any of the original nucleic acids in the starting sample, in this case plasma. The percentage recovery data are summarized graphically in FIG. 21.

FIG. 22 shows results following analysis of isolated cfDNAs, Control vs Test (first pass and second pass). The recovered cfDNA population for each case were processed through Natera's Panorama v3 pipeline. The results demonstrate that the detected child fraction estimate (% CFE) column 8, for all second pass samples were higher than the matched control. Reciprocally, all first pass samples returned lower % CFE than the matched control. This latter result fits with the prediction that omitting smaller cfDNA fragments from a maternal plasma sample would reduce the fraction of child cfDNAs which have been demonstrated to be smaller on average (144 bp vs 160 bp) compared to maternal cfDNA. This method demonstrates the clear ability to achieve a relative increase in fetal fraction in this simple, elegant 2-step capture that ranged from 4% to several folds over control. The CFE data in FIG. 22 are summarized graphically in FIG. 23.

Figure 23:
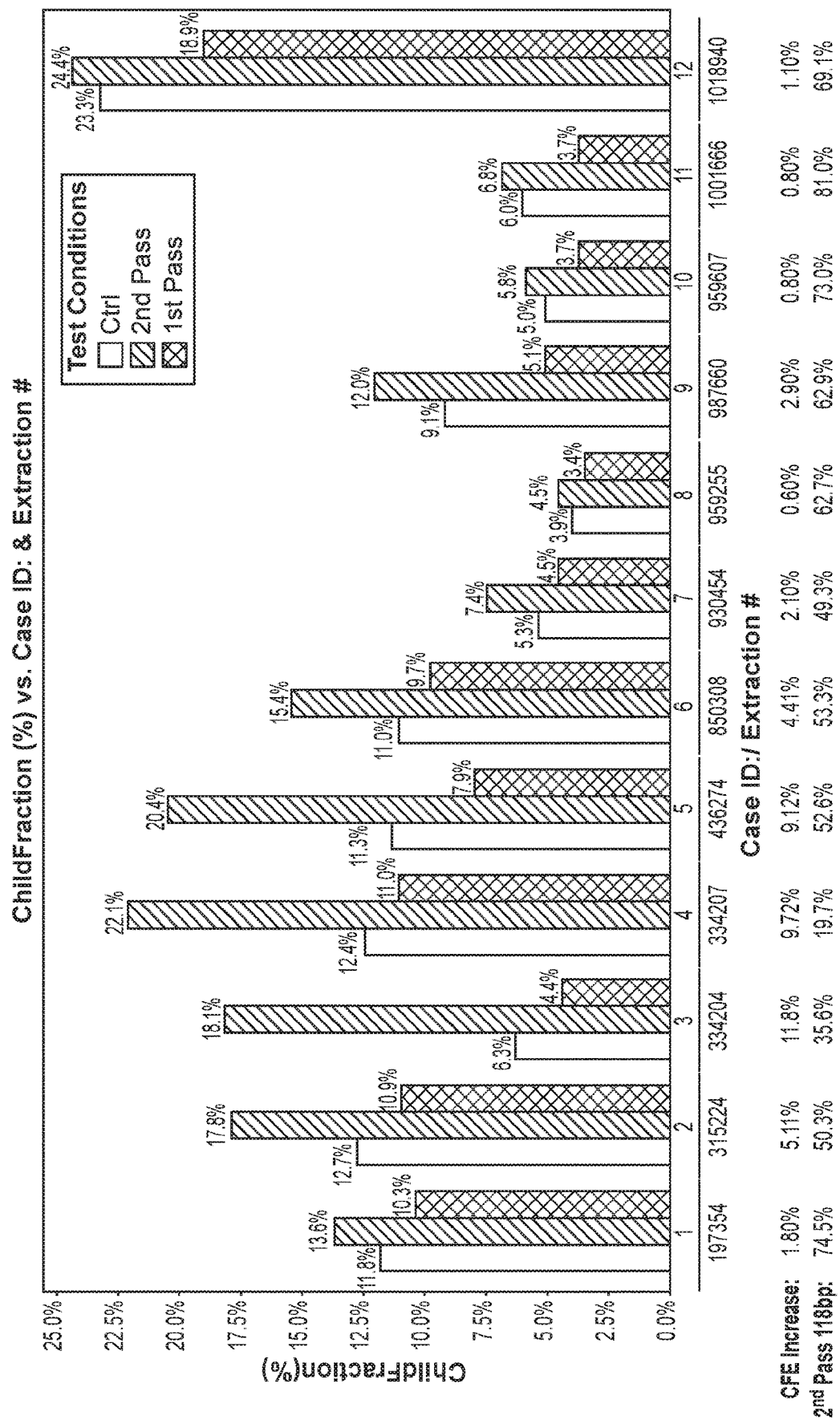
FIG. 23 shows graphically the CFE data of FIG. 22. Nearly all 72 bp fragments are captured in second pass eluate; almost no 194 bp and 1078 bp fragments are captured in second pass eluate; and variable 118 bp fragment are captured in second pass eluate. Absolute % CFE increase ranged between 0.8% to 11.8%, with a mean increase of 4.19% and median increase of 2.51%.

FIG. 23 is a bar graph of the pregnancy plasma samples described in FIG. 22. It demonstrates that for all 12 cases, an increase in CFE was observed in the second pass while a reduction in % CFE was observed in the first pass. This was predicted. In addition, the lower capture of the 118 bp SQA spike fragment can be correlated to increased fetal fraction in the second pass. This fits with the best evidence that suggests fetal cfDNA fragments are smaller than maternal cfDNA.

Figure 24:
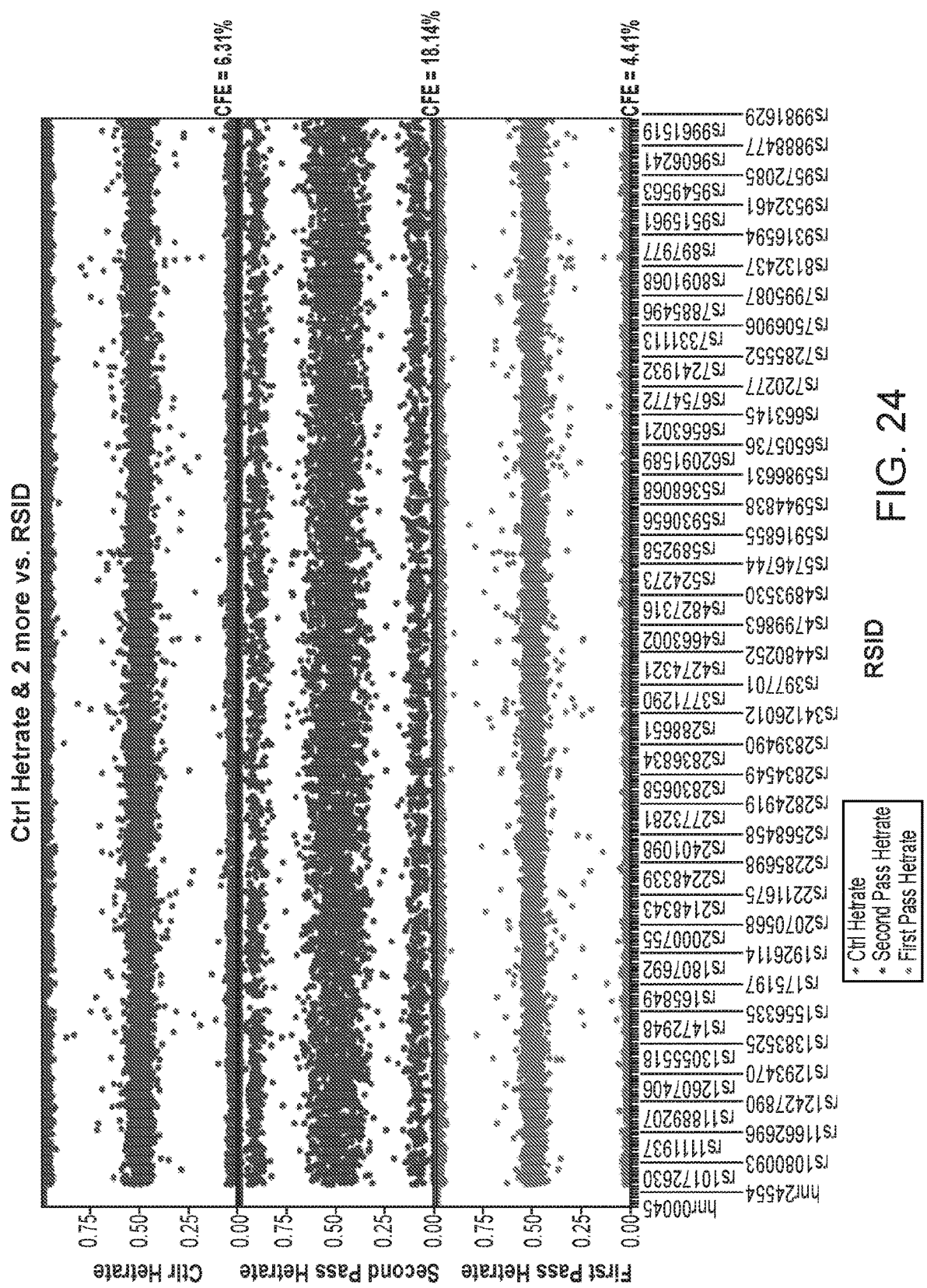
FIG. 24 shows hetrate plots for maternal plasma sample #3, which clearly shows % CFE increase due to second pass selected cfDNA. The child SNPs are seen clearly in the fetal cfDNA enriched plot (middle, $2^{nd}$ pass) compared to the control plot (top, one pass method) and depleted plot (bottom, $1^{st}$ pass).

FIG. 24 shows hetrate plots for maternal plasma sample #3. The Control (top) isolate, and matched Test isolates from second pass (middle) and first pass (bottom) are depicted in the top, middle and bottom panels. There are two key takeaways from these hetrate plots. The first is that hetrate plots can be used to determine fetal fraction. Every dot represents one of the Panorama v3~14K SNPs. The middle plot (second Pass) cfDNA has two extra horizontal bands near the top and bottom axes. These two bands are the fetal cfDNA bands. The higher the child fraction, the closer to the center these two bands are located. These bands are present in the top and (Control) and bottom (first Pass) plots, but because their respective child fractions are much lower, they remain nearer the upper and lower axes compared to the center (second Pass) plot. Second, shifts in the plot demonstrate ploidy type. An extra chromosome causes very apparent shift in hetrate plots. Such shifts were not observed here because this sample represents a normal (euploid) condition. One of the considerations with the dual filtration method is that large child fraction increases can result in fewer molecules of DNA entering the library construction process. This is reflected in Natera's "noise parameter" (FIG. 22, column 9). However, despite the low noise parameter metric, all 13,392 SNPs of Panorama v3 obtained good coverage and the number of reads received per SNP was just as uniform as its control sequencing sample.

FIG. 24 demonstrated that pregnancy plasma #3, which observed the highest increase in child fraction, rising from 6.31% for the control isolation procedure, to 18.14% for the 2-step size selection at purification (SSAP) procedure. Even though this sample would have failed the noise parameter metric, potentially due to input of unique DNA molecules from the mother, a very clean hetrate plot was obtained. It means this second pass sample was not "noisy" as would be expected of samples with such low noise parameter metrics. With apparently much higher fetal derived DNA in this isolate, and the excessive maternal cfDNA and gDNA, making a ploidy type call with this hetrate plot can be accomplished with greater accuracy.

Figure 25:
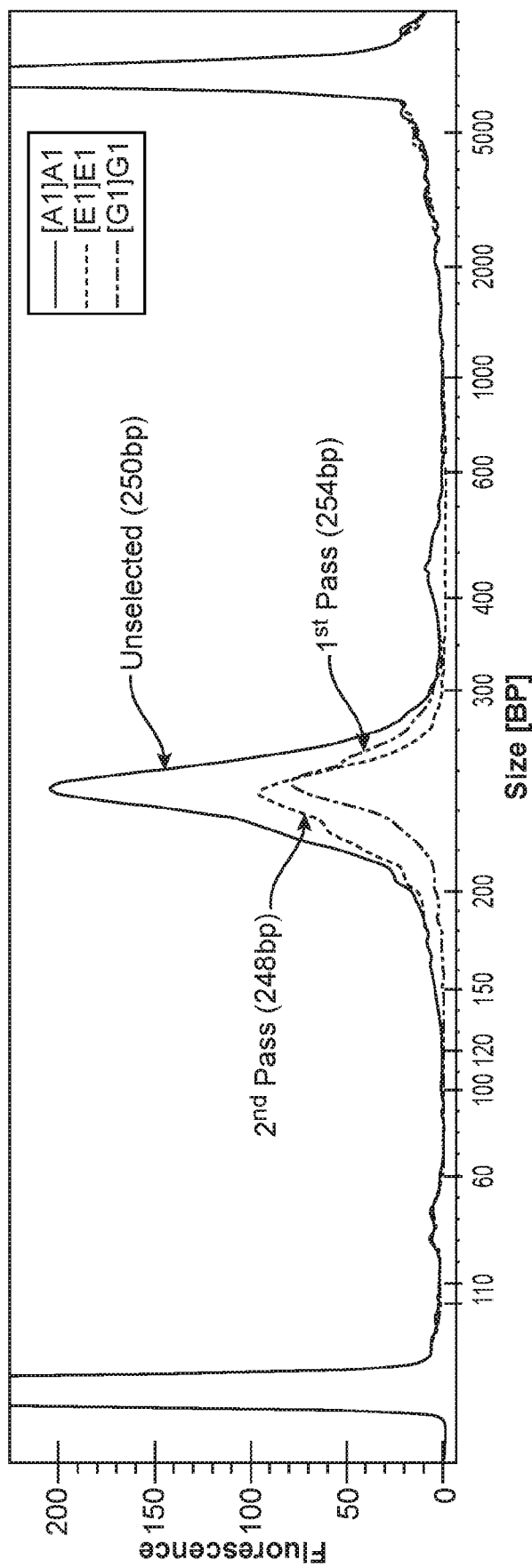
FIG. 25 is an electropherogram overly showing library traces produced from maternal plasma sample #1's control, first pass, and second pass. Library profiles reflect the underlying cfDNA populations in selected fractions. There was a detectable 6 bp of separation between the center peaks of $1^{st}$ and $2^{nd}$ pass libraries and each bracketed the unselected "control" library peak. The shoulders at the leading edge ($2^{nd}$ Pass) and trailing edge ($1^{st}$ pass) show an even greater degree of separation; ~230 bp compared to ~270 bp.

FIG. 25 is an electropherogram of the library produced from sample #1's control, second pass, and first pass samples overlapped. These libraries, due to the addition of ligated amplification sites, are larger in fragment sizes than cfDNA. However, it was demonstrated that by selecting for different sizes of DNA, different peaks can be observed per sample. The second pass sample, which selected for smaller DNA, produced smaller libraries with additional shoulder peaks around ~220 to 240 bp. Meanwhile, the first pass sample, which emphasized capture of larger cfDNA, produced larger libraries with additional larger shoulder peaks around ~270 bp. The child fractions of 11.82% for control, 13.63% for second pass, and 10.32% for first pass, supporting that the selection of differently sized cfDNA can attribute to differences in fetal fraction.

Example 3—No Salt Increase—Size Exclusion Methods

This example demonstrated the size selection process, wherein differential binding is achieved by altering the chemical environment of the plasma lysate (the mobile phase) prior to contacting a binding substrate (the immobile phase) such as glass fiber filters, silica membranes, or silica beads.

The foregoing examples 1 and 2 demonstrated the principle of simultaneous purification size selection in which, coincident with purification, double stranded cell-free DNA (ds-cfDNA) fragments are isolated directly from crude plasma lysates and partitioned into distinct fractions containing subpopulation that differ in their average size (length in base pairs (bp)). As demonstrated in preceding examples 1 and 2, the size cutoff, defined as the approximate length (bp) above which the affinity of double stranded dNA (dsDNA) for the immobile phase is high enough for binding to occur, can be varied substantially. Without being bound by theory, it is an hypothesis herein that there are a multitude of physical-chemical properties that affect the relative affinity of double stranded DNA for glass fiber filters (borosilicate glass) or silica membranes, and no single binding theory can describe the myriad interactions that balance the binding equilibriums that dictate length dependent binding of dsDNA fragments.

Herein, a SSAP system was developed by empirically determining which components in the low stringency and high stringency binding buffers used had the greatest influence over length dependent binding of dsDNA fragments to glass fiber filters. Among the most notable effectors of the binding response were pH, chaotropic salt concentration, solvent polarity, and detergent type and concentration. Response profiling indicated that pH, solvent type and solvent concentration were the most controllable effectors of length dependent glass filter binding of dsDNA in a plasma lysate background. It was found that controlling the size cutoff in the low stringency binding conditions was the most important factor for size selection as it determined the extent to which fragments of a certain size are included or excluded from a given fraction. It was also found that solvent and pH brought about both gradual and broad ranging binding responses, and by modulating either or both components, the cutoff size could be increased or decreased to some degree, and the sharpness of the cutoff could also be controlled.

These observations gave rise to a new process in which pH and solvent were adjusted to achieve variable low stringency and high stringency binding conditions that favored or disfavored the binding of dsDNA fragments above or below a certain length (bp). This was accomplished while keeping the concentration of chaotropic salts in the low and high stringency binding conditions constant, and thus, the disclosure herein established a variation of the SSAP system that is referenced in the following as No Salt Increase—Size Selection At Purification or NSI-SSAP (FIGS. 26-30) when applied to plasma samples, and No Salt Increase—Library Size Selection or NSI-LSS (FIGS. 31-36) when applied to cfDNA preserved as adapter ligated libraries.

Methods and Materials

Figure 26:
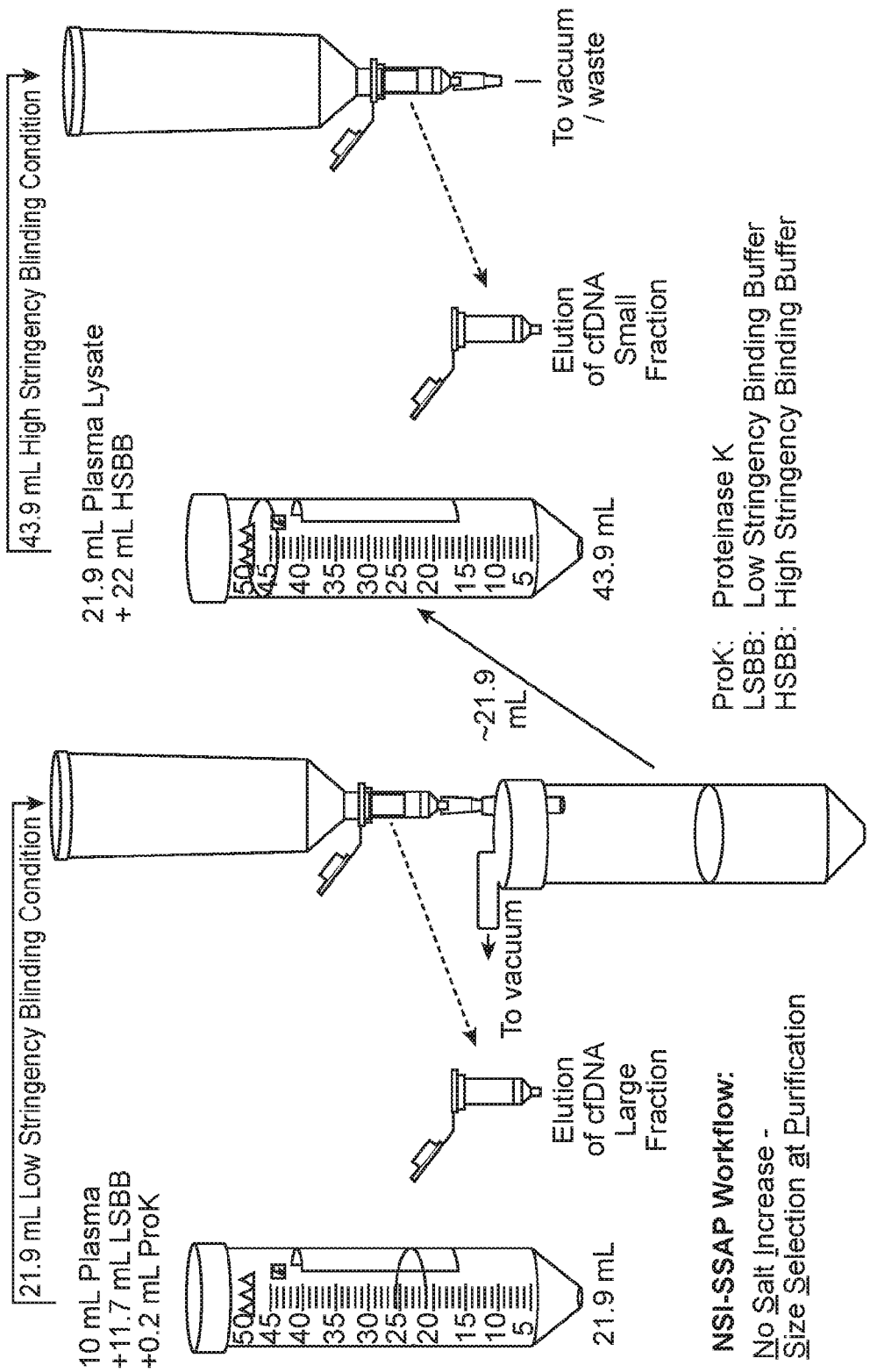
FIG. 26 shows graphically the No Salt Increase-Size Selection At Purification (NSI-SSAP) workflow employing dual filtration size selection under low and high stringency binding conditions in which salt concentration was not increased. The concentration of chaotropic salt in the low stringency binding condition begins at >30% and remains unchanged, or decreases slightly, when the subsequent high stringency binding condition is formed. To begin, an initial lysis portion is established by combining 10 mL plasma from whole blood with 200 µL of 20 mg/mL Proteinase K and 11.7 mL of low stringency binding buffer (LSBB) in a 50 mL conical tube. The mixture is incubated at 42° C. for 45 minutes to digest plasma proteins and the lysate is cooled to ambient temperature (15-25° C.) and filtered through a glass fiber or silica membrane. The filtrate is collected with a device like the one shown and saved. The first pass filtrate is mixed with 22 mL high stringency binding buffer (HSBB) to establish the high stringency binding condition, and filtered again through a glass fiber or silica membrane to capture the remaining DNA fragments. Each filter is washed and eluted to recover the $1^{st}$ Pass, Large cfDNA Fraction and $2^{nd}$ Pass, Small cfDNA Fraction. The twice filtered lysate is disposed of in waste.

An example of the NSI-SSAP workflow employing dual-filtration size selection under low and high stringency binding conditions in which salt concentration was not increased is illustrated in FIG. 26. The concentration of chaotropic salt in the low stringency binding condition begun at >30% and remained unchanged, or decreased slightly, when the subsequent high stringency binding condition was formed. To begin, an initial lysis portion was established by combining 10 mL plasma from whole blood with 200 µL of 20 mg/mL Proteinase K and 11.7 mL of low stringency binding buffer (LSBB) in a 50 mL conical tube. The mixture was incubated at 42° C. for 45 minutes to digest plasma proteins and the lysate was cooled to ambient temperature (15-25° C.) and filtered through a glass fiber or silica membrane. The filtrate was collected with a device like the one shown and saved. The first pass filtrate was mixed with 22 mL high stringency binding buffer (HSBB) to establish the high stringency binding condition, and filtered again through a glass fiber filter or silica membrane to capture the remaining DNA fragments. Each filter was washed and eluted to recover the 1st Pass, Large cfDNA Fraction and 2nd Pass, Small cfDNA Fraction. The filtrate from the $2^{nd}$ column may be either be discarded or saved for further processing.

For the NSI-SSAP method, the low stringency binding buffer (LSBB) composition may comprise between about 0 to about 20% Acetonitrile, about 0 to about 15% Tween 20, about 6 to about 7.8 molar Guanidine chloride, about 10 to about 50 millimolar Tris(hydroxymethyl) aminomethane (Tris, free base), about 0 to about 2 mM Ethylenediaminetetracetic acid (EDTA, free acid), and have a pH of about 7.0 to about 10. Correspondingly, the high stringency binding buffer (HSBB) composition may comprise between about 10 to about 40% Acetonitrile, about 0 to about 10% Tween 20, about 0 to about 2% Ethanol, about 3.2-about 3.6 molar Guanidine chloride, about 10 to about 70 millimolar 2-(N-morpholino)ethanesulfonic acid (MES, free acid), about 0 to about 2 mM Ethylenediaminetetracetic acid (EDTA, free acid), and have a pH of about 4.05 to about 6.5.

In the NSI-SSAP method, the low stringency binding condition also establishes conditions for protease digestion and is prepared by combining 10 mL plasma, serum, urine, or other cell free biological fluid, with about 50 to about 300 uL proteinase K (20 mg/mL) and about 11.7 to about 15.7 mL low stringency binding buffer (LSBB). In one preferred embodiment the final concentrations are listed in FIG. 27 (upper table), and concentrations of various components can range accordingly: plasma (about 38.9% to about 45.66%), Acetonitrile (about 0% to about 12.1%), Tris base (about 5.43 mM to about 20 mM), Guanidine chloride (about 3.2055 M to about 4.76 M), Tween 20 (about 0% to about 9%), EDTA (about 0% to about 1.2%) and a pH of about 7 to about 9. Following an incubation time of 30 minutes to 2 hours at temperature between 20° C. and 45° C., the lysate was filtered through a glass fiber filter or silica membrane and the filtrate collected and saved to purify the remainder of cfDNA. During the filtration step a variable amount cfDNA fragments will bind to the filter membrane depending on the length (bp) of the dsDNA fragment. The saved filtrate from the $1^{st}$ filtration is then mixed with additional reagents to convert it to a higher stringency binding condition. In the examples given, the high stringency binding condition is formed by mixing the saved ~21.9 to ~25.9 mL of filtrate with ~22 to ~26 mL of HSBB. In one preferred embodiment, final concentrations in the high stringency case have been listed (FIG. 27, lower table), and concentrations of key components may vary: plasma (about 19.27% to about 22.78%), Acetonitrile (about 4.59% to about 26.09%), Guanidine chloride (about 3.2055 M to about 4.76 M) with concentrations holding constant at low and high stringency, Tween 20 (about 0 to about 9.55%), Tris-base (about 1.22 mM to about 5.33 mM), MES (about 4.59 mM to about 38 mM), Ethanol (about 0 to about 1%), EDTA (about 0 to about 0.61 mM), and a pH of about 4.05 to about 5.5. This lysate was filtered through a glass fiber or silica membrane to capture the cfDNA therein. The NSI-SSAP method did not lead to the loss of any cfDNA from the sample during purification, but instead partitions all recoverable cfDNA into either the large or small cfDNA fractions, eluted from the $1^{st}$ or $2^{nd}$ glass fiber membranes following standard wash, dry and elution steps.

Figure 30:
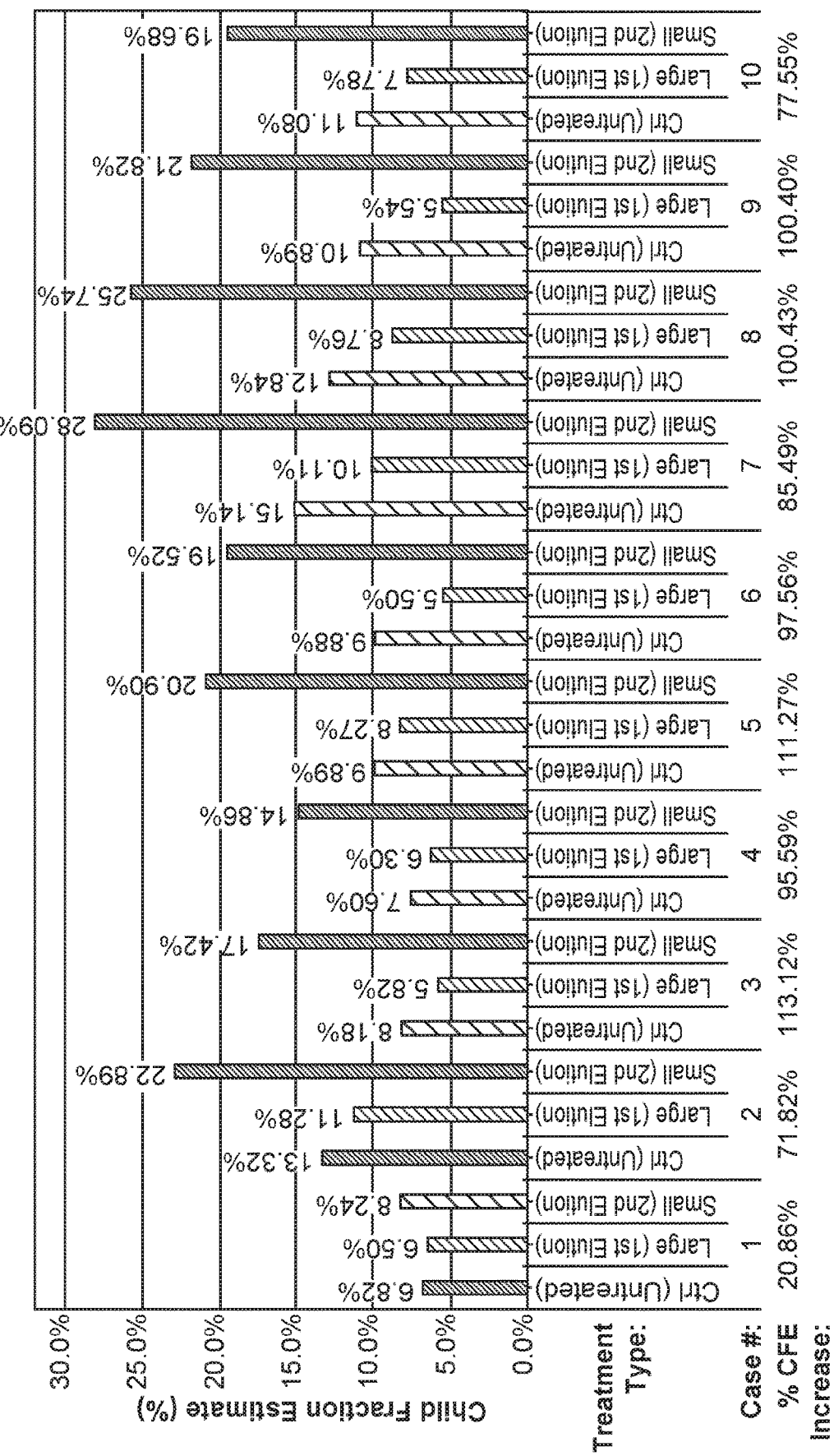
FIG. 30 graphically depicts the SSAP method as applied to 10 pregnancy plasma samples (the same as samples analyzed in FIG. 29) to obtain child fraction estimates (CFE) for each. The plots compare cfDNA fraction separated by Ctrl (Control) with no size selection, reflecting the total cfDNA fraction, $1^{st}$ Elution (large cfDNA fraction), and $2^{nd}$ Elution (small cfDNA fraction), for each case. Two ×10 mL plasma samples were extracted for each case. cfDNA from one 10 mL sample was processed to obtain all cfDNAs in one fraction (total cfDNA), while the second 10 mL sample was performed using the SSAP method to generate cfDNA from the $1^{st}$ and $2^{nd}$ filter pass. For every case, the $1^{st}$ pass larger cfDNA fraction, enriched in maternal DNA, generated a lower CFE compared to the Ctrl. The $2^{nd}$ pass small cfDNA fraction was enriched for fetal cfDNA fragments resulting in an increase in CFE compared to control.
Figure 31:
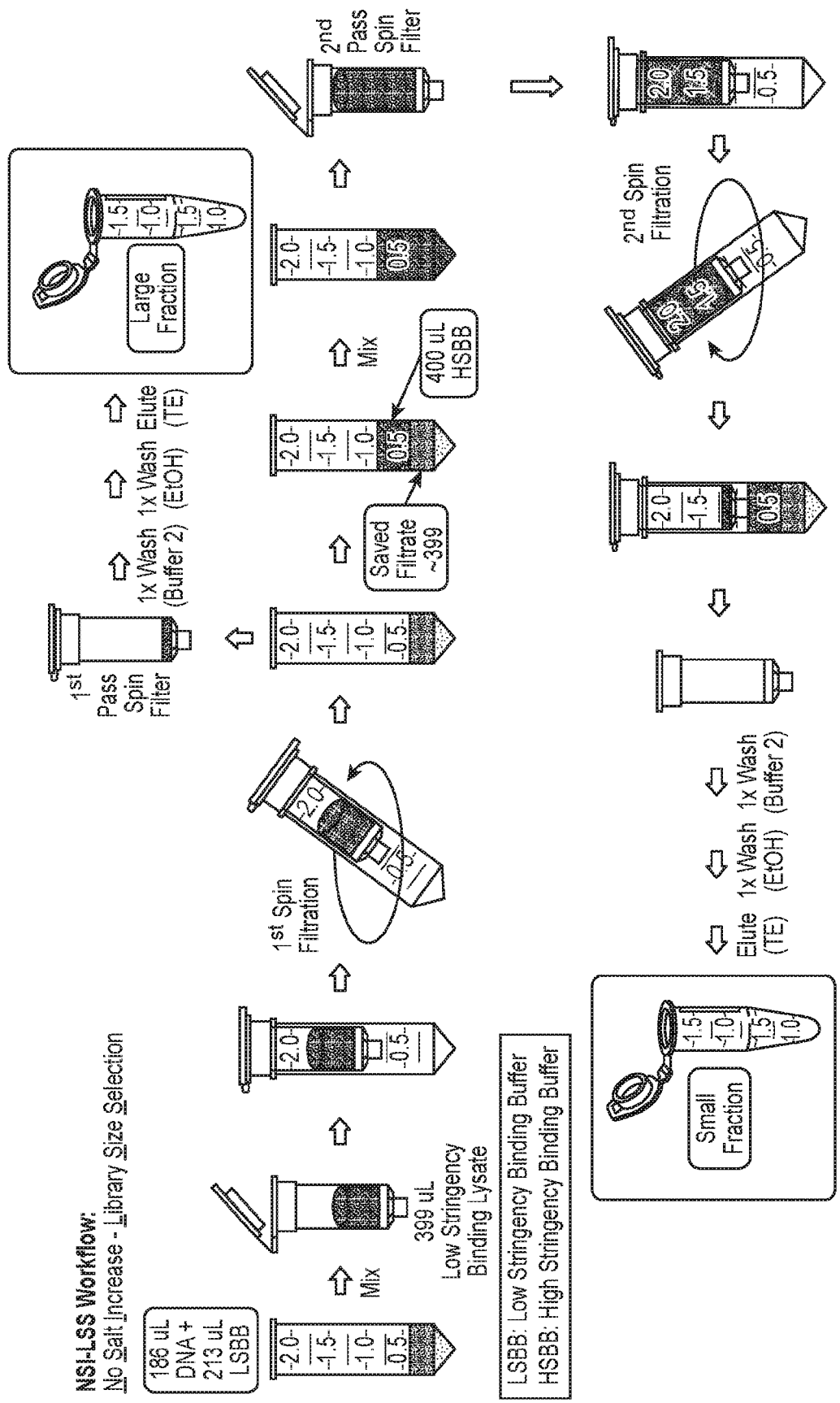
FIG. 31 shows the No Salt Increase-Library Size Selection (NSI-LSS) workflow. This workflow demonstrated dual-filtration size selection in a spin column format that has been applied to partition DNA library products into a large and a small fraction. This method utilized the same low and high stringency binding principle, wherein chaotropic salt in the low stringency binding condition begins at >30% and remained unchanged, or decreased slightly, in the high stringency binding condition. A purified or unpurified cfDNA library sample (186 uL) is combined with 213 µL of low stringency binding buffer (LSBB) to establish the low stringency binding condition, and the mixture is then applied to a glass fiber filter or silica membrane spin column and placed into a spin tube (as shown). The assembly is place into a centrifuge for the $1^{st}$ spin filtration, which allows the low stringency binding condition to make contact with the solid support, while the filtrate collects in the lower spin tube and is saved for secondary processing. The $1^{st}$ spin column is removed and spin processed to wash 1× with wash buffer and 1× with EtOH, and elute in a low ionic strength buffer (i.e., 10 mM Tris, 0.1 mM EDTA, pH 8). This recovers a library fraction containing the largest of the DNA fragments (i.e., Large Fraction). The filtrate saved from the $1^{st}$ spin is mixed with 400 uL high stringency binding buffer (HSBB) to create the high stringency binding condition and applied to a new glass fiber or silica membrane spin column. The $2^{nd}$ spin filtration allows the high stringency binding condition to contact the solid support and capture the remaining smaller DNA fragments. The $2^{nd}$ spin column is removed, washed 1× with wash buffer 1× with EtOH, and eluted in TE to return the smallest of the DNA fragments (i.e., Small Fraction).
Figure 32:
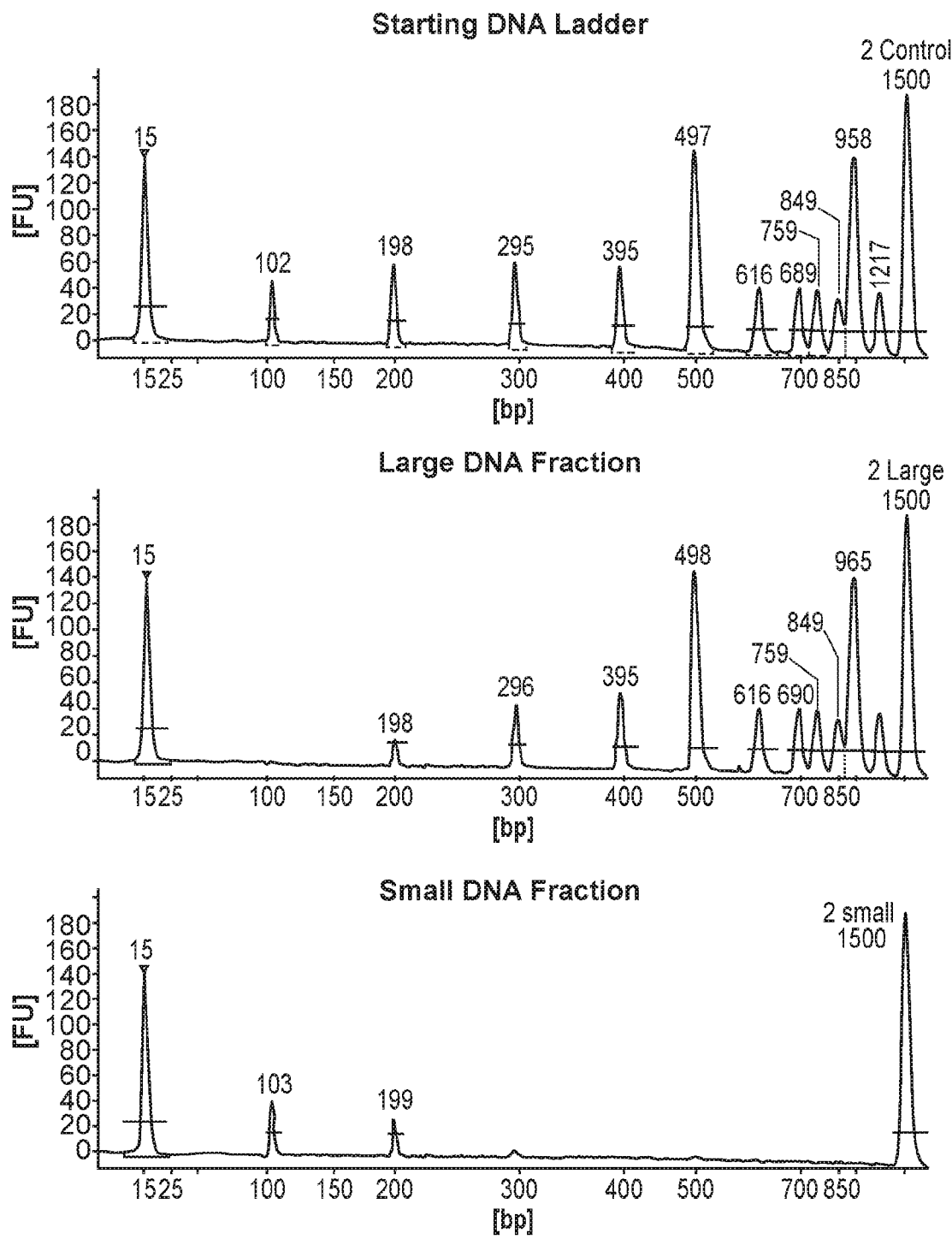
FIG. 32 graphically depicts an electropherogram (CE) tracer generated by BioAnalyzer™ 1K of a DNA Ladder treated with the NSI-LSS method detailed in FIG. 31. Each CE trace exhibited size markers at 15 and 1500 base pairs, which flank peaks in the ZipRuler™ DNA ladder. The top panel shows peaks in the native ladder. The middle panel shows peaks eluted from the $1^{st}$ spin column (Large DNA Fraction) following NSI-LSS separation. The bottom panel shows peaks eluted from the $2^{nd}$ spin column (Small DNA Fraction). The Large DNA Fraction shows a marked reduction in peaks at 200 and 300 bp in size and an absence of the 100 bp peak. Conversely, the Small DNA Fraction shows recovery of all the 100 bp peak and the balance of the 200 and 300 bp peaks that were not captured by the $1^{st}$ pass.

The compositions of the low and high stringency binding conditions established in the methods depicted in FIG. 26 and FIG. 31 are shown in FIG. 27. The experimental results deriving from these conditions are presented in FIGS. 28 through 35. The components and concentrations established with LSBB when added to plasma or library products in the proportions described in FIG. 26 and FIG. 31 are shown in FIG. 27 in the upper table, whereas. the lower table lists components and concentrations established following addition of HSBB to lysates recovered following 1st Pass vaccum or 1st Spin Column filtration.

Results

Evidence that modulation of solvent type and concentration can strongly affect length-dependent affinity of dsDNA fragments in crude lysates for glass or silica substrates is presented most clearly in FIGS. 4, and 7. These experiments demonstrated that the percentage of 72 bp and 118 bp fragments recovered depended on the mobile phase concentration of the solvent acetonitrile, as well as propionitrile, butyronitrile, and isobutryonitrile.

Figure 28:
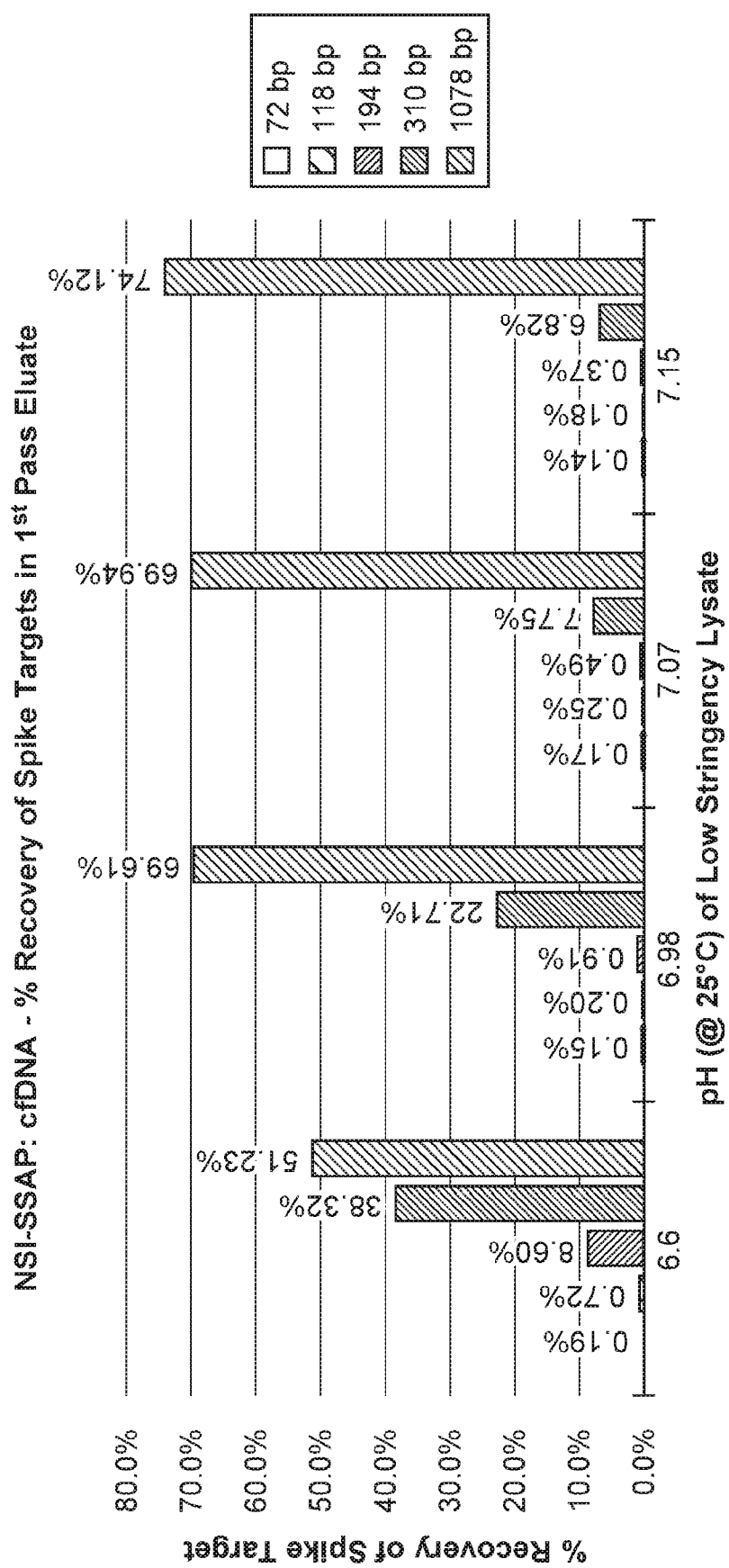
FIG. 28 graphically depicts elution of spiked fragments of DNA size 72, 118, 194, 310, and 1078 base pairs from the 1st pass filtration (large DNA fragments) with lysates titrated with Tris buffer to a pH between 6.6 to 7.15 in the low stringency binding condition. As the pH of the low stringency binding condition increases, the affinity of the shorter DNA fragments for the glass fiber filter or silica membrane decreases. Reciprocally, as pH decreases the affinity of shorter DNA fragments for the glass fiber filter or silica membrane, increases. This differential affinity was achieved following the addition of high stringency binding buffer (HSBB) without changing the concentration of the chaotropic salt.

The effect of pH on the length dependency of glass fiber or silica membrane binding was shown in FIG. 28, where the percentage of 310 bp fragment (checkerboard pattern) decreased with increasing pH. Such data indicated that multiple parameters can affect the affinity of dsDNA for finely spun borosilicate glass fibers or silica membranes, and that DNA length itself has a profound effect on the strength of the interaction.

The % recovery data obtained for fragments of DNA size 72, 118, 194, 310, and 1078 base pairs that were spiked into plasma lysates and eluted from the 1st pass columns (i.e., the large DNA fragments) is shown in FIG. 28. In the series presented, the spiked plasma lysates were titrated with a buffered Tris solutions to obtain pH values between 6.6 and 7.15 within the low stringency binding condition. As the pH of the low stringency binding condition increases, the affinity of the shorter DNA fragments for the glass fiber filter or silica membrane decreases. Reciprocally, as pH decreases the affinity of shorter DNA fragments for the glass fiber filter or silica membrane, increases. This differential affinity is achieved following the addition of high stringency binding buffer (HSBB) without changing the concentration of the chaotropic salt.

Example 3.1—Using Size Selections at Purification (NSI-SSAP) to Enrich for the Fetal Cell-Free DNA from Maternal Plasma Samples Next, we evaluated if the size exclusion methods developed herein can enrich for fetal cell-free DNA from maternal plasma samples. The average length of cell-free DNA fragments originating from the child and present in the maternal circulation are shorter, ~143 bp, compared to the average cfDNA of the mother, ~166 bp as previously reported (Chan K C A, Zhang J, Hui A B, et al. (2004) Size distributions of maternal and fetal DNA in maternal plasma, *Clin Chem.* 50(1):88-92, and Fan H C, Blumenfeld Y J, Chitkara U, Hudgins L, Quake S R (2010) Analysis of the size distributions of fetal and maternal cell-free DNA by paired-end sequencing, *Clin Chem.* 56(8):1279-1286). The percentage of fetal DNA present in maternal blood is on average only 10%, but frequently less than 5% in plasma samples, particularly in plasma collected in the $1^{st}$ trimester of pregnancy.

As with SSAP, the length discrepancy should make it possible to increase the apparent child fraction by enriching for cfDNA fragments at the time of purification. NSI-SSAP was used to simultaneously purify and size select cfDNA from the blood plasma from 10 pregnant women. The cfDNA was preserved and analyzed in the single nucleotide polymorphism (SNP) based non-invasive prenatal test (NIPT) Panorama (Samango-Sprouse C, Banjevic M, Ryan A, et al. (2013) SNP-based non-invasive prenatal testing detects sex chromosome aneuploidies with high accuracy. *Prenatal Diagnostics* 33:643-9, and Hall M P, Hill M, Zimmermann, P B, et al (2014) Non-invasive prenatal detection of trisomy 13 using a single nucleotide polymorphism- and informatics-based approach. *PLoS One* 9:e96677). The Panorama™ assay may be used to calculate the proportion of fetal to maternal SNP's, accurately reported as the percent child fraction estimate (% CFE). If shorter cfDNA fragments are indeed enriched in the small cfDNA fraction, the proportion of child SNP's should be higher than the control from a non-size selected cfDNA fraction. Reciprocally, the % CFE in the large fraction should be reduced compared to control.

Figure 29:
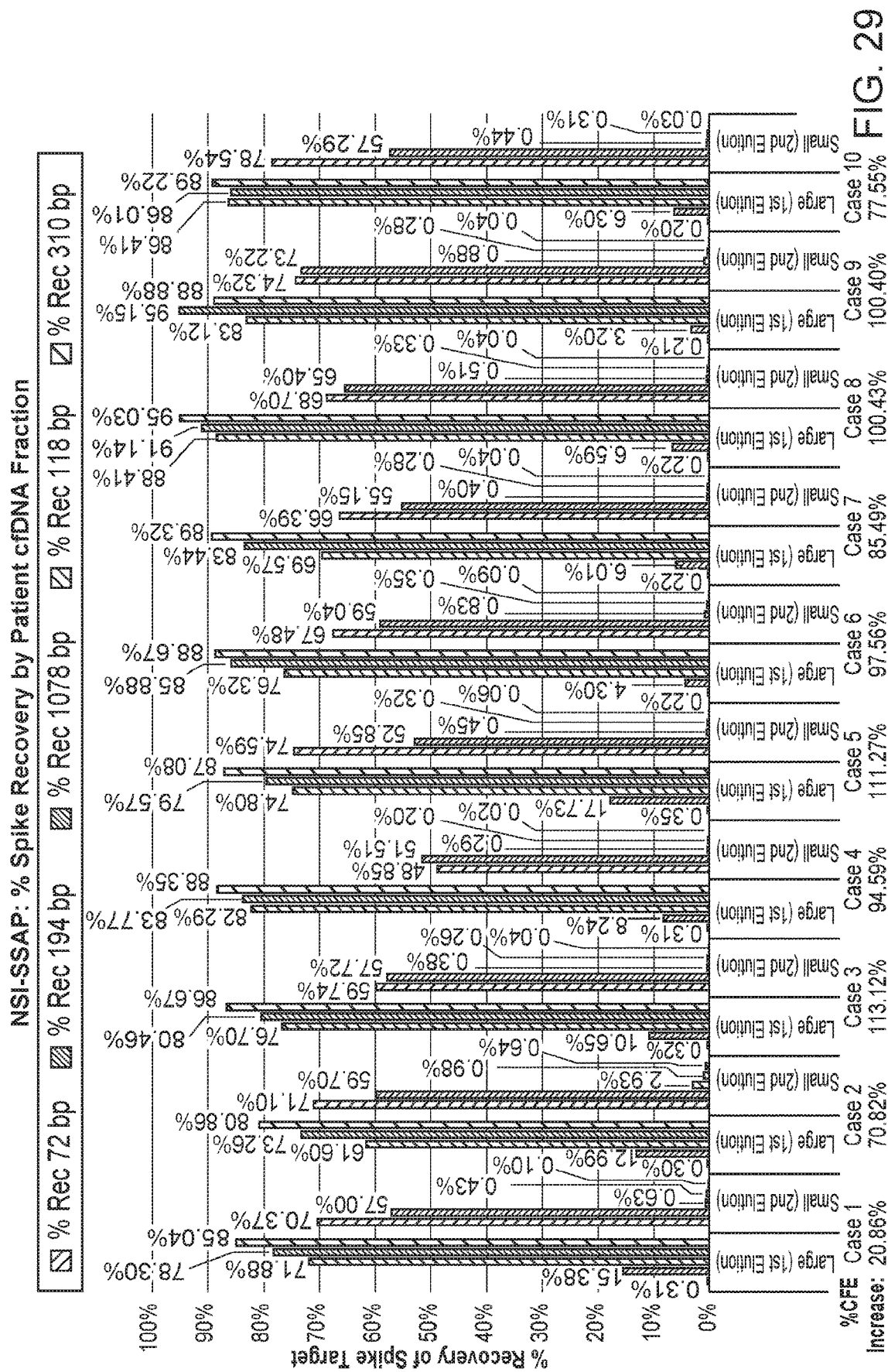
FIG. 29 graphically depicts percent recovery of spike targets in the large ($1^{st}$ column elution) and small ($2^{nd}$ column elution) from 10 mL of pregnancy plasma samples processed by Size Selection At Purification (SSAP). 200 µL of 20 mg/mL Proteinase K and 11.7 mL of low stringency binding buffer (LSBB) was added to each 10 mL plasma to establish the low stringency binding condition and prepared larger fragments of DNA to selectively bind onto the glass fiber filter/silica membrane. In this example, the majority of DNA spike fragments 194 bp and larger were captured on the $1^{st}$ pass filter. High stringency binding buffer (HSBB) was then added to the filtrate from the $1^{st}$ pass filter to establish the high stringency binding condition where the smaller DNA fragments not bound by the $1^{st}$ pass filter are efficiently captured by the $2^{nd}$ pass glass fiber filter/silica membrane. This is revealed by the selective capture of the 72, 118, and some 194 bp, DNA spike fragments in the $2^{nd}$ pass eluate presented for each case. The size selection obtained with this method shows exclusion of large DNA fragments in the small fraction which is directly correlated with the increased child fraction estimates (% CFE), and showing convincingly that the small fraction is enriched in fetal cfDNA.

To test if NSI-SSAP method could enrich for fetal cfDNA, 10 mL of pregnancy plasma (10 unique cases), was processed by the NSI-SSAP method. Proteolysis was initiated with the additions of 200 µL of 20 mg/mL Proteinase K and 11.7 mL of low stringency binding buffer (LSBB) added to each 10 mL plasma. The addition of these two components established the low stringency binding condition, which caused larger DNA fragments to bind glass fiber filter/silica membranes, in conditions that, at the same time, disfavored binding of smaller DNA fragments also present in the lysate. In this example, the majority of DNA spike fragments >194 bp bound with high efficiency to the 1st pass filter. Next, high stringency binding buffer (HSBB) was added to the $1^{st}$ Pass filtrate to establish the high stringency binding condition where now the smaller DNA fragments that did not bind to the 1st filter can be efficiently captured by the $2^{nd}$ pass glass fiber filter/silica membrane. It was found that 72, 118, and some 194 bp, were detected in high percentage in the 2nd pass eluates recovered for each case. The percentage of spike targets recovered in the large fraction (1st column elution) and small fraction (2nd column elution) are shown in FIG. 29. The size selection obtained with this method showed exclusion of large DNA fragments in the small fraction, which was directly correlated with increased child fraction estimates (% CFE), listed below each case as shown in FIG. 29. Thus, it was found that the small fraction was enriched for fragments of cfDNA of fetal origin.

In summary, the data shown in FIG. 29 demonstrated that the NSI-SSAP enriched for cfDNA Small Fractions ($2^{nd}$ Elution). In particular, NSI-SSAP enriched for the 72 bp and 118 bp spike targets, and this method enriched for fetal SNP's partitioning with cfDNA fragments that were shorter on average. In this example, under the size selection conditions practiced, NSI-SSAP resulted in relative increase in the % CFE in the cfDNA Small Fraction of 87%, which constituted a near doubling of the CFE.

Next a data fit prediction of the % CFE results from the above experiment shown in FIG. 29, were performed and the result is shown in FIG. 30. The plot shown in FIG. 30 compared cfDNA fractions isolated without size selection, the Control (Ctrl), to the 1st Elution (large cfDNA fraction) and the 2nd Elution (small cfDNA fraction), for all cases. This required that two ×10 mL plasma samples be extracted for each case. The cfDNA from one 10 mL aliquot was processed to recover total cfDNA, while the other was processed by the NSI-SSAP method to partition cfDNA into the $1^{st}$ Pass filter eluate (large cfDNA fraction) and the $2^{nd}$ Pass filter eluate (small cfDNA fraction). Compared to Control, lower % CFE values were obtained for the large cfDNA fractions, and higher % CFE values were observed in the $2^{nd}$ Pass (small cfDNA) fractions. Thus, the data analysis shown in FIG. 30 indicated that the small cfDNA fraction is enriched for fetal cfDNA fragments compared to either control or large cfDNA fraction In other words, the plot shown in FIG. 30 demonstrated that shorter cfDNA fragments are enriched in the small cfDNA fraction, and thus, the proportion of child SNP's (% CFE) is higher in the cfDNA Small Fraction than in the Control, and lower in the cfDNA Large Fraction.

Example 3.2—Using No Salt Increase for Library Size Selection (NSI-LSS) to Enrich for cfDNA Preserved in Molecular Libraries The experiments shown in FIGS. 29 and 30 demonstrated how the NSI-SSAP method can be aptly applied to enrich shorter cfDNA fragments in a manner that is coincident with purification and directly from plasma. Moreover, the method is easily extendable to dsDNA fragments in other backgrounds. In the following examples the alternate low and high stringency binding strategy will be demonstrated when applied to cfDNA's preserved in molecular libraries.

To produce the library, the ends of each cfDNA, regardless of state, are repaired enzymatically and ligated to DNA adapter molecules to give each cfDNA a common forward and reverse primer binding site at either end. This immortalized the cfDNA and allowed all members of the library to be uniformly amplified many times to increase their numbers without biasing the proportion of any in the population. Amplified libraries from the Panorama NIPT test were taken through a modified protocol at smaller scale. FIG. 31 presented the NSI-LSS adaptation for library size selection in a spin column and centrifuge based method. The method depicted is an exactly scaled version of the plasma NSI-SSAP workflow using identical LSBB and HSBB compositions, so that the concentrations in the low and high stringency binding condition match those detailed in FIG. 27.

The No Salt Increase—Library Size Selection (NSI-LSS) workflow where dual-filtration size selection has been adapted to a spin column format and applied to size select DNA library products into larger and smaller DNA fractions is outlined in FIG. 31. The method utilized the same low and high stringency binding principles, under which the chaotropic salt concentration in the low stringency binding condition begins at >30% and remains unchanged, or decreased slightly, in the shift to high stringency binding conditions. In the adaptation, 186 µL of purified or unpurified library sample, typically but not necessarily derived from cfDNA, was combined with 213 µL of low stringency binding buffer (LSBB) to establish the low stringency binding condition. The mixture was applied to a glass fiber filter or silica membrane spin column and placed into a spin tube as shown. The assembly was centrifuged to force the low stringency binding condition through the glass fiber/silica membrane in the $1^{st}$ filtration step, while the low stringency filtrate collected in the lower spin tube below, and was carefully preserved for secondary processing. The $1^{st}$ spin column was removed and processed separately to receive a 1× wash in Wash Buffer 1, 1× wash in EtOH, and eluted with a low ionic strength buffer such as TE (10 mM Tris, 0.1 mM EDTA, pH 8). This partitioned the larger of the library DNA fragments into the "Large Fraction". The filtrate saved from the $1^{st}$ spin was then mixed with 400 μL high stringency binding buffer (HSBB) to establish a high stringency binding condition. This was applied to a new glass fiber filter/ silica membrane spin column and centrifuged to pass the high stringency binding condition across the solid filter membrane to capture the remaining, smaller, library DNA fragments. The 2nd spin column was washed 1× with Wash Buffer, 1× with EtOH, and eluted in TE to recover the smaller of the library DNA fragments in the "Small Fraction".

To examine the degree of size separation and obtain an estimate for the size cutoff for the NSI-LSS size selection method practiced in FIG. 31, a dsDNA ladder having fragments in the region of interest (100 bp to 1200 bp) diluted in 10 mM Tris, 0.1 mM EDTA was taken through the spin protocol. Ladder fragments in the original ladder and the large and small fractions were analyzed by capillary electrophoresis (CE) and the traces are presented in FIG. 32.

Capillary electrophoresis (CE) traces were generated on an Agilent BioAnalyzer™ (1K chip) of a broad range (100 bp to 1200 bp) DNA Ladder treated by the NSI-LSS method, as detailed in FIG. 31. Each CE trace included two size markers at 15 and 1500 base pairs, which flank peaks from the DNA ladder. The top trace was of the native ladder showing the starting abundance of each peak. The middle panel showed peaks that were eluted from the $1^{st}$ spin column (Large DNA Fraction) in the NSI-LSS workflow. The bottom panel showed peaks eluting from the $2^{nd}$ spin column (Small DNA Fraction). The Large DNA Fraction showed a marked reduction in peaks at 200 and 300 bp, and an absence of the 100 bp peak altogether. Conversely, the Small DNA Fraction showed full recovery of all the 100 bp peak and the remaining balance of the 200 and 300 bp peaks not captured in the $1^{st}$ pass filtration.

The NSI-LSS size selection method as practiced in FIG. 31 was applied to an amplified library diluted in 10 mM Tris, 0.1 mM EDTA. A sample of the non-size selected starting library and the large and small fractions from the size-selected library were analyzed in parallel by capillary electrophoresis (CE). For overlay clarity, just the traces from the Large and Small fractions are co-presented in FIG. 33. The Large fraction comprised two peaks at 239 bp and 391 bp, consistent with cfDNA molecules of mono-nucleosomal and di-nucleosomal origin. The Small fraction showed the presence of only one peak, representing cfDNA of mononucleosomal origin. The single Small fraction peak was also center shifted by −10 bp compared to the similar peak in the Large fraction, indicating enrichment for library fragments of smaller size.

Capillary electrophoresis (CE) traces were generated on an Agilent BioAnalyzer™ (1K chip), resolving amplified library products size-selected using the NSI-LSS method detailed in FIG. 31. In the Large Fraction Library products eluting from the $1^{st}$ spin column there were two peaks because it was comprised of DNA fragments that originated from cell-free (cf) DNAs that were both di-nucleosome and mono-nucleosome in size. The library method added 63 bp to each cfDNA fragment, so that the peaks observed at 239 and 391 bp were in fact quite close to the expected sizes of ~230 bp and ~380 bp that were generated from mono- and di-nucleosome sized cfDNA fragments. Library products eluting from the $2^{nd}$ spin column were devoid of fragments in the di-nucleosome size range. The peak labeled "Small Fraction Library" migrated with an average length of 229 bp, or ~10 bp shorter than the equivalent library peak eluted from the 1st spin column. This shift portended a slight reduction in the average length of the monosome derived library fragments recovered in the small fraction. The small fraction also appeared to be enriched for even smaller fragments, as the left shoulder of the peak falled slowly off, indicating that there was an abundance of library products originating from the much smaller cfDNA fragments.

Figure 33:
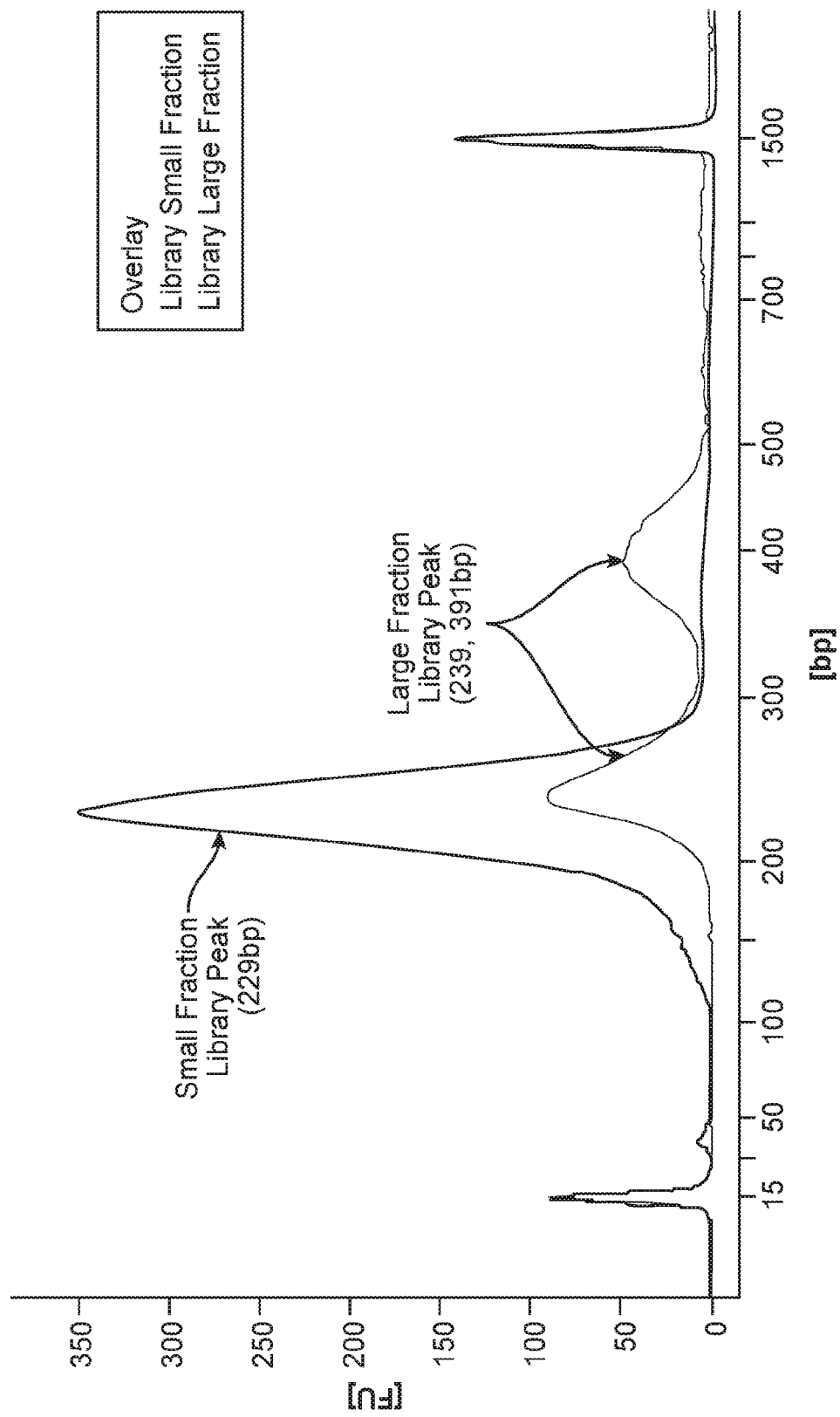
FIG. 33 graphically depicts an electropherogram generated by BioAnalyzer™ 1K, resolving amplified library products size selected by the NSI-LSS method detailed in FIG. 31. Library products eluting from the $1^{st}$ spin column contained DNA fragments originating from cell-free DNA of di-nucleosomal and mono-nucleosomal in size. The library method adds 63 bp to each cfDNA fragment, so that the peaks observed at 239 and 391 bp as shown in the graph are close to the expected peak sizes of ~230 and ~380 bp for mono- and di-nucleosome derived fragments, respectively. Library products eluting from the $2^{nd}$ spin column were devoid of fragments in the di-nucleosome size range (~380 bp). The peak labeled Small Fraction Library migrated with an average length of 229 bp, 10 bp shorter than the equivalent peak from the $1^{st}$ spin column. Also, the small fraction appears to be enriched in even smaller fragments, as evidenced by the rise in the left shoulder of the graph, indicating the presence of library products originating from smaller cfDNA fragments.

To examine the degree of library size selection and obtain an estimate for the size cutoff under the conditions used to generate FIG. 33, the NSI-LSS method was performed on three library samples and the partitioning of 5 spike targets between the Large and Small library fractions was quantitatively tracked by qPCR. The results are presented in FIG. 34 and demonstrated that a majority of fragments larger than 310 bp in size were retained in the Large fraction. Since the average length of fragments in the starting library is 225 bp, the method tested herein likely imposed a very modest degree of size selection among the mono-nucleosomal derived fragments. Still, removing fragments larger in size would be expected to result in a child fraction increased by partitioning proportionally more maternally derived (i.e, on average larger) library cfDNA fragments, particularly those di-nucleosomal in size, into the large fraction.

Figure 34:
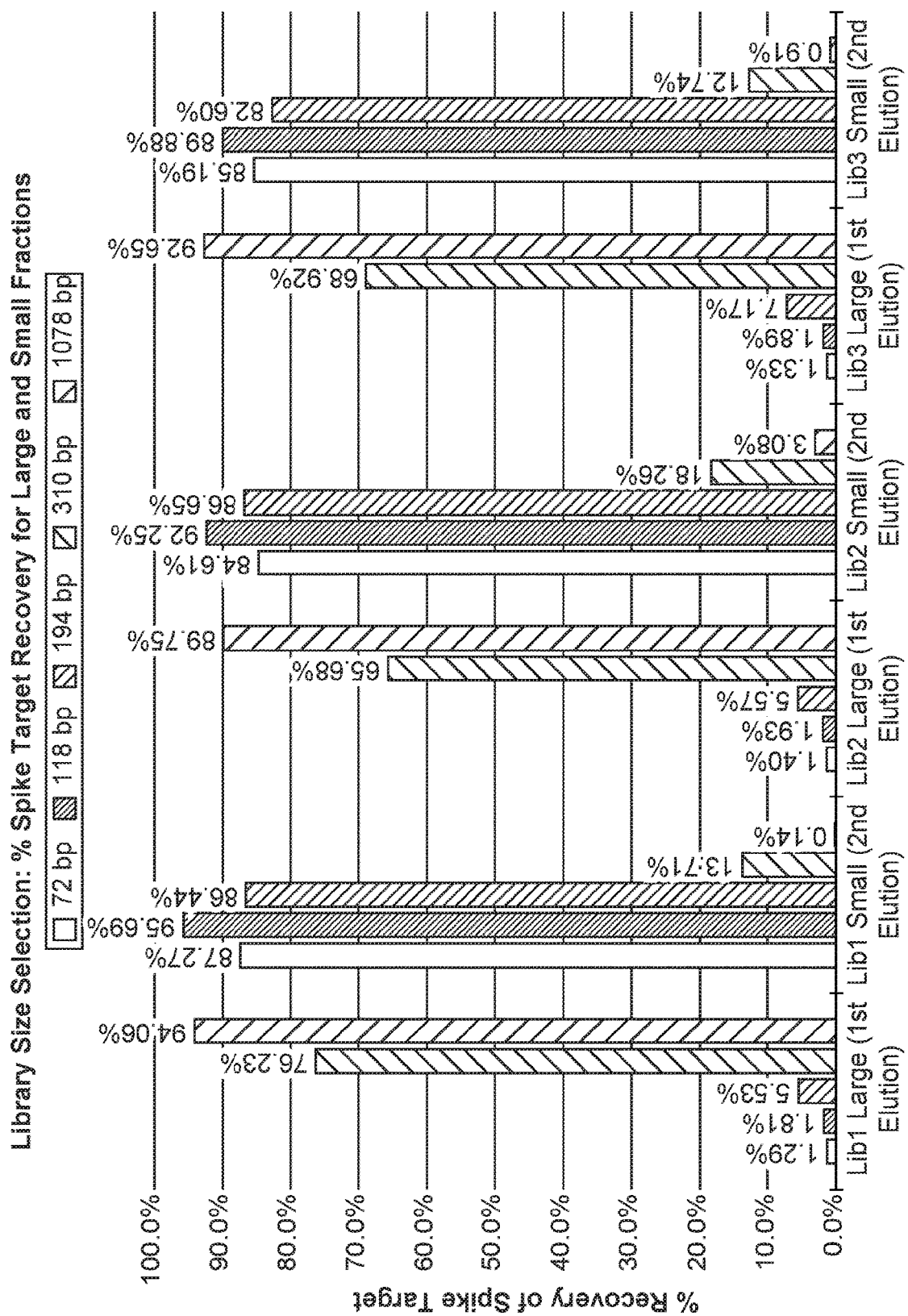
FIG. 34 graphically depicts percent recovery of spike fragments at 72, 118, 194, 310, and 1078 base pairs, that were added to libraries prepared from cfDNA derived from pregnancy plasma samples. Following library size selection by the NSI-LSS method (FIG. 31), spike recovery of all 5 was determined by qPCR. The NSI-LSS method subdivided each library into a Large DNA fraction and a Small DNA fraction. The majority of 310 bp spike fragments were bound by 1st spin column and were therefore returned at a high rate of recovery (66-76%) within the Large Fraction Library. The $2^{nd}$ spin column by contrast enriched the 72, 118, and 194 bp fragments in the Small Fraction Library, which are much smaller than 310 bp.

The percent recovery of spike targets at 72, 118, 194, 310, and 1078 base pairs, that were added to libraries prepared from pregnancy plasma derived cfDNA is shown in FIG. 34. Following library size selection by the NSI-LSS method (FIG. 31), spike recovery of all 5 spike targets was determined by real time quantitative PCR (RT-qPCR). The NSI-LSS method subdivided each library into a Large DNA fraction and a Small DNA fraction. The majority of 310 bp spike targets were detected at a high rate of recovery (66-76%) within the Large Fraction Library eluted from the $1^{st}$ spin column. By contrast, the 72, 118, and 194 bp fragments were detected in the Small Fraction Library.

To definitively show that libraries treated to the NSI-LSS method were enriched for shorter cfDNA fragments, the method was applied to 13 libraries generated from the plasma cfDNA from pregnant women early in gestation. Size selected library products in the Large and Small fractions were taken through the Panorama NIPT assay and child fraction estimated obtained shown in FIG. 35.

Figure 35:
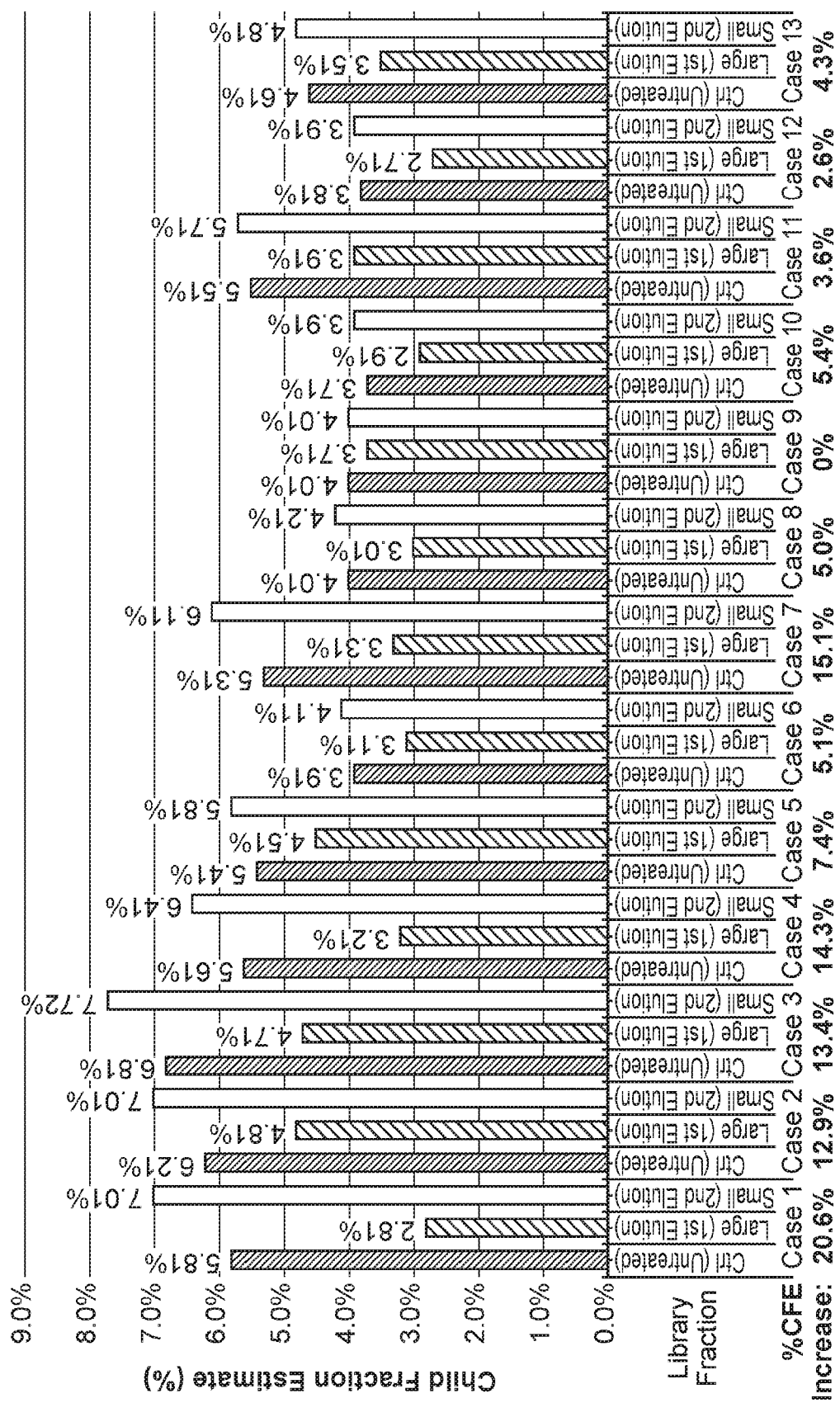
FIG. 35 graphically depicts the NIS-LSS method as applied to amplified libraries generated from 13 pregnancy plasma samples to test the effect on child fraction estimates (CFE). The data are plotted to compare % CFE for control (Ctrl), having no size selection, and representing the total library DNA fraction, with the Large Library DNA Fraction ($1^{st}$ spin column elution), and the Small Library DNA Fraction ($2^{nd}$ spin column elution). Experimentally, a portion of non-selected library from each pregnancy case served as control. Another portion of the library was treated to NSI-LSS to obtain % CFE for library product returned from the $1^{st}$ spin and $2^{nd}$ spin columns. In every case but case #9, the control and large elution ($1^{st}$ spin column eluate) had lower % CFE than the library product eluted from the $2^{nd}$ spin column. This demonstrates that smaller DNA fragments not captured by the $1^{st}$ spin column are enriched for smaller fetal DNA fragments.

Next, the NIS-LSS method was applied to amplified libraries generated from 13 pregnancy plasma samples to test the effect on child fraction estimates (CFE). The data are plotted to compare % CFE for control (Ctrl) libraries having no size selection, against the Large Library DNA Fraction (1st spin column elution), and the Small Library DNA Fraction (2nd spin column elution) within the same sample as shown in FIG. 35. A portion of the non-selected library from each pregnancy case served as control. Another portion of the library was treated to NSI-LSS to obtain % CFE for library product returned from the 1st spin and 2nd spin columns. In every case, except case #9, the control and large library fractions (1st spin column eluate) had lower % CFE than the library small library fraction eluted from the 2nd spin column. This demonstrated that smaller DNA fragments that escaped being captured by the 1st spin were subsequently captured by the 2$^{nd}$ spin column under the higher stringency conditions and, proved to be enriched for smaller fetal DNA fragments.

As expected, the average Small fraction increase in % CFE for the 13 cases presented was modest, with an average relative increase of 8.44%.

Example 3.3—The LibAddition Strategy to Increase the Average Size of the Population of Library Products It is proposed herein that % CFE may be increased without altering the chemical environment in either the low or high stringency binding conditions by uniformly increasing the overall length of the library itself. Shifting the center of the library size distribution upward, without altering the size cutoff under low stringency, will cause more library fragments to partition into the Large fraction (1$^{st}$ pass eluate) relative to the Small fraction. This approach is referred to as the LibAddtion strategy and is outlined in FIG. 36.

The LibAddition strategy enables selection of shorter preserved cfDNA fragments without changing the chemistry of the NSI-LSS method. Rather, the library size is increased while the low stringency binding condition remains constant. For example, the NSI-LSS method, as it is applied in FIG. 31 and demonstrated in FIGS. 32 and 34, restricted library products <~310 bp in eluates from the 2nd spin column, (the Small Faction Library). Under these conditions, cfDNA fragments <~250 bp in size (310–63=247) were enriched.

In the LibAddition strategy a DNA fragment of known length is appended to each library fragment to shift the average size of the population of library products to enrich for cfDNA fragments preserved in the library without altering the chemistry of the method.

Figure 36:
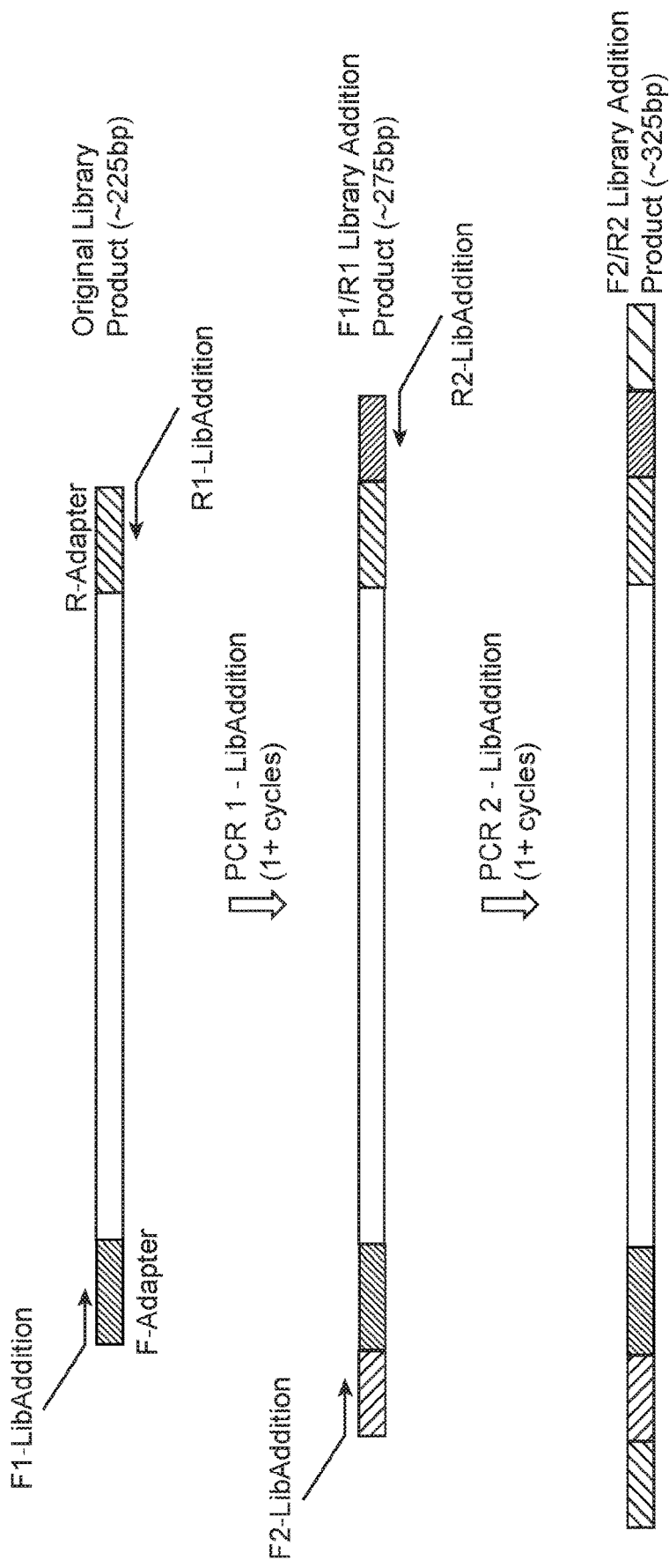
FIG. 36 graphically depicts the LibAddition strategy to select for even shorter preserved cfDNA fragments without changing the size selection properties of the NSI-LSS method. The NSI-LSS method as it is applied in FIG. 31, and demonstrated in FIGS. 32 and 34, restricts library products <~310 bp in eluates from the $2^{nd}$ spin column, (the Small Faction Library). Under these conditions, cfDNA fragments <~250 bp in size (310−63=247) are enriched. To enrich for cfDNA fragments preserved in the library even smaller in size, without altering the chemistry of the method, one can append each fragment with a known length of DNA to shift the average size of the population of library products.

In the LibAddition strategy, an additional 25 bp is added to each library product by method known as tailing PCR as shown in FIG. 36. Following one or more rounds of PCR with primers F1/R1-LibAddition, an additional 50 bp is added to each library fragment. Another ~50 bp can subsequently be added to increase the length of the resultant F1/R1 long product with primers F2/R2-LibAddition. Under the scheme depicted, the average length of library fragments below the cutoff and selected in the Small Library Fraction would reduce to <~200 bp for F1/R1 products and to <~150 bp for the F2/R2 products. Given that the average length of the cfDNA fragments preserved in original library were ~166 bp (see FIG. 33 (~229–63=166 bp), size selection of the F1/R1-LibAddition products would shift the cutoff and have the effect of reducing the average length of preserved cfDNA recovered in the Small Library Fraction to <~116 bp. An even further reduction in length would be had for F2/R2 products, where average cfDNA length preserved would fall to <~66 bp.

While the ability to increase the representation of small cfDNA fragments in given sample at the time of purification by NSI-SSAP or once converted to an immortalized representative library by NSI-LSS has been tested directly and demonstrated herein using the increases in child fraction estimate as a readout, the method is fully translatable to conceivably any non-invasive test that queries cfDNA. These would include circulating tumor DNA, circulating pathogen DNA, circulating DNA from a transplanted organ. In addition, the methods would extent to circulating tumor mRNA, miRNA, lncRNA once converted to dsDNA.

As used herein, the singular terms "a," "an," and "the" include plural referents unless the context clearly dictates otherwise. Thus, for example, reference to a molecule can include multiple molecules unless the context clearly dictates otherwise.

As used herein, the terms "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. For example, the terms can refer to less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations, which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scopes of this invention.

What is claimed is:

1. A method for isolating nucleic acids from a biological sample, comprising:
    (a) contacting a first composition comprising nucleic acids in a biological sample with a first solid phase nucleic acid binding matrix to obtain a filtrate and a first eluate, wherein the first composition comprises:
        (i) less than 1% aliphatic alcohols,
        (ii) about 3.2055 M to about 4.76 M of a chaotropic compound,
        (iii) about 0% to about 12.1% of a nitrile compound,
        (iv) a pH of about 6.6 to about 7.157,
        (v) 0% to about 9% of a detergent, and
        (vi) 0% to about 1.2% of a chelating agent;
        wherein the first composition permits binding of greater than 30% of nucleic acids longer than about 194 bp to the first matrix, wherein the filtrate comprises remainder nucleic acids passed through the first matrix, and wherein the first eluate comprises nucleic acids bound and released from the first matrix; and (b) contacting a second composition comprising the filtrate comprising remainder nucleic acids from the first composition with a second solid phase nucleic acid binding matrix to obtain a second eluate, wherein the second composition comprises:
  (i) less than 1% aliphatic alcohols,
  (ii) about 3.2055 M to about 4.76 M of a chaotropic compound,
  (iii) about 20% to about 30% of a nitrile compound,
  (iv) a pH of about 4.05 to about 5.5,
  (v) 0% to about 9.55% of a detergent, and
  (vi) about 0 to about 0.61 mM of a chelating agent;
  wherein the second composition binds more than 40% of nucleic acids longer than about 72 bp to the second matrix, wherein the second eluate comprises nucleic acids bound and released from the second matrix; wherein the first and the second solid phase nucleic acid binding matrices comprise siliceous materials, silica gel, glass, glass fiber, or gelatinous silica.

2. The method of claim 1, further comprising washing the first matrix with a washing buffer after step (a), and eluting nucleic acids from the first matrix with an elution buffer to obtain the first eluate.

3. The method of claim 1, wherein the second eluate is obtained by washing the second matrix with a washing buffer after the contacting in step (b), and eluting nucleic acids from the second matrix with an elution buffer.

4. The method of claim 1, further comprising digesting the biological sample with a protease prior to step (a).

5. The method of claim 1,
wherein the nitrile compound of the first and/or second composition comprises acetonitrile (ACN), propionitrile (PCN), butyronitrile (BCN), isobutylnitrile (IBCN), or a combination thereof; and
wherein the chaotropic compound of the first and/or second composition comprises guanidine chloride (GnCl), urea, thiourea, guanidine thiocyanate, NaI, guanidine isothiocyanate, D-/L-arginine, a perchlorate or perchlorate salt of Li+, Na+, K+, or a combination thereof.

6. The method of claim 1, wherein the first composition comprises ACN as the nitrile compound, and about 3.2055 M to about 4 M of GnCl as the chaotropic compound; and wherein the second composition comprises ACN as the nitrile compound and about 3.5 M to about 4.76 M of GnCl as the chaotropic compound.

7. The method of claim 1, wherein the detergent comprises Triton X-100, Tween 20, N-lauroyl sarcosine, sodium dodecylsulfate (SDS), dodecyldimethylphosphine oxide, sorbitan monopalmitate, decylhexaglycol, 4-nonylphenyl-polyethylene glycol, or a combination thereof; and wherein the chelating compound comprises ethylenediaminetetracetic (EDTA), ethyleneglycol-bis (2-aminoethylether)-N,N,N',N'-tetraacetic acid (EGTA), citric acid, N,N,N',N'-Tetrakis(2-pyridylmethyl)ethylenediamine (TPEN), 2,2'-Bipyridyl, deferoxamine methanesulfonate salt (DFOM), 2,3-Dihydroxybutanedioic acid (tartaric acid), or a combination thereof; and
  wherein the first composition and/or the second composition comprises less than 1% of alcohol.

8. The method of claim 1, wherein the biological sample is a plasma sample from a pregnant woman comprising fetal cfDNA and maternal cfDNA, or a plasma sample from a cancer patient comprising circulating tumor DNA; wherein when the biological sample is a plasma sample from a pregnant woman, fetal fraction of nucleic acids elutable from the second solid phase nucleic acid binding matrix is at least 1% higher than fetal fraction of nucleic acids elutable from the first solid phase nucleic acid binding matrix.

9. The method of claim 1, wherein step (a) binds more than 40% of nucleic acids longer than about 194 bp to the first solid phase nucleic acid binding matrix, and wherein step (b) binds more than 80% of nucleic acids longer than about 72 bp to the second solid phase nucleic acid binding matrix.

10. The method of claim 1, wherein the first composition further comprises Tris(hydroxymethyl) aminomethane (Tris-base), a chelating compound, and a detergent.

11. The method of claim 10, wherein the first composition comprises the biological sample in an amount from 38.9% to about 45.66%.

12. The method of claim 10, wherein the nitrile compound is acetonitrile, the chelating compound is EDTA, the detergent is Tween 20, and the chaotropic compound is guanidine chloride; wherein the biological sample is a plasma sample from a pregnant woman comprising fetal cell-free DNA (cfDNA) and maternal cfDNA, or a plasma sample from a cancer patient comprising circulating tumor DNA (ctDNA); and wherein:
  the method further comprising amplifying the cfDNA or ctDNA prior to step (a) by ligating the cfDNA or the ctDNA to a plurality of DNA adapter molecules, wherein the DNA adapter molecules comprises common forward and reverse primer binding sites, and then amplifying the ligated cfDNA or ctDNA by using forward and reverse primers complementary to the common primer binding sites in the DNA adaptor molecules, or
  the method further comprising adding a plurality of DNA base pairs to the cfDNA or ctDNA fragments by tailing PCR to increase the size of the cfDNA or ctDNA fragments prior to step (a).

13. The method of claim 1, wherein the second composition comprises 2-(N-morpholino) ethanesulfonic acid (MES).

14. The method of claim 13, wherein the second composition comprises, the MES in an amount from about 4.59 mM to about 38 mM.

* * * * *